US009859502B2

(12) United States Patent
Buesing et al.

(10) Patent No.: US 9,859,502 B2
(45) Date of Patent: Jan. 2, 2018

(54) MATERIALS FOR ELECTRONIC DEVICES

(71) Applicant: Merck Patent GmbH, Darmstadt (DE)

(72) Inventors: Arne Buesing, Frankfurt am Main (DE); Irina Martynova, Griesheim (DE); Frank Voges, Bad Duerkheim (DE); Jonas Valentin Kroeber, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 44 days.

(21) Appl. No.: 15/030,565

(22) PCT Filed: Sep. 24, 2014

(86) PCT No.: PCT/EP2014/002586
§ 371 (c)(1),
(2) Date: Apr. 19, 2016

(87) PCT Pub. No.: WO2015/058826
PCT Pub. Date: Apr. 30, 2015

(65) Prior Publication Data

US 2016/0268509 A1 Sep. 15, 2016

(30) Foreign Application Priority Data

Oct. 23, 2013 (EP) .................................... 13005070

(51) Int. Cl.

| | |
|---|---|
| ***H01L 51/00*** | (2006.01) |
| ***C09K 11/06*** | (2006.01) |
| ***H05B 33/10*** | (2006.01) |
| ***C07C 211/54*** | (2006.01) |
| ***C07C 211/61*** | (2006.01) |
| ***C07D 307/91*** | (2006.01) |
| ***C07C 209/74*** | (2006.01) |
| ***C09K 11/02*** | (2006.01) |
| *H01L 51/50* | (2006.01) |

(52) U.S. Cl.

CPC .......... *H01L 51/006* (2013.01); *C07C 209/74* (2013.01); *C07C 211/54* (2013.01); *C07C 211/61* (2013.01); *C07D 307/91* (2013.01); *C09K 11/025* (2013.01); *C09K 11/06* (2013.01); *H01L 51/0054* (2013.01); *H01L 51/0061* (2013.01); *H05B 33/10* (2013.01); *C07C 2603/18* (2017.05); *C07C 2603/52* (2017.05); *C07C 2603/90* (2017.05); *C07C 2603/97* (2017.05); *C09K 2211/1007* (2013.01); *C09K 2211/1011* (2013.01); *C09K 2211/1014* (2013.01); *C09K 2211/1029* (2013.01); *C09K 2211/185* (2013.01); *H01L 51/0055* (2013.01); *H01L 51/0056* (2013.01); *H01L 51/0058* (2013.01); *H01L 51/0073* (2013.01); *H01L 51/506* (2013.01); *H01L 51/5012* (2013.01); *H01L 51/5056* (2013.01); *H01L 51/5088* (2013.01); *H01L 51/5096* (2013.01); *Y02E 10/549* (2013.01)

(58) Field of Classification Search

CPC ............... H01L 51/006; H01L 51/0061; H01L 51/0054; H01L 51/5088; H01L 51/5096; H01L 51/0058; H01L 51/0056; H01L 51/0055; H01L 51/0073; H01L 51/506; H01L 51/5056; H01L 51/5012; C07D 307/91; H05B 33/10; Y02E 10/549; C09K 11/025; C09K 11/06; C09K 2211/1029; C09K 2211/185; C09K 2211/1011; C09K 2211/1014; C09K 2211/1007

See application file for complete search history.

(56) References Cited

FOREIGN PATENT DOCUMENTS

CN 102030701 A 4/2011

OTHER PUBLICATIONS

Hounshell et al, Structure of Hexaphenylethane and Congeners as Determined by Empirical Force Field Calculations, Journal of the American Chemical Society, vol. 99, Issue 6, pp. 1916-1924, 1977.*
Baum et al, Carbenic Processes in Decomposition of Spiro[fluorine-9,3'-indazole]. A Simple route to the Fluoradene System, Jounral of Organic Chemistry, vol. 41, Issue 12, pp. 2120-2124, 1976.*
International Search Report for PCT/EP2014/002586 dated Dec. 2, 2014.
Rong, L., et al., "Fluoradenes via palladium-cataslyzed intramolecular arylation", Chemical Communications, vol. 47, No. 7, (2011), pp. 2155-2157.
Tuchscherer, C., et al., "Preparation of 2H-cyclopenta[j,k]fluorene and substituted fluoradenes", Tetrahedron Letters, vol. 11, (1973), pp. 865-868.
Xia, A., et al., "Two fluoradene derivatives: pseudosymmetry, eccentric ellipsoids and phase transition", Acta Crystallographica Section B, vol. B57, (2001), pp. 507-516.

* cited by examiner

*Primary Examiner* — Alexander Kollias

(57) ABSTRACT

The invention relates to compounds according to formula (1), said compounds being suitable for use in electronic devices, in particular in organic electroluminescent devices.

15 Claims, No Drawings

MATERIALS FOR ELECTRONIC DEVICES

CROSS-REFERENCE TO RELATED APPLICATIONS

This application is a national stage application (under 35 U.S.C. §371) of PCT/EP2014/002586, filed Sep. 24, 2014, which claims benefit of European Application No. 13005070.1, filed Oct. 23, 2013, both applications of which are incorporated herein by reference in their entirety.

The present invention relates to materials for use in electronic devices, especially in organic electroluminescent devices.

The development of functional compounds for use in electronic devices is currently the subject of intensive research. The particular aim here is to develop compounds with which improved properties of the electronic devices can be achieved in one or more relevant aspects, for example power efficiency, lifetime or color coordinates of the light emitted.

The term “electronic device” is understood in accordance with the present invention to mean devices including organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and organic electroluminescent devices (OLEDs).

Of particular interest is the provision of compounds for use in the latter electronic devices referred to as OLEDs. The general structure of OLEDs and the way in which they work is known to those skilled in the art and described, inter alia, in U.S. Pat. No. 4,539,507, U.S. Pat. No. 5,151,629, EP 0676461 and WO 1998/27136.

BACKGROUND OF THE INVENTION

With regard to the performance data of OLEDs, further improvements are still required, especially with regard to broad commercial use, for example in display devices or as light sources. Of particular significance in this connection are the lifetime, the efficiency and the operating voltage of the OLEDs, and the color values achieved. Especially in the case of blue-emitting OLEDs, there is potential for improvement with regard to the lifetime of the devices. In addition, it is desirable that the compounds, for use as functional materials in electronic devices, have a high thermal stability and a high glass transition temperature and can be sublimed without decomposition.

Document CN 102030701A describes compounds having an indeno[1,2,3-jk]fluorene skeleton. Document US 2006/0094859 A1 describes polymers having multiply bridged biphenyl units.

DETAILED DESCRIPTION OF THE INVENTION

It is an object of the present invention to provide compounds suitable for use in a fluorescent or phosphorescent OLED, especially a phosphorescent OLED, for example as matrix material and/or as hole transport/electron blocker material or exciton blocker material and/or as electron transport or hole blocker material.

For the sake of clarity, the numbering of indeno[1,2,3-jk]fluorene is depicted below:

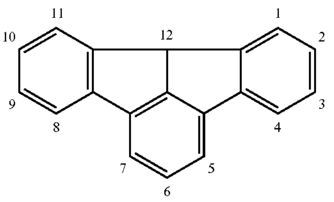

The present invention therefore provides a compound of formula (I)

Formula (1)

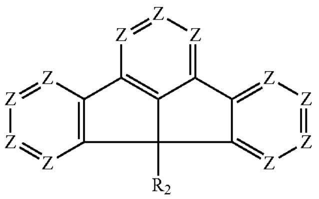

where the symbols that occur are as follows:

Z is the same or different at each instance and is $CR^1$ or N;

$Ar^1$ is the same or different at each instance and is an aromatic or heteroaromatic ring system which has 5 to 60 aromatic ring atoms and may be substituted by one or more $R^3$ radicals; at the same time, two $Ar^1$ radicals bonded to the same nitrogen atom or phosphorus atom may also be bridged to one another by a single bond or a bridge selected from $N(R^4)$, $C(R^4)_2$, O and S;

$R^1$ is the same or different at each instance and is H, D, F, Cl, Br, I, CN, $NO_2$, $N(Ar^1)_2$, $N(R^3)_2$, $C(=O)Ar^1$, $C(=O)R^3$, $P(=O)(Ar^1)_2$, $P(=O)(R^3)_2$, $B(OR^3)_2$, CHO, $Si(R^3)_2$, $OSO_2R^3$, $S(=O)R^3$, $S(=O)_2R^3$, a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, where the alkyl, alkoxy, thioalkyl, alkenyl or alkynyl group may be substituted in each case by one or more $R^3$ radicals and where one or more adjacent or nonadjacent $CH_2$ groups may be replaced by $-R^3C{=}CR^3-$, $-C{\equiv}C-$, C=O, C=S, C=Se, $C{=}NR^3$, $-C(=O)-NR^3-$, $P(=O)(R^3)$, $-C(=O)-O-$, $Si(R^3)_2$, $NR^3$, —O—, —S—, SO or $SO_2$ and where one or more hydrogen atoms may be replaced by D, F, Cl, Br, I, CN or $NO_2$, or an aromatic ring system which has 6 to 60 aromatic ring atoms and may be substituted in each case by one or more $R^3$ radical(s), or a heteroaromatic ring system which has 5 to 60 aromatic ring atoms and may be substituted in each case by one or more $R^3$ radical(s), where two or more $R^1$ radicals may be joined to one another and may form a ring;

$R^2$ is the same or different at each instance and is H, D, F, Cl, Br, I, CN, $NO_2$, $N(Ar^1)_2$, $N(R^3)_2$, $C(=O)Ar^1$, $C(=O)R^3$, $P(=O)(Ar^1)_2$, $P(=O)(R^3)_2$, $B(OR^3)_2$, CHO, $Si(R^3)_2$, $OSO_2R^3$, $S(=O)R^3$, $S(=O)_2R^3$, a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, where the alkyl, alkoxy, thioalkyl, alkenyl or alkynyl group may be substituted in each case by one or more $R^3$ radicals and where one or more adjacent or nonadjacent $CH_2$ groups may be replaced by $-R^3C{=}CR^3-$, $-C{\equiv}C-$, $C{=}O$, $C{=}S$, $C{=}Se$, $C{=}NR^3$, $-C({=}O)-NR^3-$, $P({=}O)(R^3)$, $-C({=}O)-O-$, $Si(R^3)_2$, $NR^3$, $-O-$, $-S-$, SO or $SO_2$ and where one or more hydrogen atoms may be replaced by D, F, Cl, Br, I, CN or $NO_2$, or an aromatic ring system which has 6 to 60 aromatic ring atoms and may be substituted in each case by one or more $R^3$ radical(s), or a heteroaromatic ring system which has 5 to 60 aromatic ring atoms and may be substituted in each case by one or more $R^3$ radical(s);

$R^3$ is the same or different at each instance and is H, D, F, Cl, Br, I, CN, $NO_2$, $N(R^4)_2$, $C({=}O)Ar^1$, $C({=}O)R^4$, $P({=}O)(Ar^1)_2$, $B(OR^4)_2$, CHO, $Si(R^4)_2$, $OSO_2R^4$, $S({=}O)R^4$, $S({=}O)_2R^4$, a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, where the alkyl, alkoxy, thioalkyl, alkenyl or alkynyl group may be substituted in each case by one or more $R^4$ radicals and where one or more adjacent or nonadjacent $CH_2$ groups may be replaced by $-R^4C{=}CR^4-$, $-C{\equiv}C-$, $C{=}O$, $C{=}S$, $C{=}Se$, $C{=}NR^4$, $-C({=}O)-NR^4-$, $P({=}O)(R^4)$, $-C({=}O)-O-$, $Si(R^4)_2$, $NR^4$, $-O-$, $-S-$, SO or $SO_2$ and where one or more hydrogen atoms may be replaced by D, F, Cl, Br, I, CN or $NO_2$, or an aromatic ring system which has 6 to 60 aromatic ring atoms and may be substituted in each case by one or more $R^4$ radical(s), or a heteroaromatic ring system which has 5 to 60 aromatic ring atoms and may be substituted in each case by one or more $R^4$ radical(s), where two or more $R^4$ radicals may be joined to one another and may form a ring;

$R^4$ is the same or different at each instance and is H, D, F, CN or an aliphatic radical having 1 to 20 carbon atoms, or an aromatic ring system having 6 to 60 aromatic ring atoms or a heteroaromatic ring system having 5 to 60 aromatic ring atoms, where one or more hydrogen atoms in the aliphatic radical, the aromatic ring system or the heteroaromatic ring system may be replaced by D, F, Cl, Br, I, CN or an alkyl group having 1 to 5 carbon atoms, where two or more $R^4$ radicals may be joined to one another and may form a ring;

where $R^2$ and/or at least one $R^1$ of the formula (1) comprises at least one aromatic or heteroaromatic ring system; and when at least one $R^1$ comprises at least one aromatic or heteroaromatic ring system, the total number of aromatic ring atoms in all $R^1$ and $R^2$ is at least 12; and when $R^1$ does not comprise an aromatic or heteroaromatic ring system, $R^2$ comprises at least 24 aromatic ring atoms and no further indeno[1,2,3-jk]fluorene skeleton bonded via the 12 position.

An aryl group in the context of this invention contains 6 to 60 aromatic ring atoms; a heteroaryl group in the context of this invention in principle contains 5 to 60 aromatic ring atoms, at least one of which is a heteroatom. The heteroatoms are preferably selected from N, O and/or S. This is the fundamental definition. If other preferences are stated in the description of the present invention, for example with regard to the number of aromatic ring atoms or of heteroatoms present, these are applicable.

An aryl group or heteroaryl group is understood here to mean either a simple aromatic cycle, i.e. benzene, or a simple heteroaromatic cycle, for example pyridine, pyrimidine, thiophene, etc., or a fused (annelated) aromatic or heteroaromatic polycycle, for example naphthalene, anthracene, phenanthrene, quinoline, isoquinoline or carbazole. A fused (annelated) aromatic or heteroaromatic polycycle, in the context of the present application, consists of two or more simple aromatic or heteroaromatic cycles fused to one another. Aromatic systems joined to one another by a single bond, for example biphenyl or bipyridine, by contrast, are not referred to as an aryl or heteroaryl group but as an aromatic ring system.

An aryl or heteroaryl group, each of which may be substituted by the abovementioned radicals and which may be joined to the aromatic or heteroaromatic system via any desired positions, is especially understood to mean groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the context of this invention contains 6 to 60 aromatic ring atoms in the ring system. A heteroaromatic ring system in the context of this invention contains 5 to 60 aromatic ring atoms, at least one of which is a heteroatom. The heteroatoms are preferably selected from N, O and/or S. An aromatic or heteroaromatic ring system in the context of this invention is understood to mean a system which does not necessarily contain only aryl or heteroaryl groups, but in which it is also possible for two or more aryl or heteroaryl groups to be bonded by a nonaromatic unit (preferably less than 10% of the atoms other than H), for example an $sp^3$-hybridized carbon, silicon, nitrogen or oxygen atom, an $sp^2$-hybridized carbon or nitrogen atom or an sp-hybridized carbon atom. For example, systems such as 9,9'-spirobifluorene, 9,9'-diarylfluorene, triarylamine, diaryl ethers, stilbene, etc. are also to be regarded as aromatic ring systems in the context of this invention, and likewise systems in which two or more aryl groups are joined, for example, by a linear or cyclic alkyl, alkenyl or alkynyl group or by a silyl group. In addition, systems in which two or more aryl or heteroaryl groups are joined to one another via single bonds are also to be regarded as aromatic or heteroaromatic ring systems in the context of this invention, for example systems such as biphenyl, terphenyl or diphenyltriazine.

An aromatic or heteroaromatic ring system which has 5-60 aromatic ring atoms and may also be substituted in each case by radicals as defined above and which may be joined to the aromatic or heteroaromatic system via any desired positions is especially understood to mean groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or combinations of these groups.

In the context of the present invention, a straight-chain alkyl group having 1 to 40 carbon atoms and a branched or cyclic alkyl group having 3 to 40 carbon atoms and an alkenyl or alkynyl group having 2 to 40 carbon atoms in which individual hydrogen atoms or $CH_2$ groups may also be replaced by the groups mentioned above in the definition of the radicals are preferably understood to mean the methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl radicals. An alkoxy or thioalkyl group having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The wording that two or more radicals together may form a ring, in the context of the present description, shall be understood to mean, inter alia, that the two radicals are joined to one another by a chemical bond. This is illustrated by the following scheme:

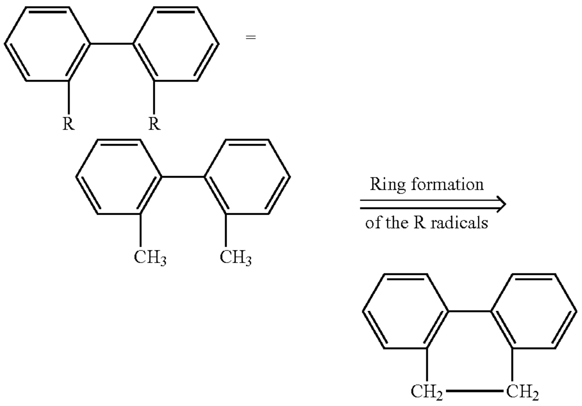

In addition, however, the abovementioned wording shall also be understood to mean that, if one of the two radicals is hydrogen, the second radical binds to the position to which the hydrogen atom was bonded, forming a ring. This shall be illustrated by the following scheme:

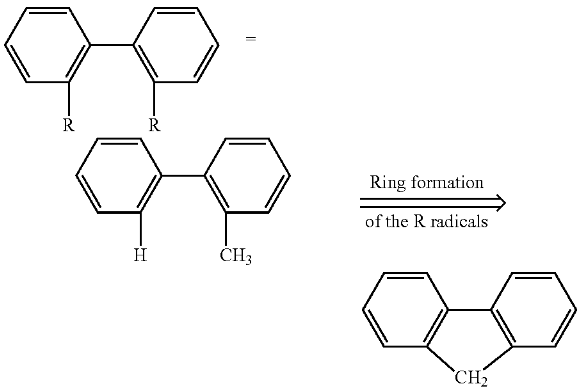

In a preferred embodiment of the invention, not more than one Z group per cycle is N and the other Z groups are the same or different at each instance and are $CR^1$. In a particularly preferred embodiment of the invention, all Z groups are the same or different at each instance and are $CR^1$.

When at least one $R^1$ comprises at least one aromatic or heteroaromatic ring system, the total number of aromatic ring atoms in all $R^1$ and $R^2$ is at least 12; preferably at least 18, more preferably at least 24.

When $R^1$ does not comprise an aromatic or heteroaromatic ring system, $R^2$ comprises at least 24 aromatic ring atoms and no further indeno[1,2,3-jk]fluorene skeleton.

This achieves a certain flexibility and minimum size of $R^2$, which has a positive effect on the stability of the compound, especially in the case of use in sublimation. Especially the 12 position in indeno[1,2,3-jk]fluorene skeletons is the most acidic position in the skeleton. Therefore, these bonds are particularly unstable. If there are still further indeno[1,2,3-jk]fluorene skeletons in the compound, it becomes not just very large but also potentially less stable.

Preferably, $R^1$ and/or $R^2$ do not comprise any fused aromatic or heteroaromatic ring systems having more than 14 aromatic ring atoms.

Likewise preferably, all $R^1$ and $R^2$ together comprise a total number of aromatic ring atoms of not more than 84, preferably not more than 60.

A preferred embodiment of the compound of the formula (1) is therefore a compound of the following formula (2):

Formula (2)

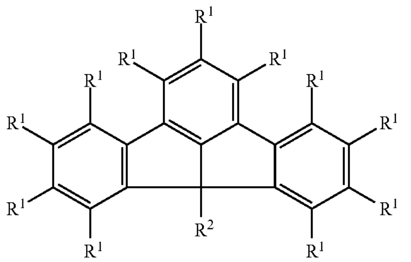

where the symbols used are as defined above.

In a preferred embodiment of the invention, $R^1$ in the abovementioned formulae is the same or different at each instance and is H, D, F, Cl, Br, CN, $NO_2$, $N(Ar^1)_2$, $N(R^3)_2$, C(═O)$Ar^1$, C(═O)$R^3$, a straight-chain alkyl, alkoxy or thioalkyl group having 1 to 20 carbon atoms or a branched or cyclic alkyl, alkoxy or thioalkyl group having 3 to 20 carbon atoms or an alkenyl or alkynyl group having 2 to 20 carbon atoms, where the alkyl, alkoxy, thioalkyl, alkenyl or alkynyl group may in each case be substituted by one or more $R^3$ radicals and where one or more nonadjacent $CH_2$ groups may be replaced by $Si(R^3)_2$, —S— and —O— and where one or more hydrogen atoms may be replaced by D or F, or an aromatic ring system which has 6 to 30 aromatic ring atoms and may be substituted in each case by one or more $R^3$ radical(s), or a heteroaromatic ring system which has 5 to 30 aromatic ring atoms and may be substituted in each case by one or more $R^3$ radical(s), where two or more $R^1$ radicals may be joined to one another and may form a ring.

In a further preferred embodiment of the invention, $R^1$ in the abovementioned formulae is the same or different at each instance and is H, D, F, CN, $NO_2$, $N(Ar^1)_2$, $N(R^3)_2$, C(═O)$Ar^1$, C(═O)$R^3$, a straight-chain alkyl, alkoxy or thioalkyl group having 1 to 20 carbon atoms or a branched or cyclic alkyl, alkoxy or thioalkyl group having 3 to 20 carbon atoms or an alkenyl or alkynyl group having 2 to 20 carbon atoms, where the alkyl, alkoxy, thioalkyl, alkenyl or alkynyl group may in each case be substituted by one or more $R^3$ radicals and where one or more nonadjacent $CH_2$ groups may be replaced by $Si(R^3)_2$, —S— and —O— and where one or more hydrogen atoms may be replaced by D or F, or an aromatic ring system which has 6 to 30 aromatic ring atoms and may be substituted in each case by one or more $R^3$ radical(s), or a heteroaromatic ring system which has 5 to 30 aromatic ring atoms and may be substituted in each case by one or more $R^3$ radical(s), where two or more $R^1$ radicals may be joined to one another and may form a ring.

In a further preferred embodiment of the invention, $R^1$ in the abovementioned formulae is the same or different at each instance and is H, D, F, CN, $NO_2$, $N(Ar^1)_2$, $N(R^3)_2$, a straight-chain alkyl or alkoxy group having 1 to 10 carbon atoms or a branched or cyclic alkyl or alkoxy group having 3 to 10 carbon atoms or an alkenyl or alkynyl group having 2 to 10 carbon atoms, where the alkyl, alkoxy, alkenyl or alkynyl group may in each case be substituted by one or more $R^3$ radicals and where one or more nonadjacent $CH_2$ groups may be replaced by $Si(R^3)_2$, —S— and —O— and where one or more hydrogen atoms may be replaced by D or F, or an aromatic ring system which has 6 to 30 aromatic ring atoms and may be substituted in each case by one or more $R^3$ radical(s), or a heteroaromatic ring system which has 5 to 30 aromatic ring atoms and may be substituted in each case by one or more $R^3$ radical(s), where two or more $R^1$ radicals may be joined to one another and may form a ring.

In a preferred embodiment of the invention, $R^2$ in the abovementioned formulae is the same or different at each instance and is H, D, F, Cl, Br, CN, $NO_2$, $N(Ar^1)_2$, $N(R^3)_2$, C(═O)$Ar^1$, C(═O)$R^3$, a straight-chain alkyl, alkoxy or thioalkyl group having 1 to 20 carbon atoms or a branched or cyclic alkyl, alkoxy or thioalkyl group having 3 to 20 carbon atoms or an alkenyl or alkynyl group having 2 to 20 carbon atoms, where the alkyl, alkoxy, thioalkyl, alkenyl or alkynyl group may in each case be substituted by one or more $R^3$ radicals and where one or more nonadjacent $CH_2$ groups may be replaced by $Si(R^3)_2$, —S— and —O— and where one or more hydrogen atoms may be replaced by D or F, or an aromatic ring system which has 6 to 30 aromatic ring atoms and may be substituted in each case by one or more $R^3$ radical(s), or a heteroaromatic ring system which has 5 to 30 aromatic ring atoms and may be substituted in each case by one or more $R^3$ radical(s).

In a further preferred embodiment of the invention, $R^2$ in the abovementioned formulae is the same or different at each instance and is H, D, F, CN, $NO_2$, $N(Ar^1)_2$, $N(R^3)_2$, C(═O)$Ar^1$, C(═O)$R^3$, a straight-chain alkyl, alkoxy or thioalkyl group having 1 to 20 carbon atoms or a branched or cyclic alkyl, alkoxy or thioalkyl group having 3 to 20 carbon atoms or an alkenyl or alkynyl group having 2 to 20 carbon atoms, where the alkyl, alkoxy, thioalkyl, alkenyl or alkynyl group may in each case be substituted by one or more $R^3$ radicals and where one or more nonadjacent $CH_2$ groups may be replaced by $Si(R^3)_2$, —S— and —O— and where one or more hydrogen atoms may be replaced by D or F, or an aromatic ring system which has 6 to 30 aromatic ring atoms and may be substituted in each case by one or more $R^3$ radical(s), or a heteroaromatic ring system which has 5 to 30 aromatic ring atoms and may be substituted in each case by one or more $R^3$ radical(s).

In a further preferred embodiment of the invention, $R^2$ in the abovementioned formulae is the same or different at each instance and is H, D, F, CN, $N(Ar^1)_2$, $N(R^3)_2$, a straight-chain alkyl or alkoxy group having 1 to 10 carbon atoms or a branched or cyclic alkyl or alkoxy group having 3 to 10 carbon atoms or an alkenyl or alkynyl group having 2 to 10 carbon atoms, where the alkyl, alkoxy, alkenyl or alkynyl group may in each case be substituted by one or more $R^3$ radicals and where one or more nonadjacent $CH_2$ groups may be replaced by $Si(R^3)_2$, —S— and —O— and where one or more hydrogen atoms may be replaced by D or F, or an aromatic ring system which has 6 to 30 aromatic ring atoms and may be substituted in each case by one or more $R^3$ radical(s), or a heteroaromatic ring system which has 5 to 30 aromatic ring atoms and may be substituted in each case by one or more $R^3$ radical(s).

In a further preferred embodiment of the invention, $R^2$ in the above formulae is an aromatic ring system which has 6 to 30 aromatic ring atoms and may be substituted by one or more $R^3$ radical(s).

In a further embodiment of the invention, $R^3$ in the abovementioned formulae is the same or different at each instance and is H, D, F, CN, $N(R^4)_2$, C(═O)$R^4$, $Si(R^4)_2$, a straight-chain alkyl, alkoxy or thioalkyl group having 1 to 20 carbon atoms or a branched or cyclic alkyl, alkoxy or thioalkyl group having 3 to 20 carbon atoms or an alkenyl or alkynyl group having 2 to 20 carbon atoms, where the alkyl, alkoxy, thioalkyl, alkenyl or alkynyl group may in each case be substituted by one or more $R^4$ radicals and where one or more adjacent or nonadjacent $CH_2$ groups may be replaced by $Si(R^4)_2$, $NR^4$, —O— or —S— and where one or more hydrogen atoms may be replaced by D, F or CN, or an aromatic ring system which has 6 to 18 aromatic ring atoms and may be substituted in each case by one or more $R^4$ radical(s), or a heteroaromatic ring system which has 5 to 18 aromatic ring atoms and may be substituted in each case by one or more $R^4$ radical(s), where two or more $R^4$ radicals may be joined to one another and may form a ring.

In a further embodiment of the invention, $R^1$ at at least one of positions 5 and 10 in the indeno[1,2,3-jk]fluorene skeleton is the same or different at each instance and is H, D, F, CN, $NO_2$, $N(Ar^1)_2$, $N(R^3)_2$, $C(=O)Ar^1$, $P(=O)(Ar^1)_2$, $P(=O)(R^3)_2$, $Si(R^3)_2$, $OSO_2R^3$, $S(=O)R^3$, $S(=O)_2R^3$, a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, where the alkyl, alkoxy, thioalkyl, alkenyl or alkynyl group may be substituted in each case by one or more $R^3$ radicals and where one or more adjacent or nonadjacent $CH_2$ groups may be replaced by $—R^3C=CR^3—$, —C≡C—, C=O, C=S, C=Se, $C=NR^3$, $—C(=O)—NR^3—$, $P(=O)(R^3)$, —C(=O)—O—, $Si(R^3)_2$, $NR^3$, —O—, —S—, SO or $SO_2$ and where one or more hydrogen atoms may be replaced by D, F, Cl, Br, I, CN or $NO_2$, or an aromatic ring system which has 6 to 60 aromatic ring atoms and may be substituted in each case by one or more $R^3$ radical(s), or a heteroaromatic ring system which has 5 to 60 aromatic ring atoms and may be substituted in each case by one or more $R^3$ radical(s), where two or more $R^1$ radicals may be joined to one another and may form a ring. More preferably, $R^1$ at positions 5 and 10 of the indeno[1,2,3-jk]fluorene skeleton, if present in each case, does not contain any radicals selected from the group comprising Cl, Br, I, $B(OR^3)_2$ and CHO.

For compounds which are processed by vacuum evaporation, the alkyl groups here preferably have not more than 4 carbon atoms. For compounds which are processed from solution, suitable compounds are also those substituted by alkyl groups having up to 10 carbon atoms or those substituted by oligoarylene groups, for example ortho-, meta-, para- or branched terphenyl or quaterphenyl groups.

In a further embodiment of the invention, at least one $R^1$ is not H; preferably, at least one $R^1$ comprises an aromatic or heteroaromatic ring system.

Particularly preferred aromatic ring systems for $R^1$ and $R^2$ are selected from the group of phenyl, ortho-, meta- or para-biphenyl, ortho-, meta- or para-terphenyl, ortho-, meta-, para- or branched quaterphenyl, fluorene, spirobifluorene, each of which may be substituted by one or more $R^3$ radicals.

Particularly preferred aromatic ring systems for $R^1$ and $R^2$ are especially selected from the structures of the following formulae:

Formula (A-1)

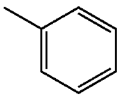

-continued

Formula (A-2)

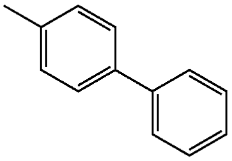

Formula (A-3)

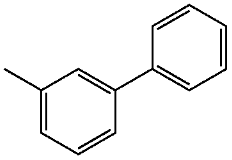

Formula (A-4)

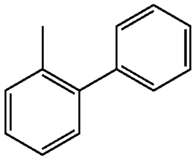

Formula (A-5)

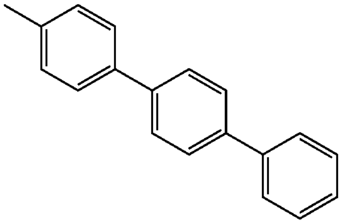

Formula (A-6)

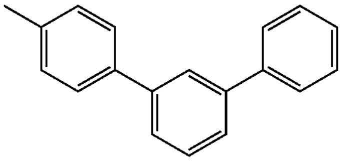

Formula (A-7)

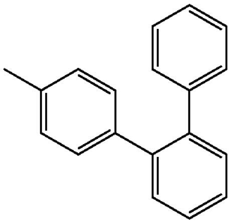

Formula (A-8)

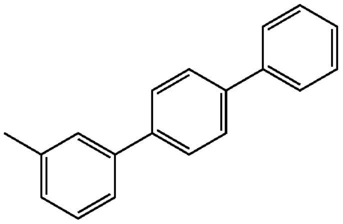

-continued
Formula (A-9)
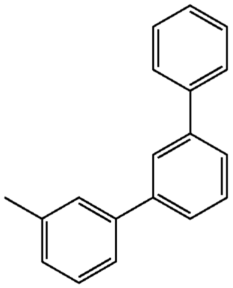
Formula (A-10)
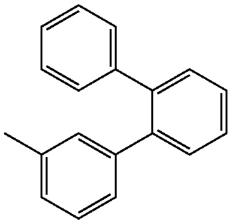
Formula (A-11)
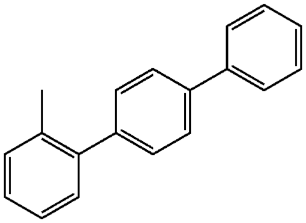
Formula (A-12)
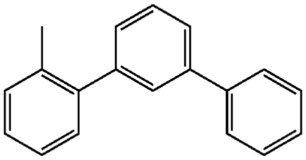
Formula (A-13)
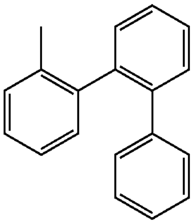
Formula (A-14)
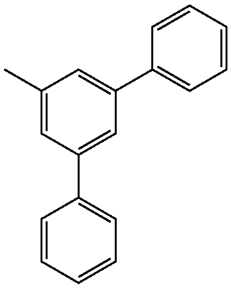
-continued
Formula (A-15)
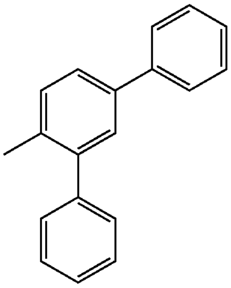
Formula (A-16)
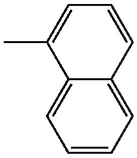
Formula (A-17)
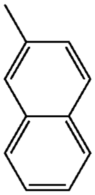
Formula (A-18)
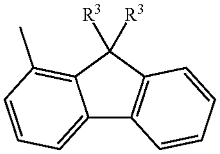
Formula (A-19)
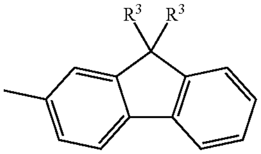
Formula (A-20)
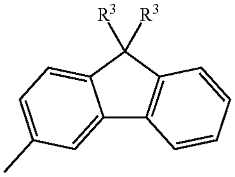
Formula (A-21)
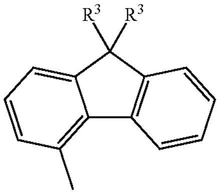
Formula (A-22)
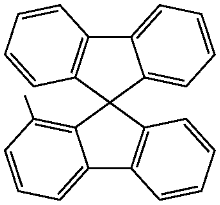

-continued

Formula (A-23)

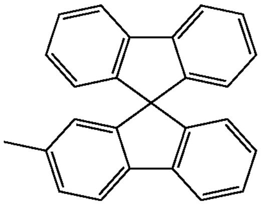

Formula (A-24)

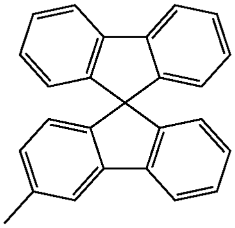

Formula (A-25)

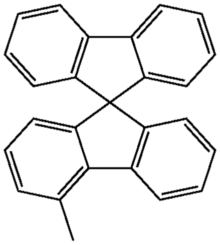

where the structures may be substituted by one or more $R^3$ radicals, and $R^3$ is as defined above. Preferably, $R^3$ here is an aliphatic radical having 1 to 20 carbon atoms, or an aromatic ring system having 6 to 24 aromatic ring atoms or a heteroaromatic ring system having 5 to 24 aromatic ring atoms, preferably an aliphatic radical having 1 to 10 carbon atoms or an aromatic ring system having 6 to 18 aromatic ring atoms.

Particularly preferred heteroaromatic ring systems $R^1$ and $R^2$ contain, as heteroaryl group, triazine, pyrimidine, pyrazine, pyridazine, pyridine, benzothiophene, benzofuran, indole, carbazole, azacarbazole, diazacarbazole, dibenzothiophene and/or dibenzofuran. The heteroaromatic ring systems here are especially selected from the structures of the following formulae (H-1) to (H-14):

Formula (H-1)

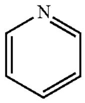

Formula (H-2)

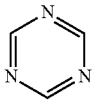

Formula (H-3)

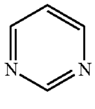

Formula (H-4)

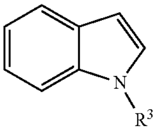

-continued

Formula (H-5)

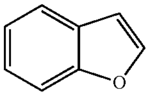

Formula (H-6)

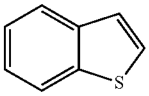

Formula (H-7)

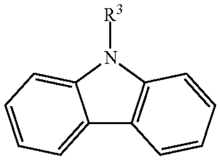

Formula (H-8)

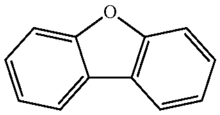

Formula (H-9)

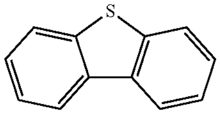

Formula (H-10)

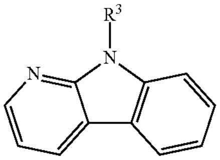

Formula (H-11)

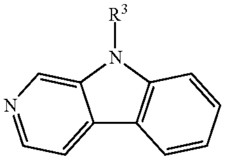

Formula (H-12)

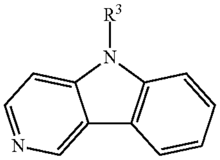

Formula (H-13)

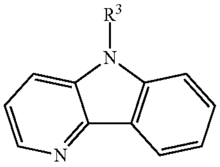

Formula (H-14)

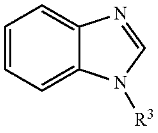

where the heteroaromatic groups may be substituted at all unoccupied positions by $R^3$ radicals and where the heteroaromatic groups may be joined to the indeno[1,2,3-jk] fluorene skeleton at any position, where the bond may also occur in place of $NR^3$ and where $R^3$ is as defined for formula (1) and the bond to the indeno[1,2,3-jk]fluorene skeleton may also be via a divalent aromatic or heteroaromatic ring system, preferably a divalent ring system of one of the formulae (Ar3-1) to (Ar3-12), more preferably of one of the formulae (Ar3-1) to (Ar3-4). Preferably, $R^3$ is an aliphatic radical having 1 to 20 carbon atoms, or an aromatic ring system having 6 to 24 aromatic ring atoms or a heteroaromatic ring system having 5 to 24 aromatic ring atoms, preferably an aliphatic radical having 1 to 10 carbon atoms or an aromatic ring system having 6 to 18 aromatic ring atoms.

When $R^1$ or $R^2$ is an $N(Ar^1)_2$ group, this group is preferably selected from the structures of the following formulae (3) and (4):

Formula (3)

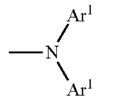

Formula (4)

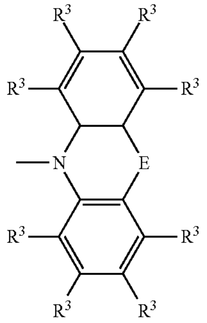

and, when $R^1$ or $R^2$ is an aromatic or heteroaromatic ring system which is a triarylamine group or a triheteroarylamine group, this group is preferably selected from the structures of the following formula (5):

Formula (5)

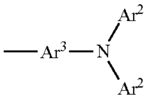

where the symbols used are as defined above, the dotted bond represents the bond to the indeno[1,2,3-jk]fluorene base skeleton and, in addition:

$Ar^2$ is the same or different at each instance and is an aromatic or heteroaromatic ring system which has 5 to 24 aromatic ring atoms and may be substituted by one or more $R^3$ radicals; the sum total of the aromatic ring atoms of all $Ar^2$ and $Ar^3$ groups together here is not greater than 60;

$Ar^3$ at each instance is an aromatic or heteroaromatic ring system which has 5 to 24 aromatic ring atoms and may be substituted by one of the plurality of $R^3$ radicals;

E is selected from the group consisting of a single bond, $C(R^3)_2$, $NR^3$, O and S.

Preferred ring systems for the formulae $Ar^1$ in formula (3) and $Ar^2$ in formula (5) are structures of the formulae (H-1) to (H-15), where these may be substituted at all unoccupied positions by $R^3$ radicals and the heteroaromatic groups may be joined to the nitrogen atom of the formula at any unoccupied position, and structures of the formulae (A-1) to (A-25), where the structures may be substituted by one or more $R^3$ radicals and the dotted bond is the bond to the nitrogen atom of the formula, and $R^3$ is as defined above.

Most preferably, at least one $Ar^2$ in formula (5) is selected from the structures (A-2) to (A-25) and (H-7) to (H-9); especially preferably, both $Ar^2$ in formula (5) are selected from the structures (A-2) to (A-25) and (H-7) to (H-9).

Most preferably, at least one $Ar^1$ in formula (3) is selected from the structures (A-2) to (A-17) and (H-7) to (H-9); especially preferably, both $Ar^2$ in formula (5) are selected from the structures (A-2) to (A-17) and (H-7) to (H-9).

Preferably, $Ar^3$ is selected from divalent groups of the following formulae (Ar3-1) to (Ar3-12):

Formula (Ar3-1)

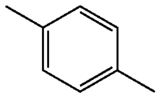

Formula (Ar3-2)

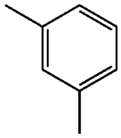

Formula (Ar3-3)

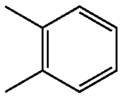

Formula (Ar3-4)

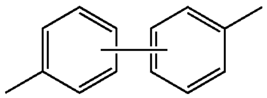

Formula (Ar3-5)

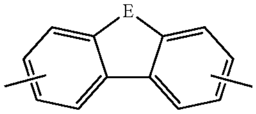

Formula (Ar3-6)

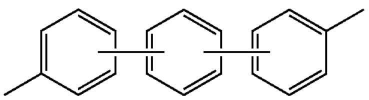

Formula (Ar3-7)

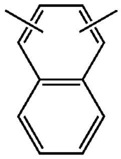

Formula (Ar3-8)

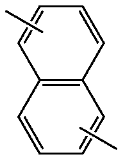

Formula (Ar3-9)

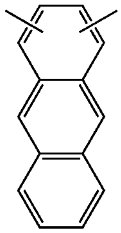

-continued

Formula (Ar3-10)

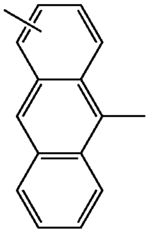

Formula (Ar3-11)

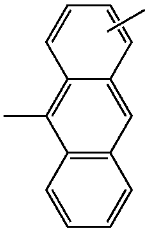

Formula (Ar3-12)

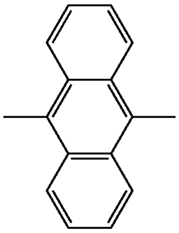

where E is the same or different at each instance and is a divalent group selected from —C($R^3$)$_2$—, —C(═O)—, —O—, —S—, —(S═O)—, —S(═O)$_2$—, —N$R^3$—, where $R^3$ is as defined for formula (1). More preferably, $Ar^3$ is one of the structures (Ar3-1) to (Ar3-4).

In a preferred embodiment, the compound comprises exactly 1, 2, 3, 4 or 5, preferably 1, 2 or 3, more preferably 1 or 2, $R^1$ and/or $R^2$ radicals selected from the formulae (3), (4) and (5), preferably from the formulae (3) and (5).

In a further embodiment, the compound contains exactly one $R^1$ or $R^2$ radical selected from the formulae (3), (4) and (5).

Preferred embodiments of the compound of formula (1) are the compounds of the formulae (1-3a) to (1-3g) and formulae (1-5a) to (1-5g):

Formula (1-3a)

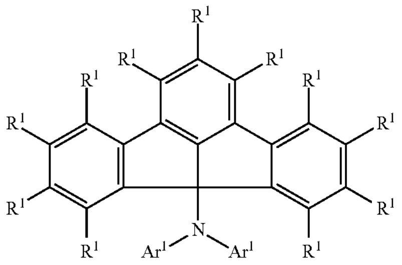

-continued

Formula (1-3b)

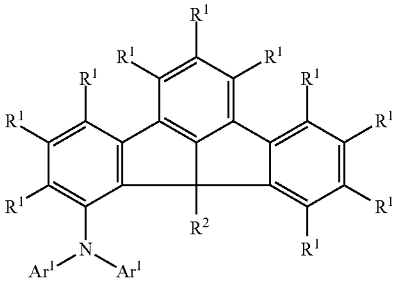

Formula (1-3c)

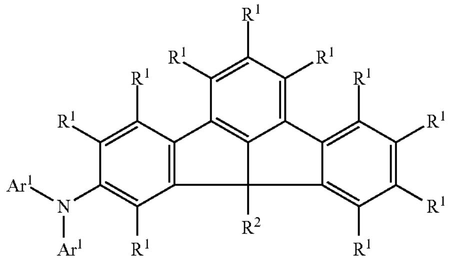

Formula (1-3d)

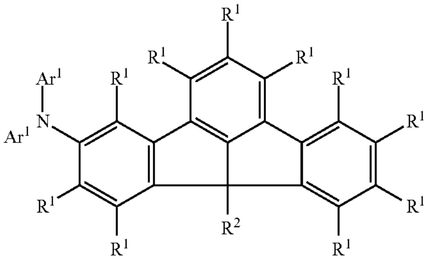

Formula (1-3e)

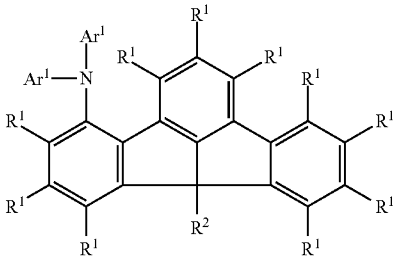

Formula (1-3f)

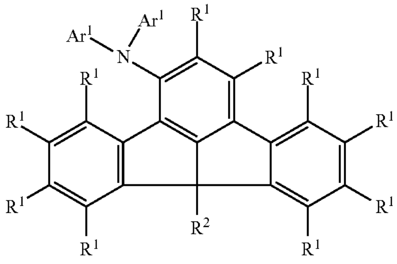

-continued

Formula (1-3g)

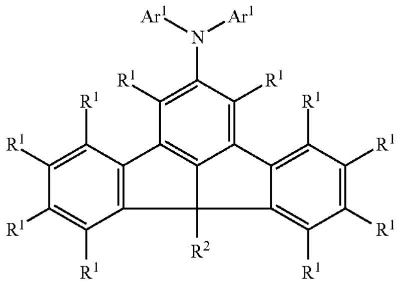

Formula (1-5a)

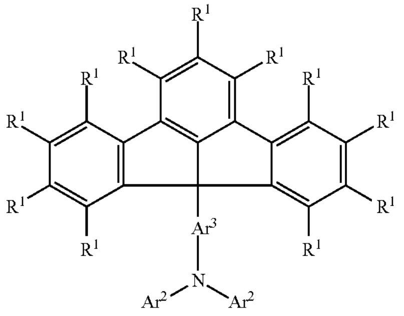

Formula (1-5b)

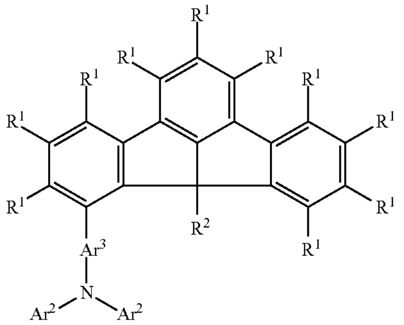

Formula (1-5c)

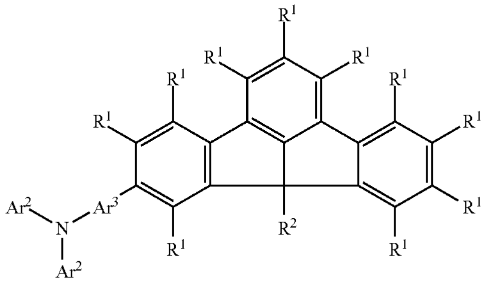

Formula (1-5d)

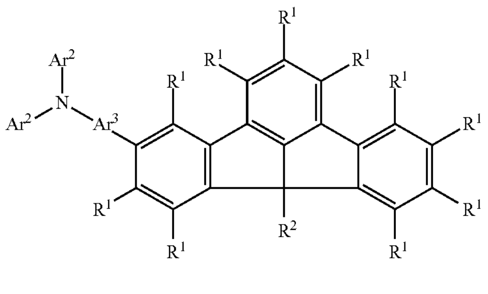

-continued

Formula (1-5e)

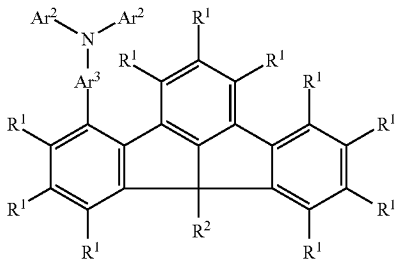

Formula (1-5f)

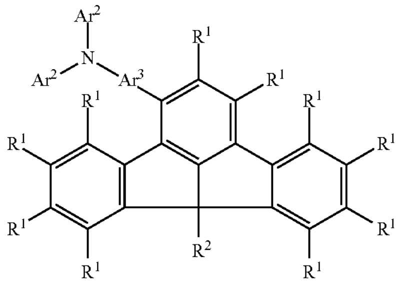

Formula (1-5g)

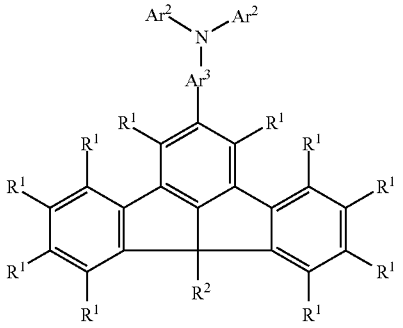

where $R^1$, $R^2$, $Ar^1$, $Ar^2$ and $Ar^3$ are as defined above.

In a preferred embodiment of the invention, in $R^2$, if present, there is no nitrogen atom, preferably heteroatom, in the para position relative to the indeno[1,2,3-jk]fluorene skeleton in a 6-membered aryl ring system directly adjoining the indeno[1,2,3-jk]fluorene skeleton. This also applies to fused aromatic ring systems containing carbazole structures bonded to the 3 position of the indeno[1,2,3-jk]fluorene skeleton. It has been found that, surprisingly, such compounds are much less stable than compounds having the nitrogen atom in the ortho or meta position.

When $R^2$ is a heteroaromatic ring system, preference is therefore given to compounds having a heteroatom, preferably nitrogen atom, in the ortho or meta position to the indeno[1,2,3-jk]fluorene skeleton.

In a preferred embodiment, when $R^2$ as a heteroaromatic ring system comprises a triarylamine group or triheteroarylamine group or a carbazole structure bonded directly to the indeno[1,2,3-jk]fluorene skeleton, the nitrogen atom is arranged in the meta or ortho position in relation to the indeno[1,2,3-jk]fluorene skeleton.

In a preferred embodiment of the invention, $Ar^3$ in formula (1-5a) is selected from the structures (Ar3-2) to (Ar3-11); preferably, the bond to the indeno[1,2,3-jk]fluorene skeleton in formula (Ar3-5) is at position 1, 2 or 4 and, in formula (Ar3-7) and (Ar3-9), not in the para position to the bond to the nitrogen. More preferably, $Ar^3$ is selected from the structures (Ar3-2) and (Ar3-3).

Therefore, a preferred embodiment of the compound of formula (1-5a) is a compound of the formulae Formula (1-5a-1)

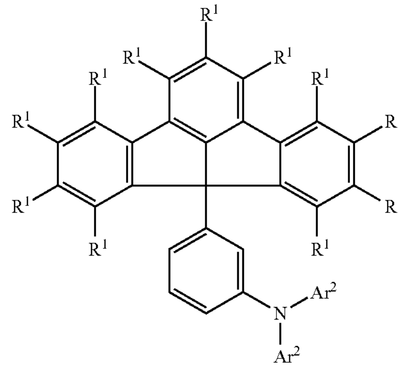

Formula (1-5a-2)

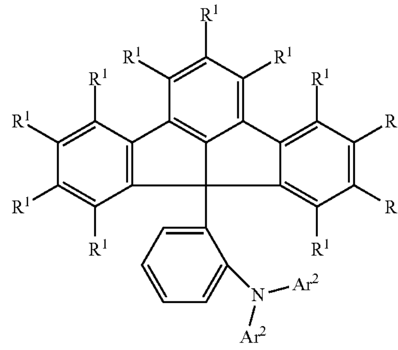

where $R^1$ and $Ar^2$ are as defined above and the compound may be substituted at the unoccupied positions by one or more $R^3$ radicals, but is preferably unsubstituted.

In a preferred embodiment of the invention, neither or exactly one of $R^1$ and $R^2$, where present, in the formulae (1-3a) to (1-3g), (1-5a) to (1-5g), or formulae (1-5a-1) and (1-5a-2), is a further group selected from the formulae (3), (4) and (5).

In a preferred embodiment of the invention, neither or exactly one of $R^1$ and $R^2$, where present, in the formulae (1-3a) to (1-3g) and (1-5a) to (1-5g), or the formulae (1-5a-1) and (1-5a-2), is a further group selected from the formulae (3), (4) and (5) and at least one further $R^1$ and/or $R^2$, if present, is an aromatic or heteroaromatic ring system, more preferably an aromatic or heteroaromatic ring system of the formulae (A-1) to (A-25) or (H-1) to (H-14), most preferably an aromatic ring system, especially of the formulae (A-1) to (A-25).

In a preferred embodiment of the invention, the more than one $R^1$ together do not form aromatic or heteroaromatic ring systems fused to the indeno[1,2,3-jk]fluorene skeleton.

According to the use of the compounds of the invention, different substituents $R^1$ and $R^2$ are selected.

When the compound of the formula (1) or (2) is used as matrix material for a phosphorescent emitter, preferably at least one $R^1$ and/or $R^2$ is $N(Ar^1)_2$, $C(=O)Ar^1$, $P(=O)(Ar^1)_2$ or an aromatic or heteroaromatic ring system which has 5 to 60 aromatic ring atoms and may be substituted by one or more $R^3$ radicals. More preferably, in this case, at least one $R^1$ and/or $R^2$ is selected from the formulae (3), (4) and (5) and the aforementioned embodiments thereof.

When the compound of the formula (1) or (2) is used as matrix material for a fluorescent emitter, preferably at least one $R^1$ and/or $R^2$ is an aromatic or heteroaromatic ring system containing at least one aryl group having at least three fused six-membered rings, preferably anthracene.

When the compound of the formula (1) or (2) is used as fluorescent emitter, preferably at least one $R^1$ and/or $R^2$ comprises an aromatic or heteroaromatic ring system containing at least one aryl group or an aromatic ring system having at least two fused six-membered rings which is preferably bonded directly or via a phenyl group to the indeno[1,2,3-jk]fluorene skeleton. This fused aryl group is preferably selected from anthracene, pyrene, phenanthrene, chrysene, monobenzoindenofluorene and dibenzoindenofluorene.

When the compounds of the formula (1) or (2) are used as electron transport material, preferably at least one $R^1$ and/or $R^2$ radical is an electron-deficient heteroaromatic ring system having 5 to 40 aromatic ring atoms, preferably having 5 to 25 aromatic ring atoms, which may be substituted by one or more $R^3$ radicals. An electron-deficient heteroaromatic ring system in the context of the present invention is a heteroaromatic ring system containing at least one electron-deficient heteroaryl group, which is either a 6-membered heteroaryl group having at least one nitrogen atom or a 5-membered heteroaryl group having at least two heteroatoms.

Particularly preferred electron-deficient heteroaromatic ring systems $R^1$ and/or $R^2$ contain, as heteroaryl group, at least one group selected from triazine, pyrimidine, pyrazine, pyridazine, pyridine, imidazole, pyrazole, oxazole, oxadiazole, triazole, thiazole, thiadiazole, benzimidazole, quinoline, isoquinoline and quinoxaline. These heteroaromatic ring systems are especially selected from the structures of the formulae (H-1), (H-2), (H-3), (H-14) where $R^3$ is as defined above and the structures are bonded to the indeno[1,2,3-jk]fluorene skeleton at an unoccupied position via a single bond or via a phenyl group.

When the compounds of the formula (1) or (2) are used as hole transport material or as emitting compound, preferably at least one $R^1$ and/or $R^2$ radical is $N(Ar^1)_2$, a triarylamino group or an electron-rich heteroaromatic ring system having 5 to 40 aromatic ring atoms, especially 5 to 25 aromatic ring atoms, which may be substituted by one or more $R^3$ radicals, especially a radical of one of the abovementioned formulae (3), (4) and (5). An electron-rich heteroaromatic ring system in the context of the invention is a heteroaromatic ring system containing at least one electron-rich heteroaryl group, which is a 5-membered heteroaryl group having exactly one heteroatom, to which one or more aryl groups may also be fused.

Particularly preferred electron-rich heteroaromatic ring systems $R^1$ and/or $R^2$ contain, as heteroaryl group, pyrrole, furan, thiophene, benzothiophene, benzofuran, indole, carbazole, dibenzothiophene, dibenzofuran and/or azacarbazole. These electron-rich heteroaromatic ring systems are especially selected from the structures of the abovementioned formulae (H-4) to (H-13).

In one embodiment of the invention, the abovementioned preferences can be combined with one another as desired.

Examples of preferred compounds as per the above-detailed embodiments, or compounds as usable with preference in electronic devices, are the compounds of the following structures (1) to (55):

-continued
1
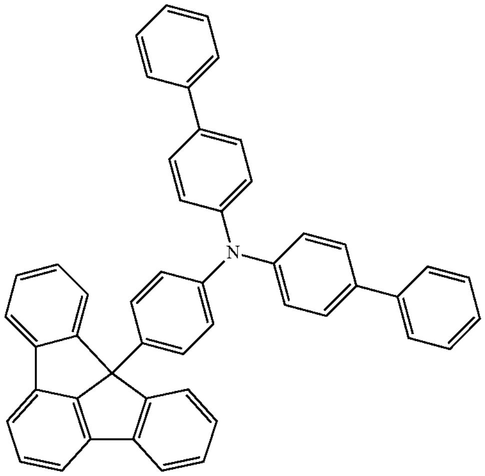
4
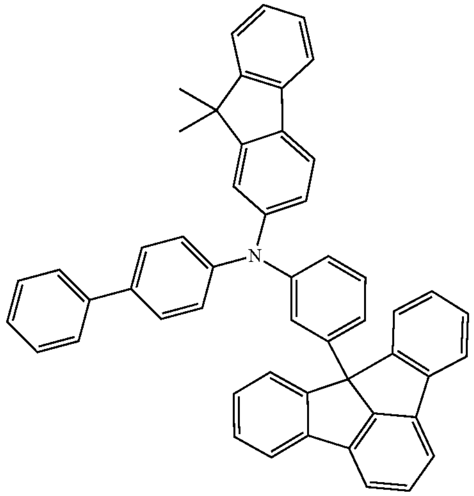
2
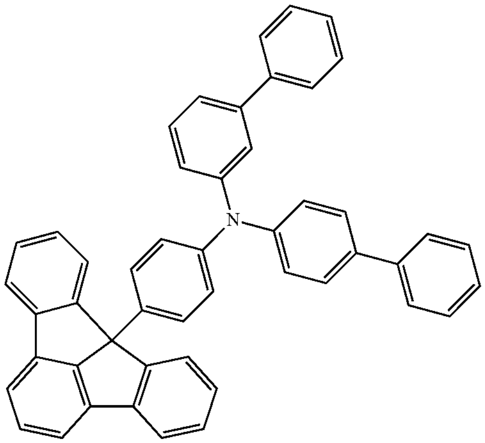
5
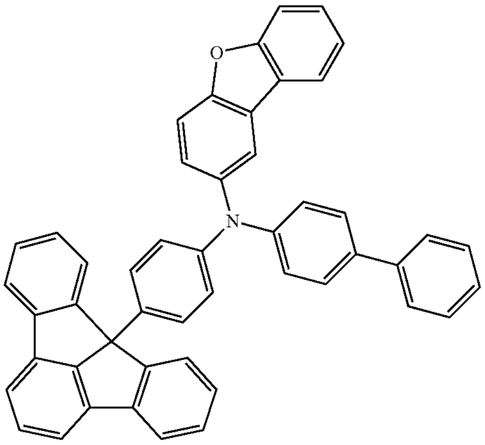
3
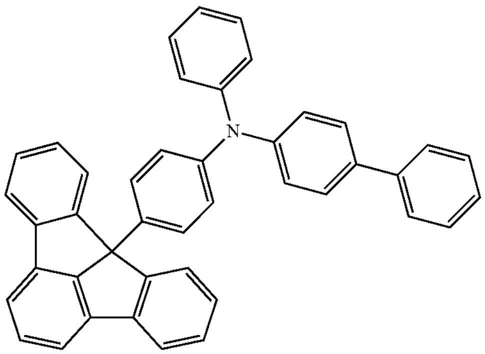
6
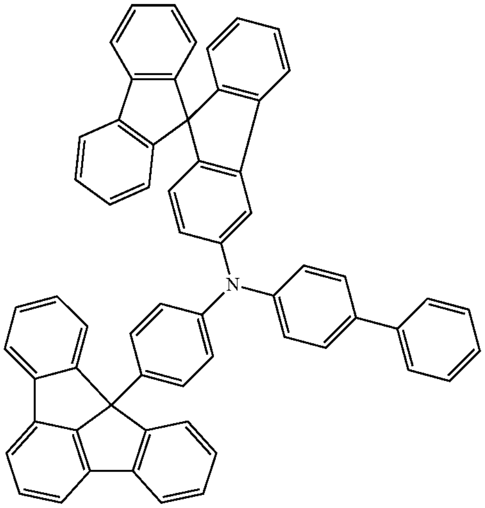

-continued
7
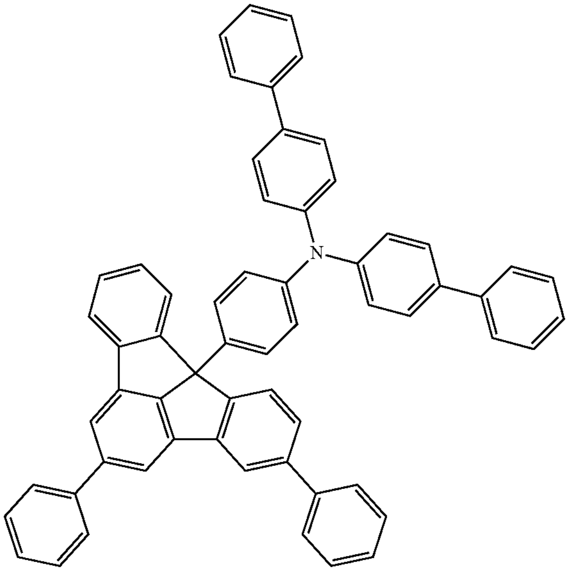
8
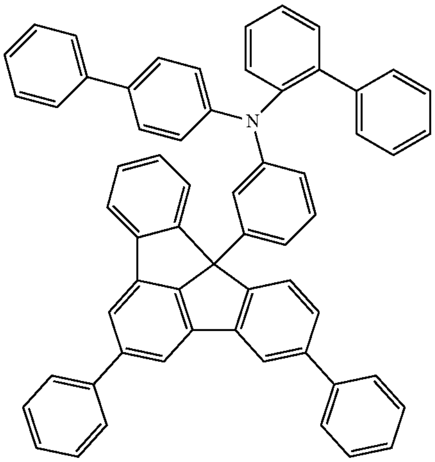
9
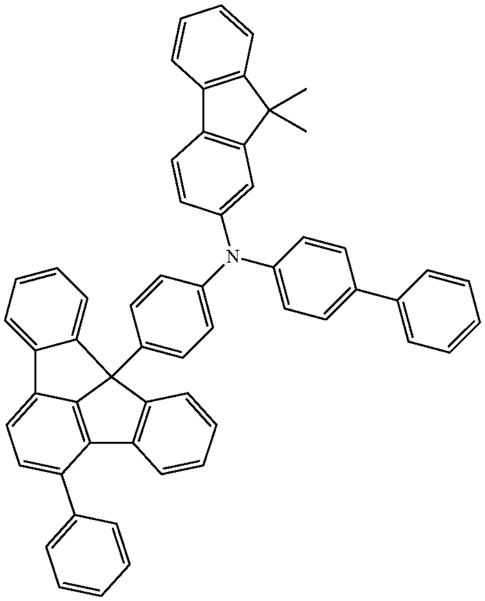
-continued
10
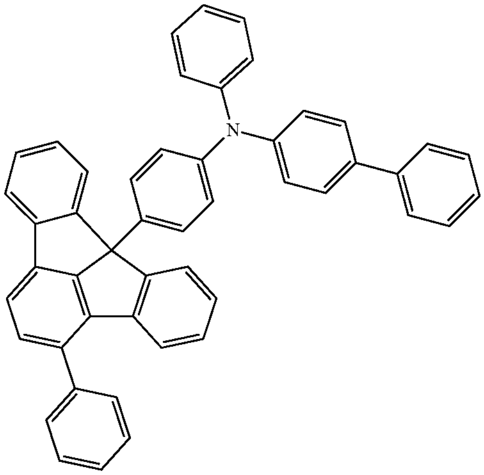
11
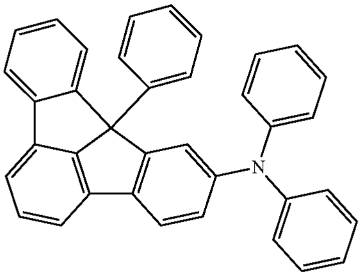
12
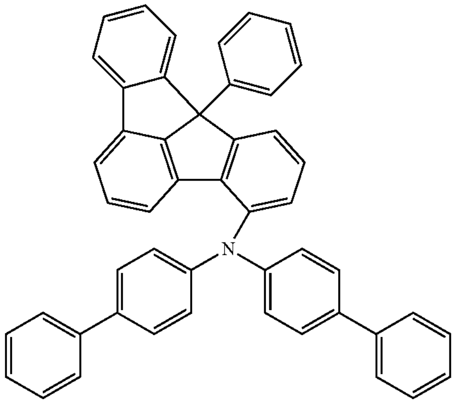
13
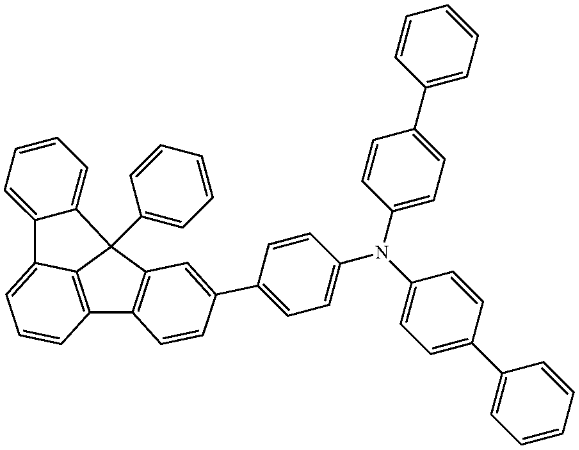

-continued
14
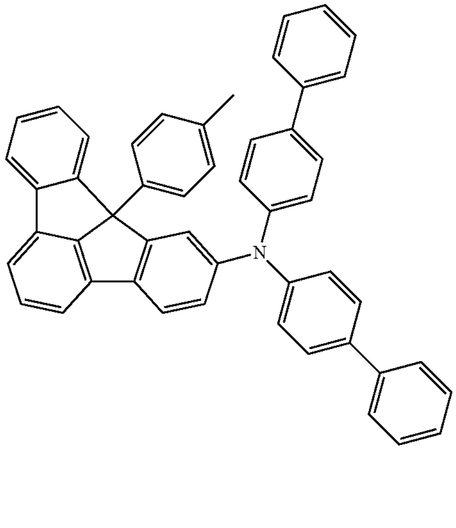
15
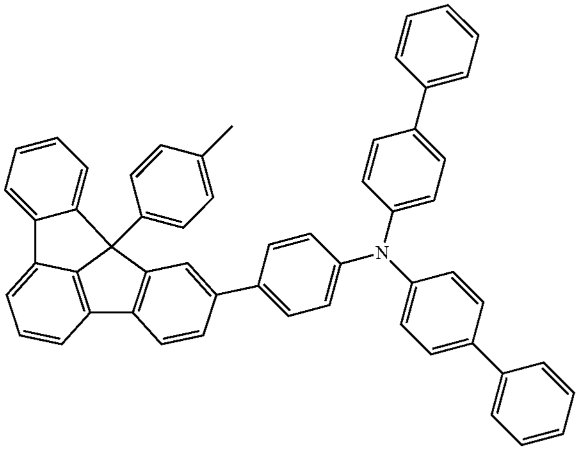
16
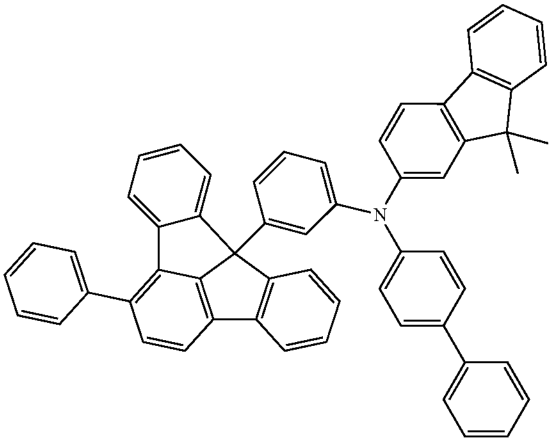
-continued
17
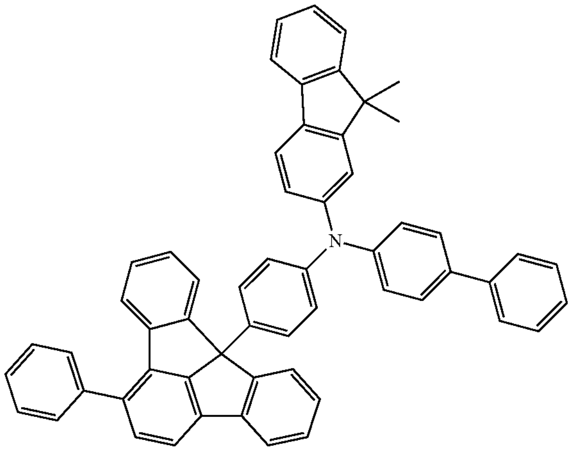
18
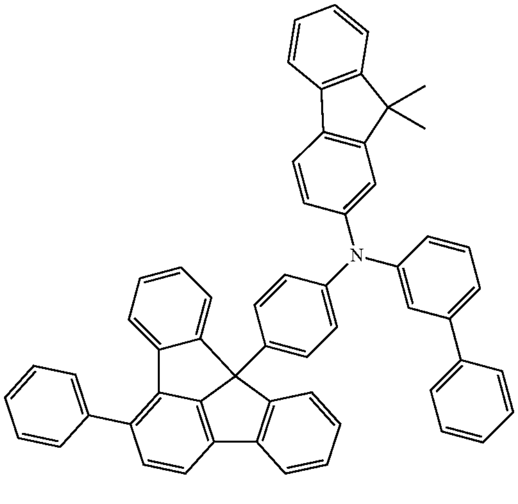
19
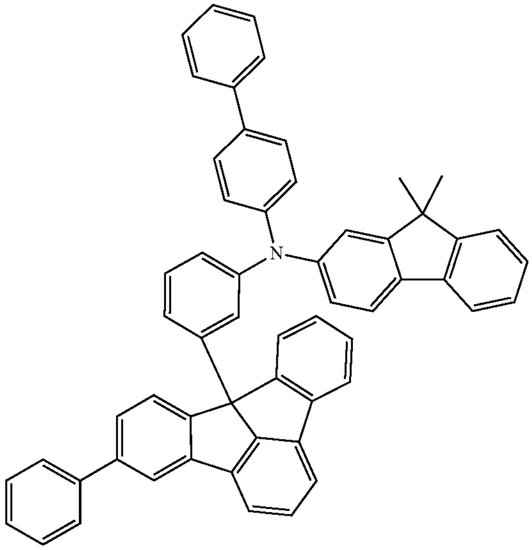

-continued
20
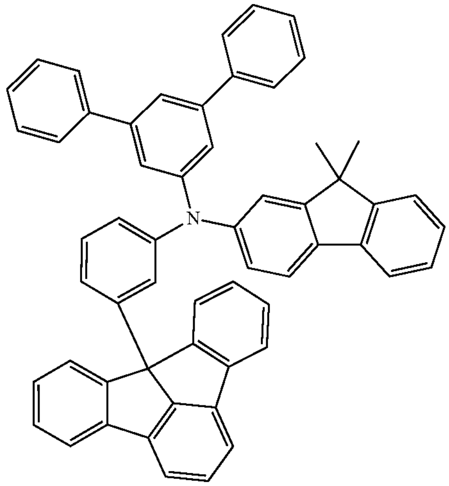
21
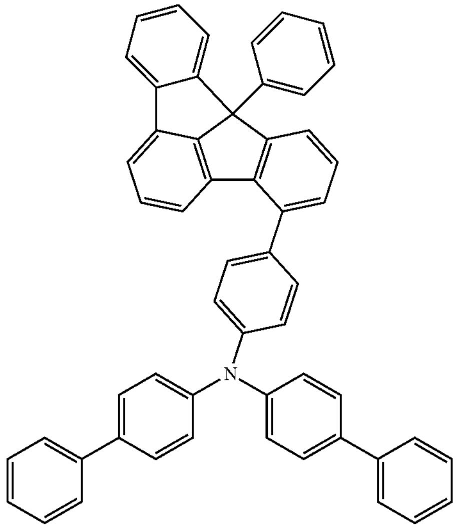
22
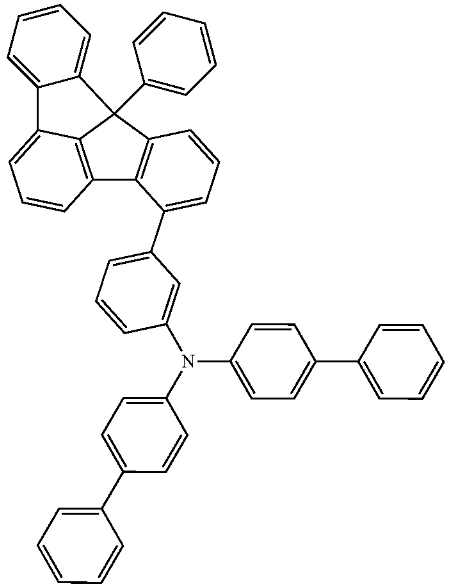
-continued
23
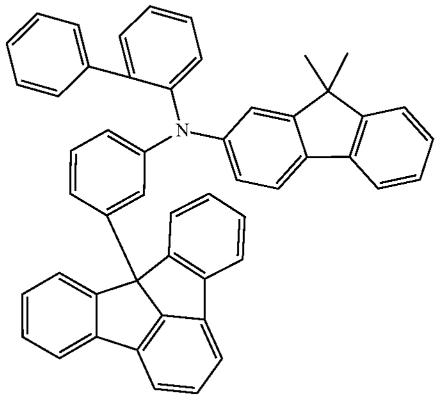
24
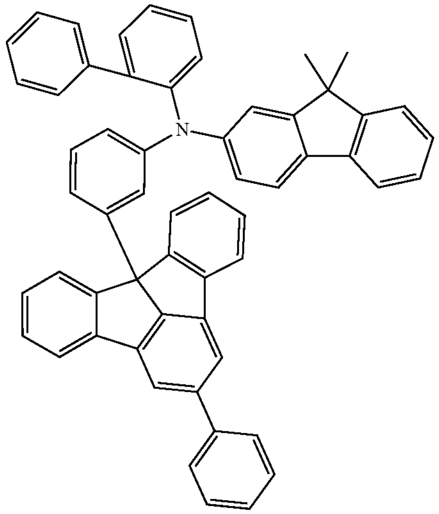
25
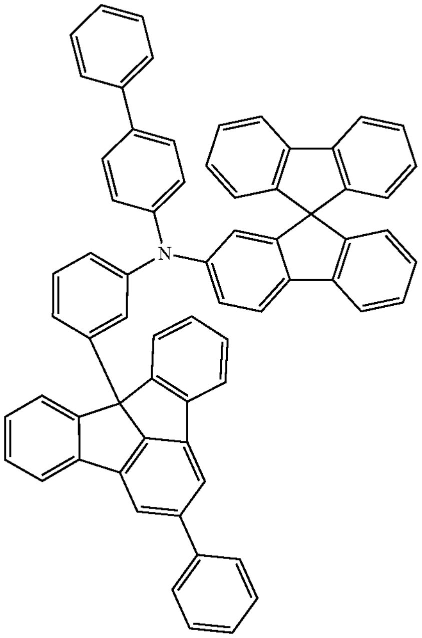

-continued
26
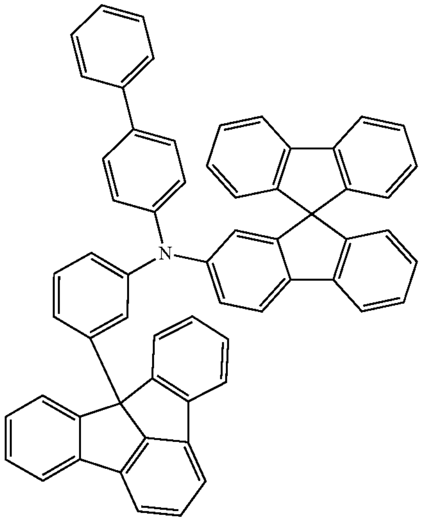
27
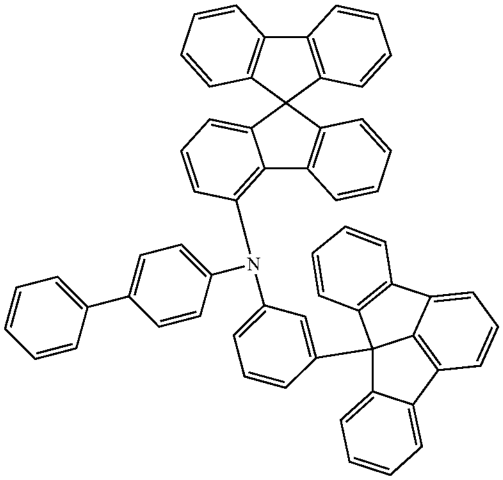
28
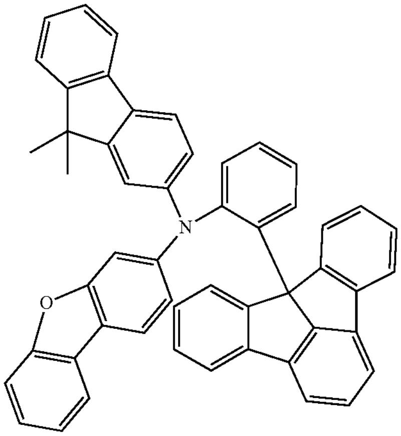
-continued
29
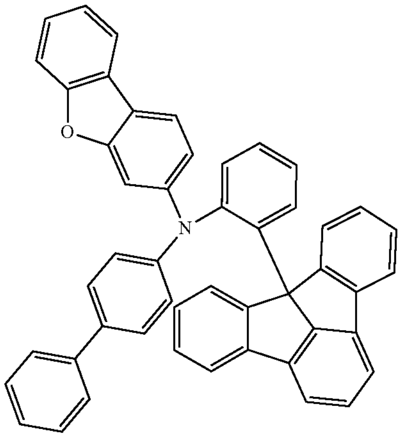
30
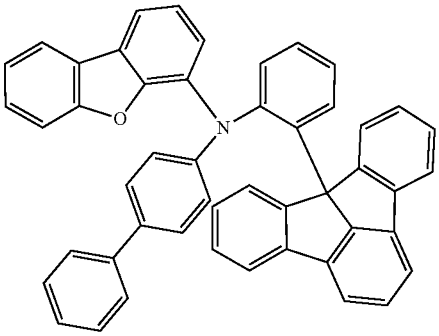
31
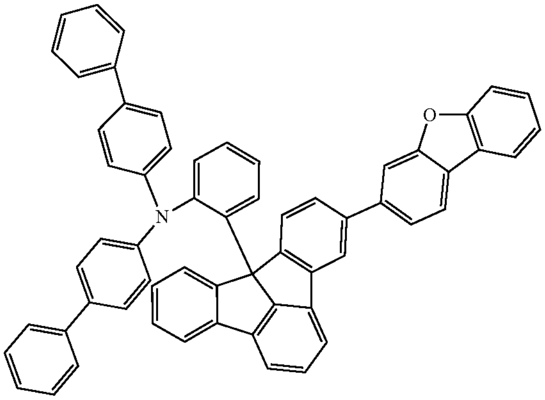
32
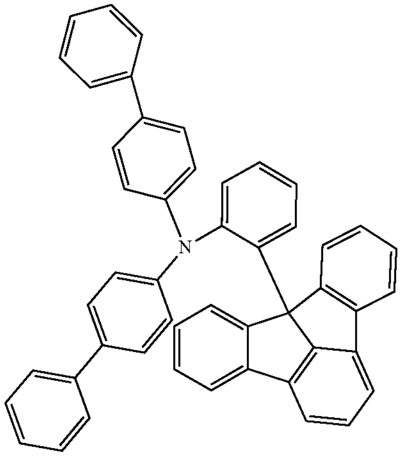

-continued
33
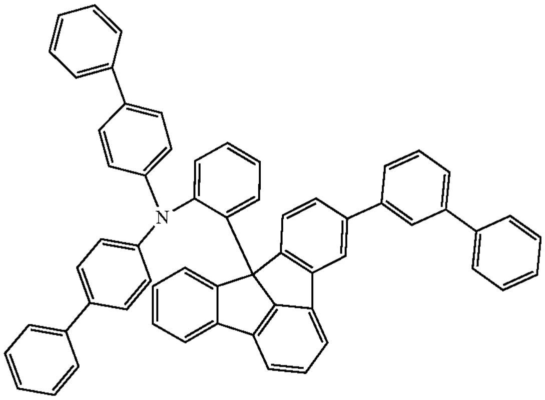
34
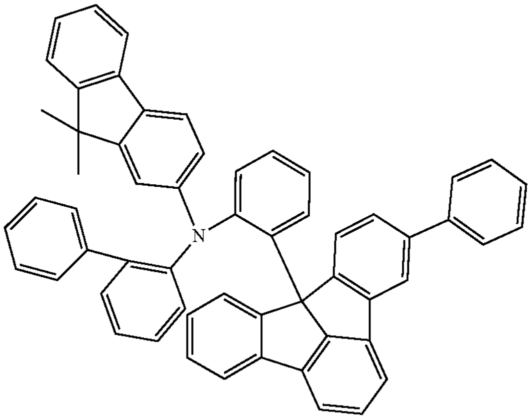
35
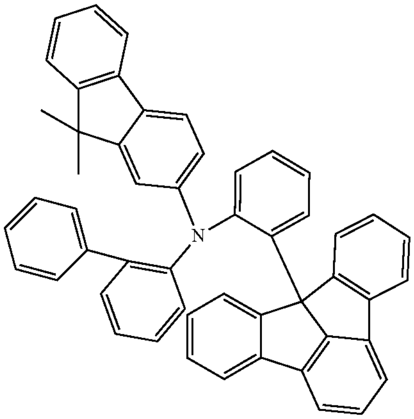
-continued
36
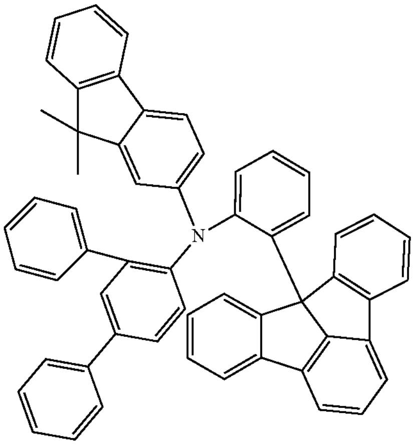
37
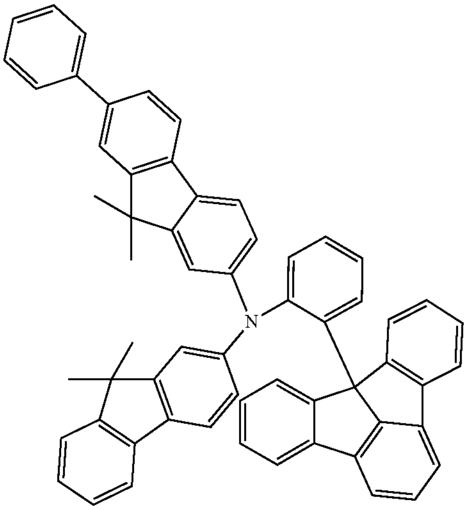
38
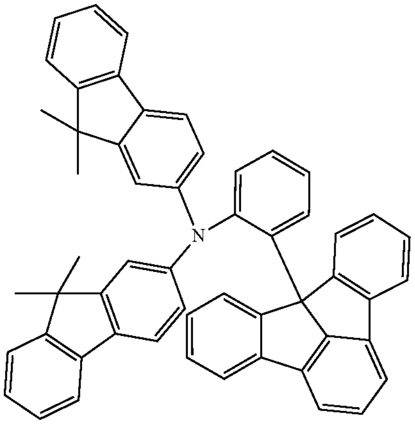

-continued
39
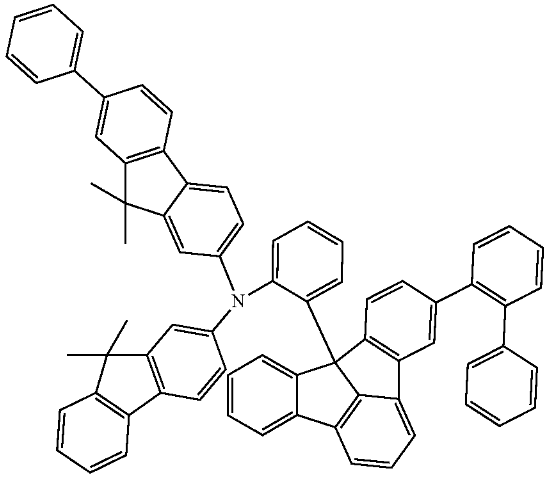
40
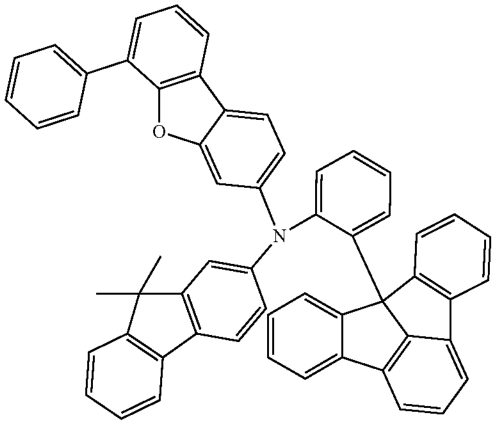
41
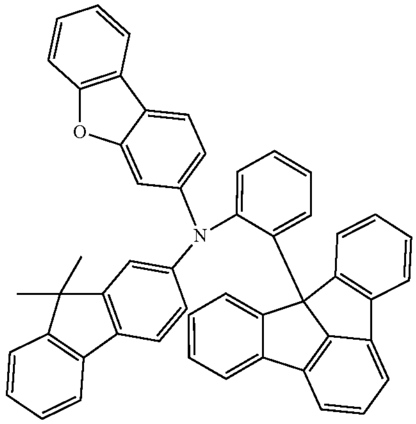
-continued
42
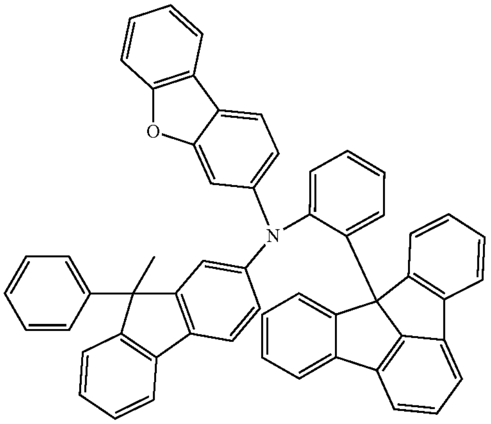
43
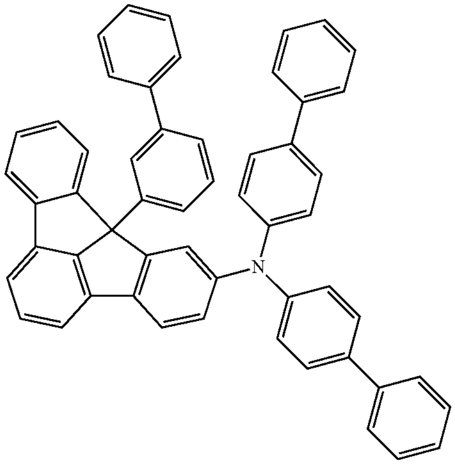
44
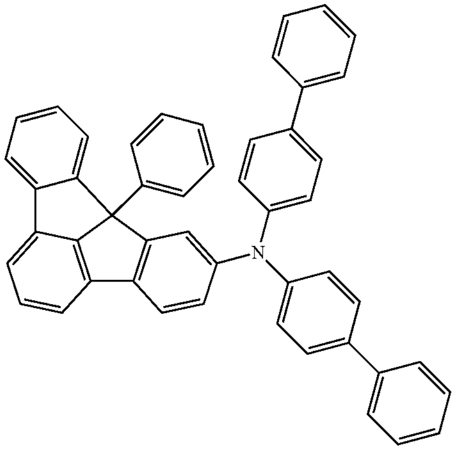

-continued
45
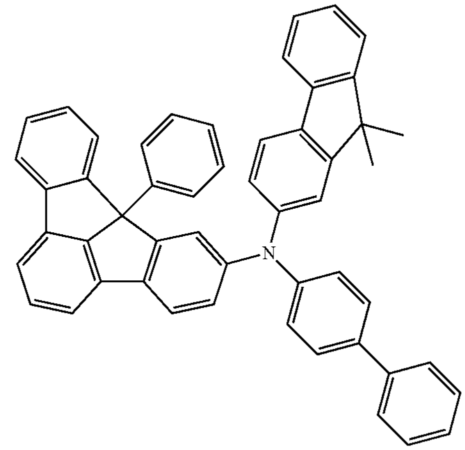
46
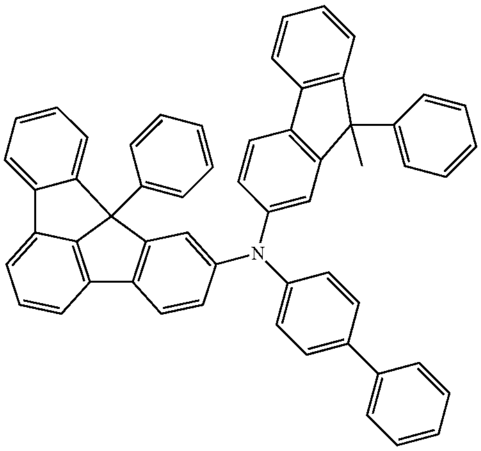
47
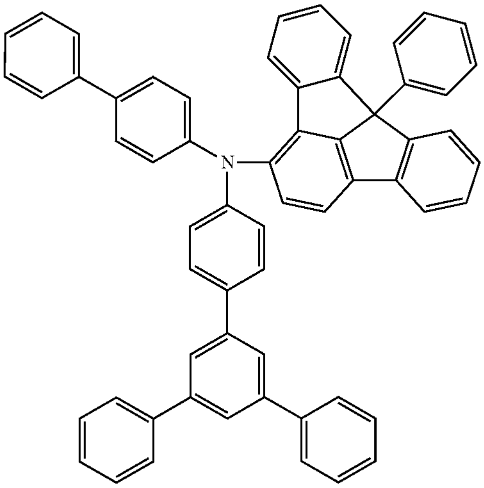
-continued
48
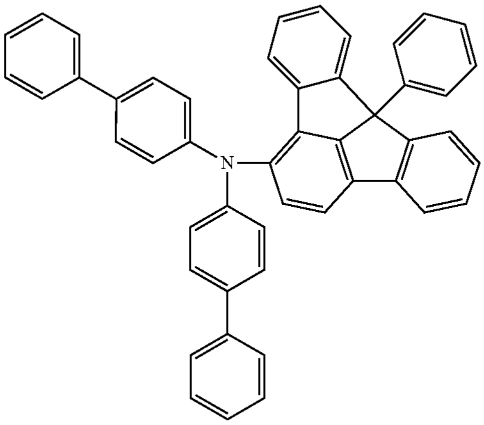
49
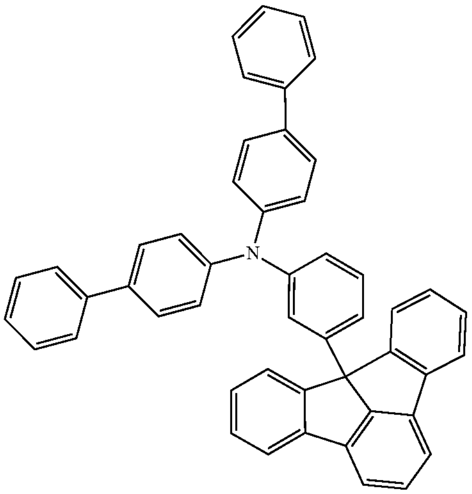
50
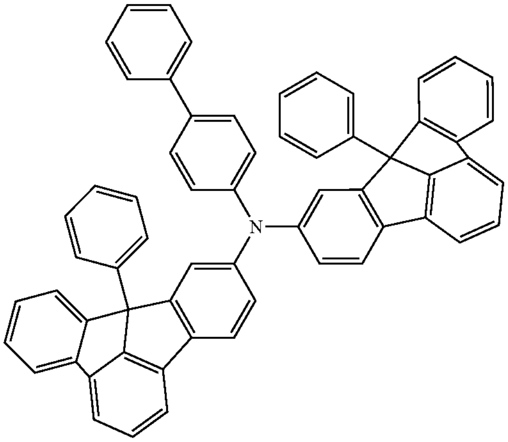

-continued

51

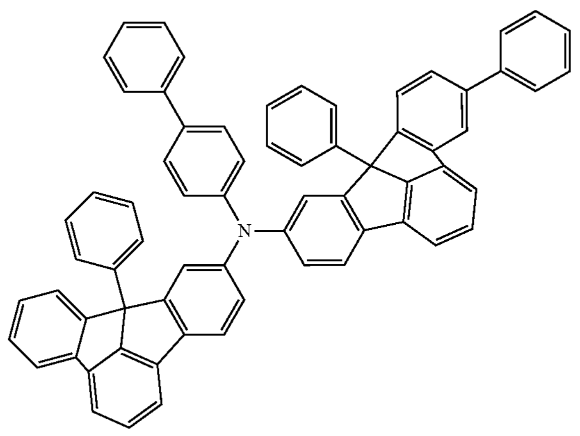

52

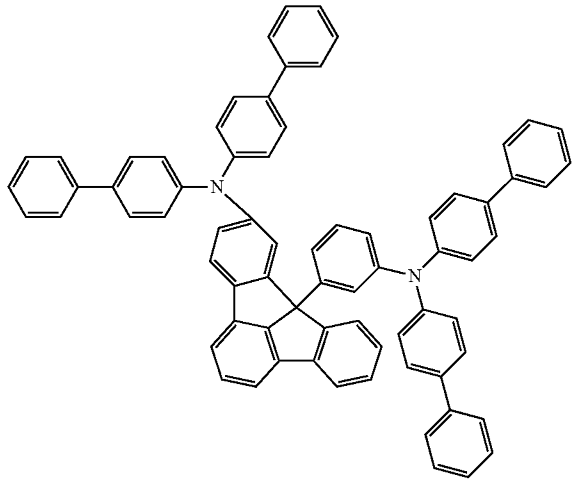

53

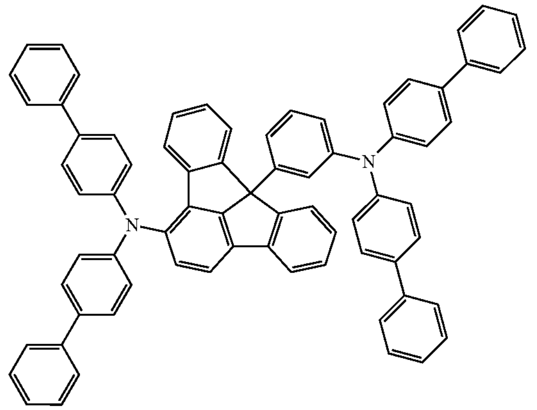

-continued

54

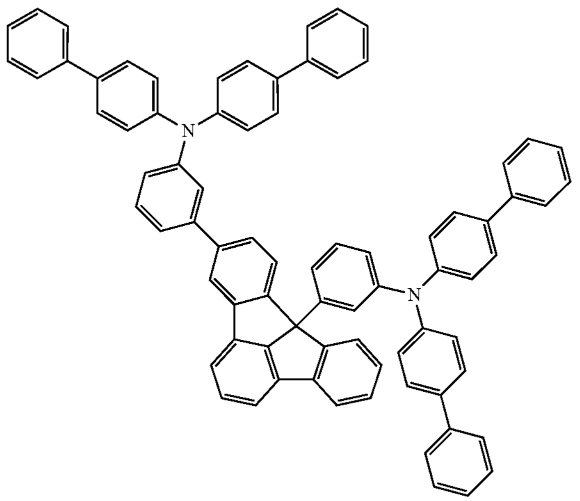

55

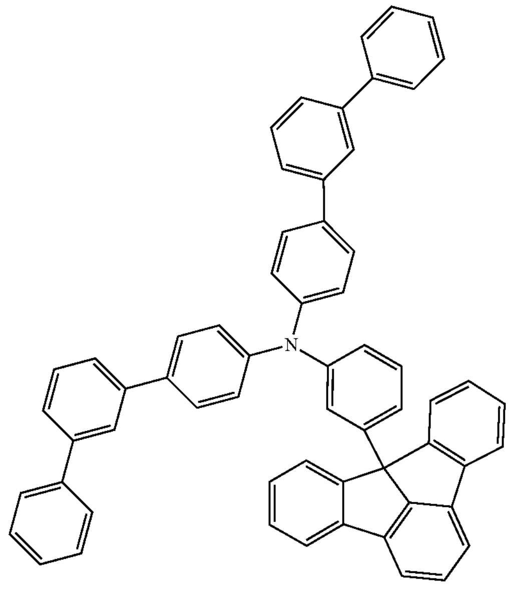

The synthesis of the compounds of the invention can be conducted by methods and reaction types known in the prior art, for example Friedel-Crafts reaction, palladium-catalyzed intramolecular C—H arylation, Buchwald coupling and Suzuki coupling and Grignard reaction.

A preferred first process for preparing the compounds of the invention proceeds from the base structures depicted as reactants in scheme 1. These are commercially available in some cases; in other cases, they can be prepared in few synthesis steps from simple, commercially available compounds:

Scheme 1

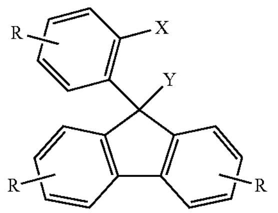

R: organic radical (if present)
X: Hal or other reactive leaving group
Y: OH, Hal or other reactive leaving group Such compounds can be obtained, for example, by reacting fluorenone with appropriately substituted aryl halide in a Grignard reaction:

Scheme 1a:

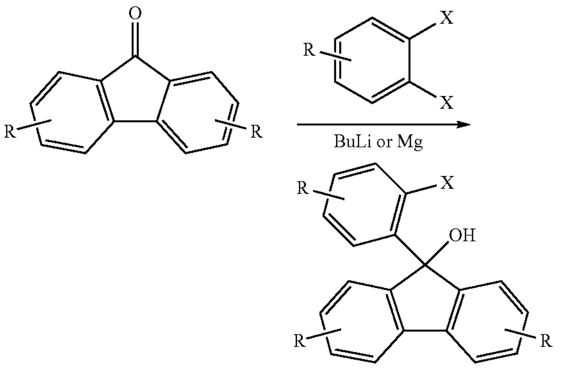

R: organic radical (if present)
X: Hal or other reactive leaving group

In a next step, the desired $R^2$ is introduced into the compound obtained in place of the Y group. When $R^2$ comprises an aromatic ring system, this is preferably accomplished via a Friedel-Crafts reaction.

Scheme 2

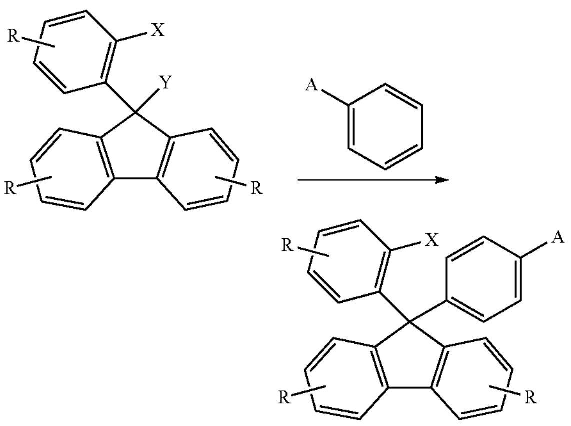

R: organic radical (if present)
X: Hal or other reactive leaving group
A: activating organic radical (if present)

Because of the Friedel-Crafts reaction, it is not possible here to introduce electron-deficient aromatic systems. In this respect, this reaction route is suitable particularly for unsubstituted or alkylated aromatics or arylamines (A is $N(Ar)_2$). At the same time, the Friedel-Crafts reaction also determines the position of any activating radical present in the para position.

In a next step, the indeno[1,2,3-jk]fluorene skeleton is constructed in an intramolecular ring closure reaction:

Scheme 3

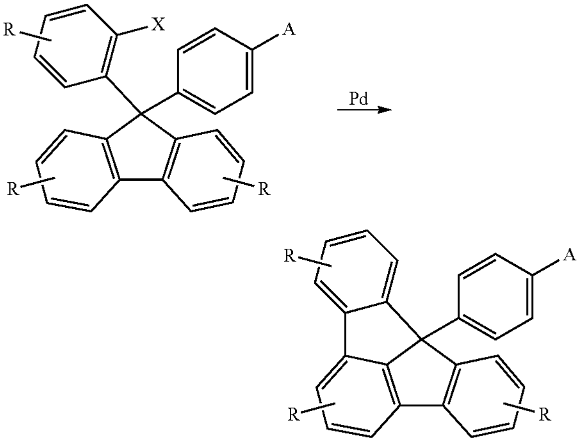

R: organic radical (if present)
X: Hal or other reactive leaving group
A: activating organic radical (if present)

A preferred second process for preparing the compounds of the invention proceeds from the benzophenone derivative depicted as reactant in scheme 4. These are commercially available in some cases; in other cases, they can be prepared in few synthesis steps from simple, commercially available compounds:

Scheme 4

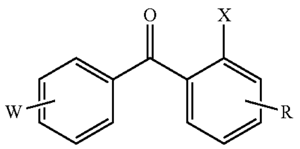

R: organic radical (if present)
W: organic radical (if present), especially $N(Ar)_2$
X: Hal or other reactive leaving group In a preferred embodiment of the second process, the starting compound is constructed by a Grignard reaction onto a CN group:

Scheme 4a

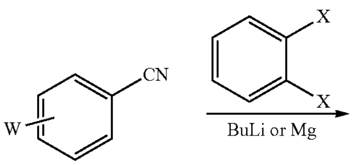

-continued

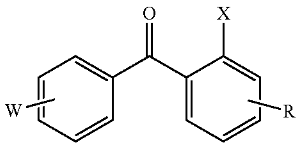

R: organic radical (if present)
W: organic radical (if present)
X: Hal or other reactive leaving group The benzonitrile compound here is the precursor compound for the later $R^2$. Several W radicals may also form rings, and also fused (annelated) rings, or together form an aromatic or heteroaromatic ring system, for example carbazoles. W is preferably an $R_2N$ group where R is preferably the same or different and is an aryl or heteroaryl group.

In a particular embodiment of the process, the W radical is an alkyl- or arylamine. The latter can be introduced via a Buchwald coupling:

Scheme 4b

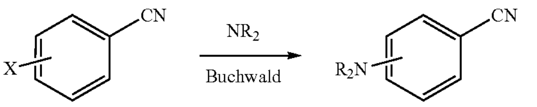

R: H or organic radical, preferably aryl or heteroaryl group
X: Hal or other reactive leaving group In a particularly preferred embodiment, the alkyl- or arylamine group is in the ortho or meta position to the nitrile group:

Scheme 4c:

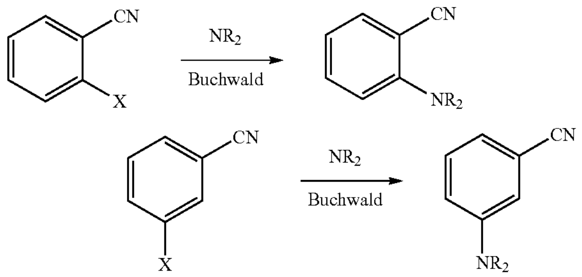

The compound from scheme 4 is reacted with a substituted biphenyl compound in a Grignard reaction:

Scheme 5

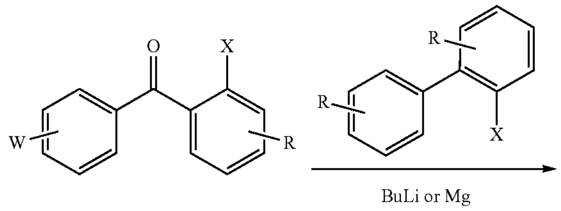

-continued

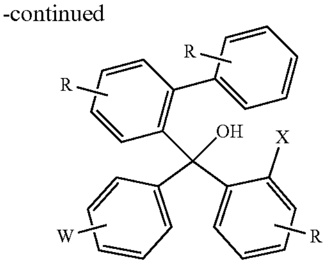

R: organic radical (if present)
W: organic radical (if present)
X: Hal or other reactive leaving group In a next step, an intramolecular electrophilic reaction is used to construct the first part of the indeno[1,2,3-jk]fluorene skeleton:

Scheme 6

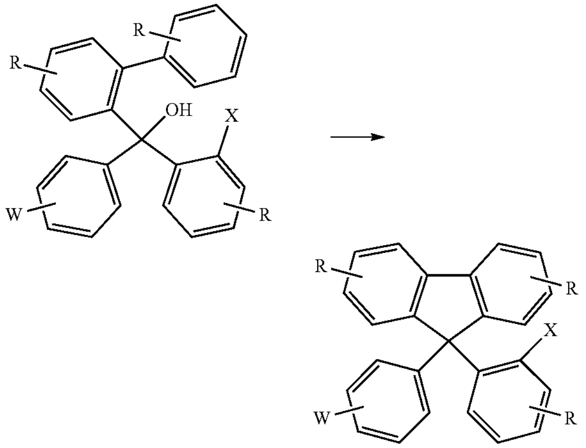

In a next step, the indeno[1,2,3-jk]fluorene skeleton is constructed in an intramolecular ring closure reaction under transition metal catalysis:

Scheme 7:

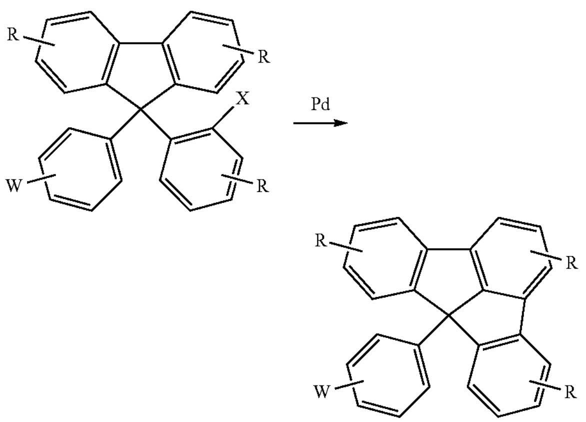

R: organic radical (if present)
W: organic radical (if present), especially $N(Ar)_2$
X: Hal or other reactive leaving group Since, in this process of the invention, the $R^2$ of the later indeno[1,2,3-jk]fluorene skeleton is not introduced via a Friedel-Crafts reaction, other substitution patterns on $R^2$ are obtainable. Particular preference is given here to groups in the meta and ortho position in relation to the indeno[1,2,3-jk]fluorene skeleton, particular preference to nitrogen substituents such as arylamines at these positions.

Scheme 8:

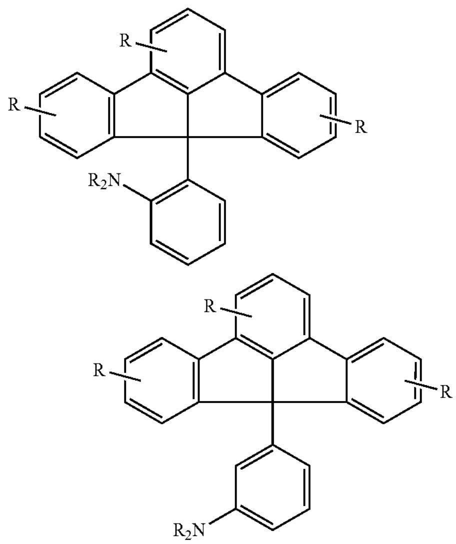

The synthesis methods shown above are of illustrative character and can be modified in a suitable manner by the person skilled in the art in the field of organic synthesis if this is advantageous for the synthesis of particular embodiments of compounds of the invention.

The present invention thus further provides a process for preparing compounds of formula (1) or (2), which is characterized in that, proceeding from a fluorenone derivative, an addition onto the keto group and a preferably transition metal-catalyzed coupling reaction for the ring closure to give the indeno[1,2,3-jk]fluorene skeleton are conducted.

The present invention thus further provides a further process for preparing compounds having an indeno[1,2,3-jk]fluorene skeleton, preferably compounds of formula (1) or (2), which is characterized in that an addition to the keto group in an aryl ketone having a leaving group in the ortho position to the keto group is conducted with a biaryl derivative and then the indeno[1,2,3-jk]fluorene skeleton is constructed via an intramolecular electrophilic reaction and a preferably transition metal-catalyzed intramolecular coupling reaction.

The above-described compounds of the invention, especially compounds substituted by reactive leaving groups, such as bromine, iodine, chlorine, boronic acid or boronic ester, may find use as monomers for production of corresponding oligomers, dendrimers or polymers. Suitable reactive leaving groups are, for example, bromine, iodine, chlorine, boronic acids, boronic esters, amines, alkenyl or alkynyl groups having a terminal C—C double bond or C—C triple bond, oxiranes, oxetanes, groups which enter into a cycloaddition, for example a 1,3-dipolar cycloaddition, for example dienes or azides, carboxylic acid derivatives, alcohols and silanes.

The invention therefore further provides oligomers, polymers or dendrimers containing one or more compounds of formula (1) or (2), wherein the bond(s) to the polymer, oligomer or dendrimer may be localized at any desired positions substituted by $R^1$ and/or $R^2$ in formula (I). According to the linkage of the compound of the invention, the compound is part of a side chain of the oligomer or polymer or part of the main chain.

An oligomer in the context of the invention is understood to mean a compound formed from at least three monomer units. A polymer in the context of this invention is understood to mean a compound formed from at least ten monomer units.

The polymers, oligomers or dendrimers of the invention may be conjugated, partly conjugated or nonconjugated. The oligomers or polymers of the invention may be linear, branched or dendritic.

In the structures having linear linkage, the units of formula (1) or (2) may be joined directly to one another, or they may be joined to one another via a bivalent group, for example via a substituted or unsubstituted alkylene group, via a heteroatom or via a bivalent aromatic or heteroaromatic group.

In branched and dendritic structures, it is possible, for example, for 3, 5 or more units of formula (1) or (2) to be joined via a trivalent or higher-valency group, for example via a trivalent or higher-valency aromatic or heteroaromatic group, to give a branched or dendritic oligomer or polymer.

For the repeat units of formula (1) or (2) in oligomers, dendrimers and polymers, the same preferences apply as described above for the compounds of the invention.

In one embodiment of the invention, the bonds to the oligomer, polymer or dendrimer are not localized at the two positions 5 and 10.

For preparation of the oligomers or polymers, the monomers of the invention are homopolymerized or copolymerized with further monomers. Suitable and preferred comonomers are chosen from fluorenes (for example according to EP 842208 or WO 2000/22026), spirobifluorenes (for example according to EP 707020, EP 894107 or WO 2006/061181), paraphenylenes (for example according to WO 1992/18552), carbazoles (for example according to WO 2004/070772 or WO 2004/113468), thiophenes (for example according to EP 1028136), dihydrophenanthrenes (for example according to WO 2005/014689 or WO 2007/006383), cis- and trans-indenofluorenes (for example according to WO 2004/041901 or WO 2004/113412), ketones (for example according to WO2005/040302), phenanthrenes (for example according to WO 2005/104264 or WO 2007/017066) or else a plurality of these units. The polymers, oligomers and dendrimers typically contain still further units, for example emitting (fluorescent or phosphorescent) units, for example vinyltriarylamines (for example according to WO 2007/068325) or phosphorescent metal complexes (for example according to WO 2006/003000), and/or charge transport units, especially those based on triarylamines.

The polymers, oligomers and dendrimers of the invention have advantageous properties, especially high lifetimes, high efficiencies and good color coordinates.

The polymers and oligomers of the invention are generally prepared by polymerization of one or more monomer types, of which at least one monomer leads to repeat units of the formula (1) or (2) in the polymer. Suitable polymerization reactions are known to those skilled in the art and are described in the literature. Particularly suitable and preferred polymerization reactions which lead to C—C and C—N bonds are as follows:

(A) SUZUKI polymerization;

(B) YAMAMOTO polymerization;

(C) STILLE polymerization; and (D) HARTWIG-BUCHWALD polymerization.

How the polymerization can be conducted by these methods and how the polymers can then be separated from the reaction medium and purified is known to those skilled in the art and is described in detail in the literature, for example in WO 2003/048225, WO 2004/037887 and WO 2004/037887.

The present invention thus also provides a process for preparing the polymers, oligomers and dendrimers of the invention, which is characterized in that they are prepared by polymerization according to SUZUKI, polymerization according to YAMAMOTO, polymerization according to STILLE or polymerization according to HARTWIG-BUCHWALD. The dendrimers of the invention can be prepared by processes known to those skilled in the art or in analogy thereto. Suitable processes are described in the literature, for example in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6; WO 2002/067343 A1 and WO 2005/026144 A1.

For the processing of the compounds of the invention from the liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore further provides a formulation, especially a solution, dispersion or emulsion, comprising at least one compound of formula (1) or (2) or at least one polymer, oligomer or dendrimer containing at least one unit of formula (1) or (2) and at least one solvent, preferably an organic solvent. The way in which such solutions can be prepared is known to those skilled in the art and is described, for example, in WO 2002/072714, WO 2003/019694 and the literature cited therein.

The compounds of formula (1) or (2) are suitable for use in electronic devices, especially in organic electroluminescent devices (OLEDs). Depending on the substitution, the compounds are used in different functions and in different layers of the organic electroluminescent device. Preferably, the compounds are used as hole transport materials in a hole transport or hole injection layer, as matrix materials in an emitting layer, as electron blocker materials, as exciton blocker materials and/or as materials for an interlayer.

The invention therefore further provides for the use of the compounds of formula (1) or (2) in electronic devices, and electronic devices comprising one or more compounds of formula (1) or (2) themselves. These electronic devices are preferably selected from the group consisting of organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and more preferably selected from organic electroluminescent devices (OLEDs). Particular preference is given to organic electroluminescent devices comprising anode, cathode and at least one emitting layer, characterized in that at least one organic layer, which may be an emitting layer, a hole transport layer or another layer, comprises at least one compound of formula (1) or (2).

Apart from the cathode, anode and emitting layer, the organic electroluminescent device may also comprise further layers. These are selected, for example, from in each case one or more hole injection layers, hole transport layers, hole blocker layers, electron transport layers, electron injection layers, electron blocker layers, exciton blocker layers, interlayers, charge generation layers (IDMC 2003, Taiwan; Session 21 OLED (5), T. Matsumoto, T. Nakada, J. Endo, K. Mori, N. Kawamura, A. Yokoi, J. Kido, Multiphoton Organic EL Device Having Charge Generation Layer) and/or organic or inorganic p/n junctions. However, it should be pointed out that not every one of these layers need necessarily be present and the choice of layers always depends on the compounds used and especially also on whether the device is a fluorescent or phosphorescent electroluminescent device.

The organic electroluminescent device may also comprise several emitting layers. More preferably, these emission layers in this case have several emission maxima between 380 nm and 750 nm overall, such that the overall result is white emission; in other words, various emitting compounds which may fluoresce or phosphoresce and which emit blue, yellow, green, orange or red light are used in the emitting layers. Especially preferred are three-layer systems, i.e. systems having three emitting layers, where at least one of these layers comprises at least one compound of formula (1) or (2) and where the three layers show blue, green and orange or red emission (for the basic construction see, for example, WO 2005/011013). Alternatively and/or additionally, the compounds of the invention may also be present in the hole transport layer and/or in an interlayer. It should be noted that, for the production of white light, rather than a plurality of color-emitting emitter compounds, an emitter compound used individually which emits over a broad wavelength range may also be suitable.

It is preferable in accordance with the invention when the compound of formula (1) or (2) is used in an electronic device comprising one or more phosphorescent dopants. In this case, the compound may be used in different layers, preferably in a hole transport layer, a hole injection layer or an emitting layer. It is also possible in accordance with the invention to use the compound of formula (1) or (2) in an electronic device comprising one or more fluorescent dopants.

The term "phosphorescent dopants" typically encompasses compounds where the emission of light is effected through a spin-forbidden transition, for example a transition from an excited triplet state or a state having a higher spin quantum number, for example a quintet state.

Suitable phosphorescent dopants (=triplet emitters) are especially compounds which, when suitably excited, emit light, preferably in the visible region, and also contain at least one atom of atomic number greater than 20, preferably greater than 38, and less than 84, more preferably greater than 56 and less than 80. Preferred phosphorescence emitters used are compounds containing copper, molybdenum, tungsten, rhenium, ruthenium, osmium, rhodium, iridium, palladium, platinum, silver, gold or europium, especially compounds containing iridium, platinum or copper.

In the context of the present invention, all luminescent iridium, platinum or copper complexes are considered to be phosphorescent compounds.

Examples of the above-described emitters can be found in applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as used for phosphorescent OLEDs according to the prior art and as known to those skilled in the art in the field of organic electroluminescent devices are suitable. It is also possible for the person skilled in the art, without exercising inventive skill, to use further phosphorescent complexes in combination with the compounds of formula (1) or (2) in organic electroluminescent devices.

Explicit examples of suitable phosphorescent emitter compounds can also be found in a table of phosphorescent dopants shown below.

In a preferred embodiment of the invention, the compounds of formula (1) or (2) are used as hole transport material. In that case, the compounds are preferably used in a hole transport layer and/or in a hole injection layer.

A hole injection layer in the context of this invention is a layer directly adjoining the anode. A hole transport layer in the context of this invention is a layer between the hole injection layer and the emission layer. The hole transport layer may directly adjoin the emission layer. When the compounds of formula (1) or (2) are used as hole transport material or as hole injection material, it may be preferable when they are doped with electron acceptor compounds, for example with $F_4$-TCNQ or with compounds as described in EP 1476881 or EP 1596445. In a further preferred embodiment of the invention, a compound of formula (1) or (2) is used as hole transport material in combination with a hexaazatriphenylene derivative as described in US 2007/0092755. Particular preference is given here to using the hexaazatriphenylene derivative in a separate layer.

If the compound of formula (1) or (2) is used as hole transport material in a hole transport layer, the compound can be used as pure material, i.e. in a proportion of 100%, in the hole transport layer, or it can be used in the hole transport layer in combination with one or more further compounds.

In a further embodiment of the present invention, the compounds of the formula (1) or (2) are used as matrix material in combination with one or more dopants, preferably phosphorescent dopants.

A dopant in a system comprising a matrix material and a dopant is understood to mean that component having the smaller proportion in the mixture. Correspondingly, a matrix material in a system comprising a matrix material and a dopant is understood to mean that component having the greater proportion in the mixture.

The proportion of the matrix material in the emitting layer in this case is between 50.0% and 99.9% by volume, preferably between 80.0% and 99.5% by volume, and more preferably between 92.0% and 99.5% by volume for fluorescent emitting layers and between 85.0% and 97.0% by volume for phosphorescent emitting layers.

Correspondingly, the proportion of the dopant is between 0.1% and 50.0% by volume, preferably between 0.5% and 20.0% by volume, and more preferably between 0.5% and 8.0% by volume for fluorescent emitting layers and between 3.0% and 15.0% by volume for phosphorescent emitting layers.

An emitting layer of an organic electroluminescent device may also comprise systems comprising a plurality of matrix materials (mixed matrix system) and/or a plurality of dopants. In this case too, the dopants are generally those materials having the smaller proportion in the system and the matrix materials are those materials having the greater proportion in the system. In individual cases, however, the proportion of a single matrix material in the system may be less than the proportion of a single dopant.

In a preferred embodiment of the invention, the compounds of formula (1) or (2) are used as a component of mixed matrix systems. The mixed matrix systems preferably comprise two or three different matrix materials, more preferably two different matrix materials. The two different matrix materials may be present in a ratio of 1:10 to 1:1, preferably in a ratio of 1:4 to 1:1.

The mixed matrix systems may comprise one or more dopants. According to the invention, the dopant compound(s) together have a proportion of 0.1% to 50.0% by volume of the overall mixture and preferably a proportion of 0.5% to 20.0% by volume of the overall mixture. Correspondingly, the matrix components together have a proportion of 50.0% to 99.9% by volume of the overall mixture and preferably a proportion of 80.0% to 99.5% by volume of the overall mixture.

Preference is given to using mixed matrix systems in phosphorescent organic electroluminescent devices.

Particularly suitable matrix materials which can be used in combination with the compounds of the invention as matrix components of a mixed matrix system are aromatic ketones, aromatic phosphine oxides or aromatic sulfoxides or sulfones, for example according to WO 04/013080, WO 04/093207, WO 06/005627 or WO 10/006680, triarylamines, carbazole derivatives, e.g. CBP (N,N-biscarbazolylbiphenyl) or the carbazole derivatives disclosed in WO 05/039246, US 2005/0069729, JP 2004/288381, EP 1205527 or WO 08/086851, indolocarbazole derivatives, for example according to WO 07/063754 or WO 08/056746, azacarbazole derivatives, for example according to EP 1617710, EP 1617711, EP 1731584, JP 2005/347160, bipolar matrix materials, for example according to WO 07/137725, silanes, for example according to WO 05/111172, azaboroles or boronic esters, for example according to WO 06/117052, triazine derivatives, for example according to the application WO 2010/015306, WO 2007/063754 or WO 2008/056746, zinc complexes, for example according to EP 652273 or WO 09/062578, diazasilole or tetraazasilole derivatives, for example according to WO 10/054729, diazaphosphole derivatives, for example according to WO 10/054730, or indenocarbazole derivatives, for example according to WO 10/136109.

Preferred phosphorescent dopants for use in mixed matrix systems comprising the compounds of the invention are the phosphorescent dopants listed in a table which follows.

In a further preferred embodiment of the invention, the compounds of formula (1) or (2) are used in an interlayer. Interlayers are preferably used in organic electroluminescent devices comprising a plurality of emitting layers, for example in white-emitting OLEDs having one red-emitting, one green-emitting and one blue-emitting layer. More preferably, interlayers are arranged between two emitting layers. An interlayer comprising a compound of the invention, in a preferred embodiment of the invention, is arranged between the blue-emitting layer and the green-emitting layer of a white light-emitting OLED comprising a red-emitting layer, a green-emitting layer and a blue-emitting layer. More preferably, the blue-emitting layer is a fluorescent layer, and the green-emitting layer is a phosphorescent layer.

The compounds listed in the table which follows are particularly suitable phosphorescent emitters.

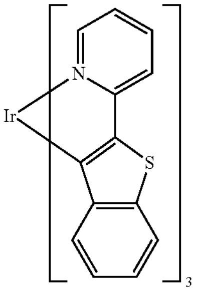

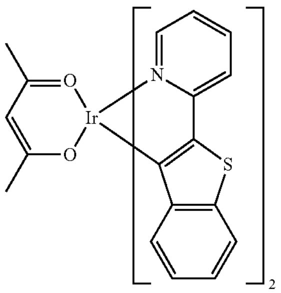

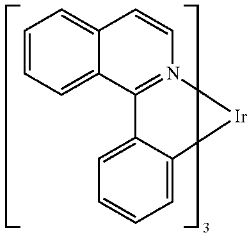

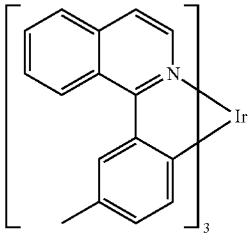

-continued

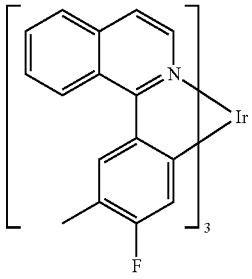

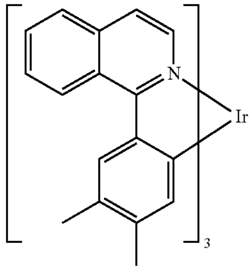

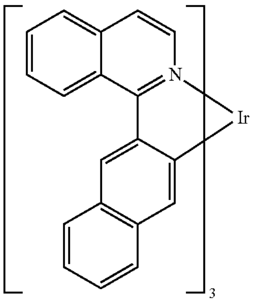

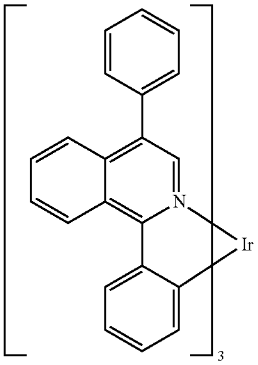

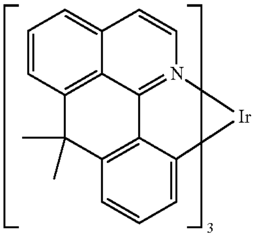

-continued
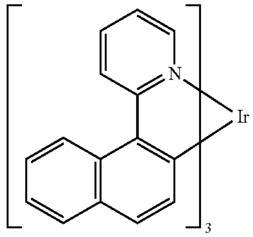
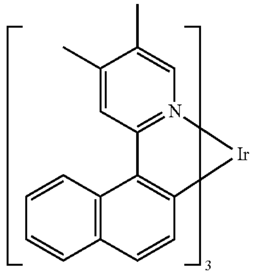
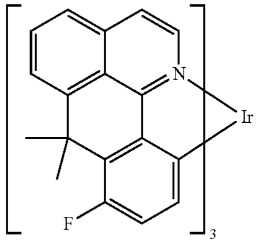
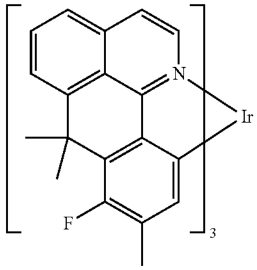
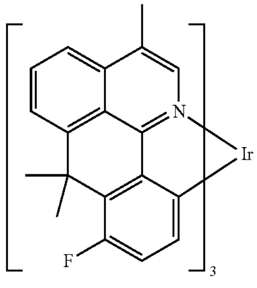
-continued
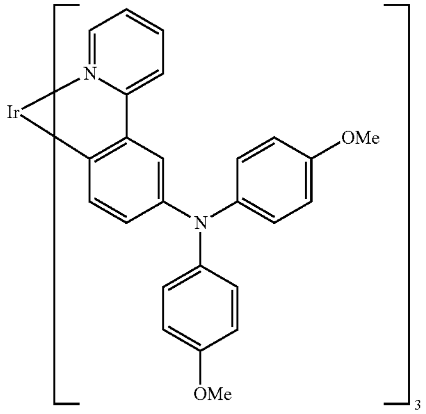
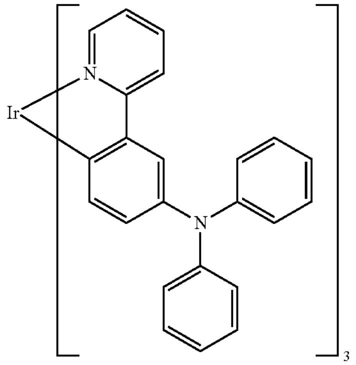
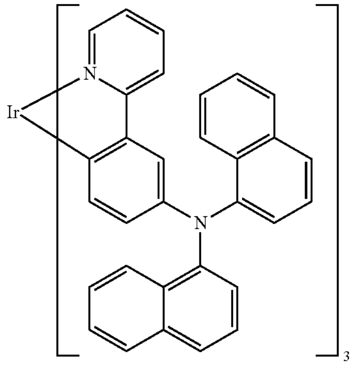
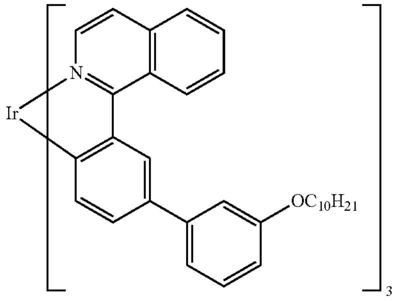

-continued
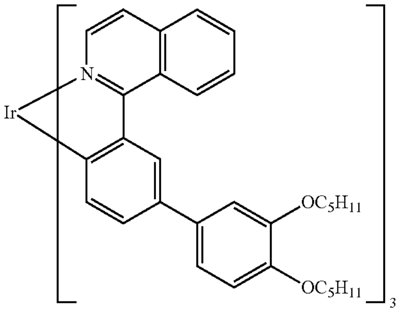
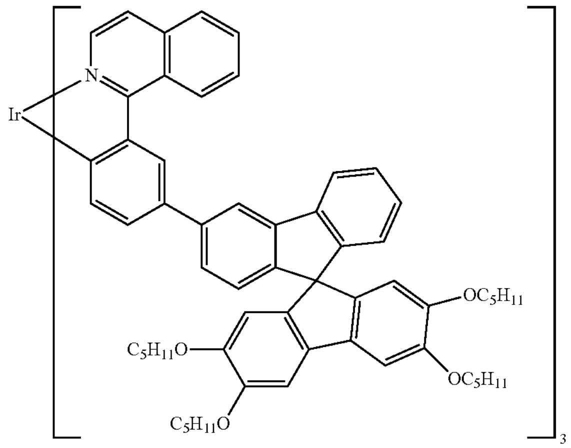
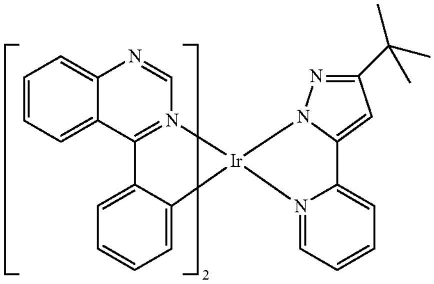
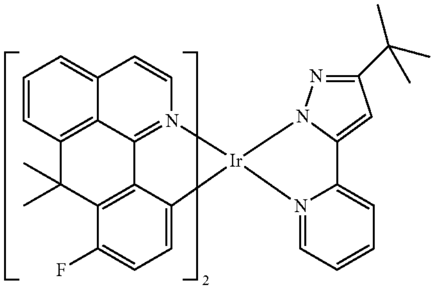
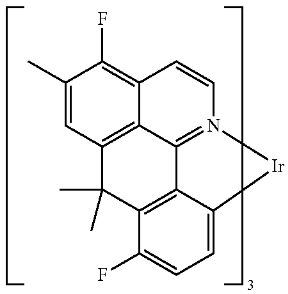
-continued
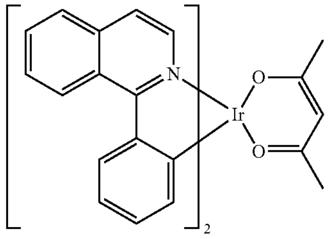
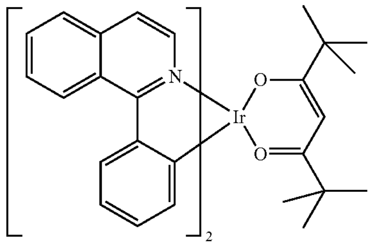
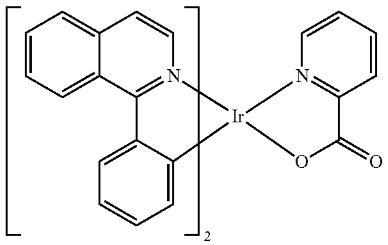
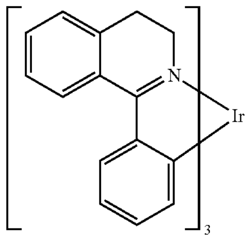
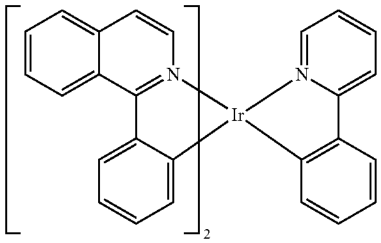
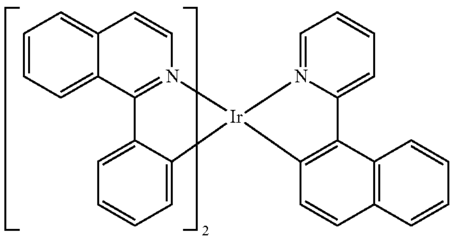

-continued
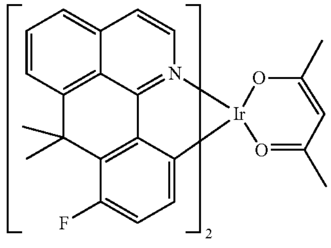
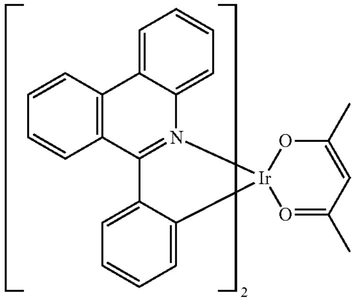
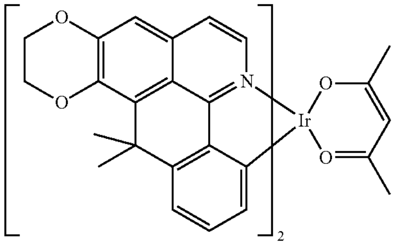
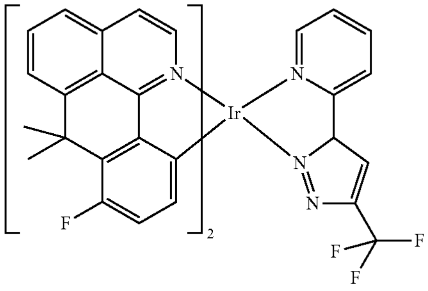
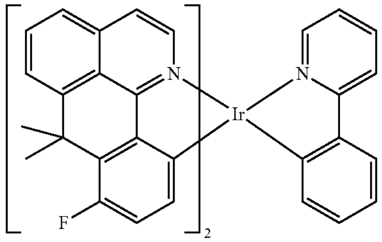
-continued
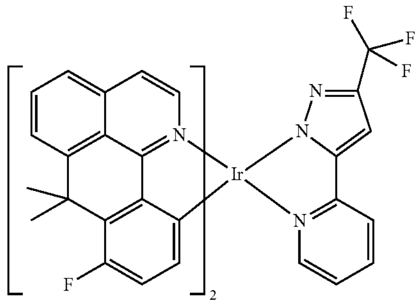
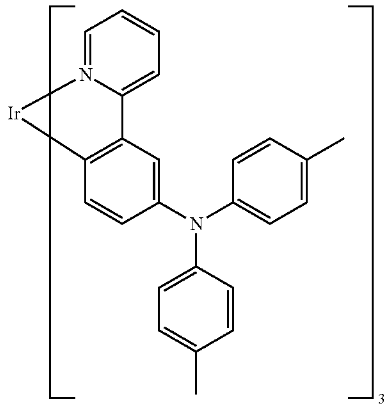
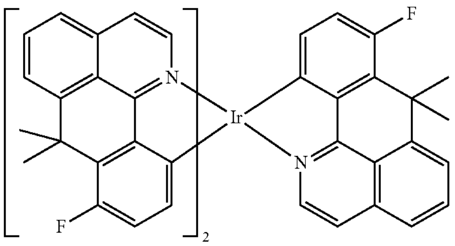
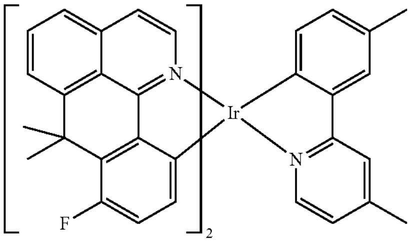
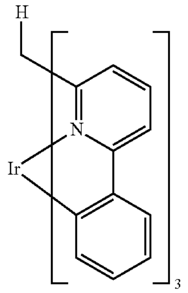

-continued
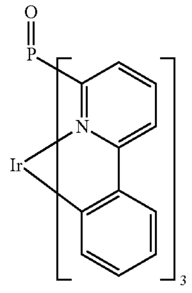
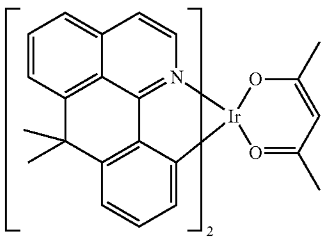
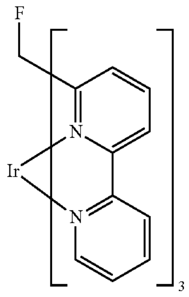
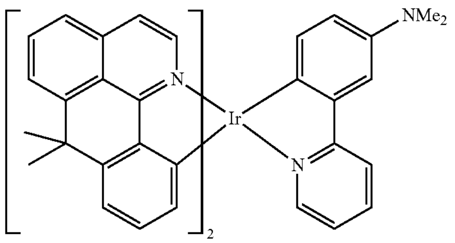
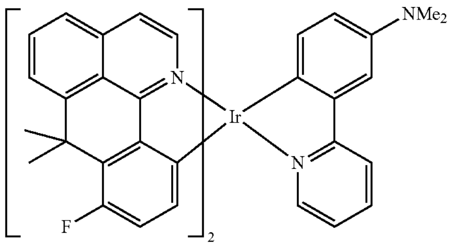
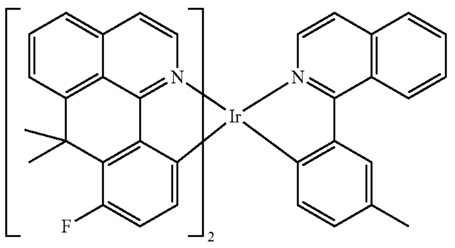
-continued
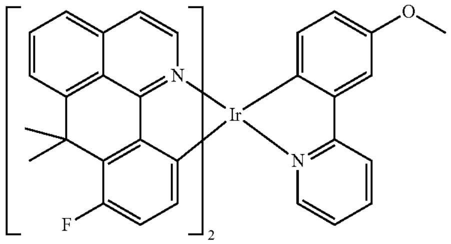
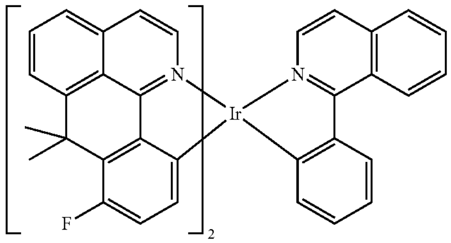
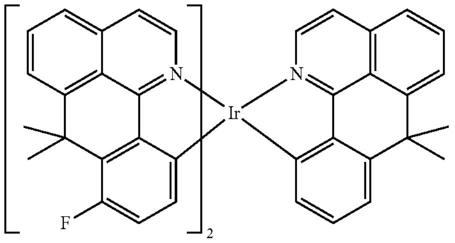
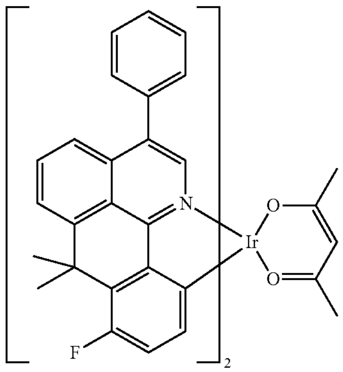
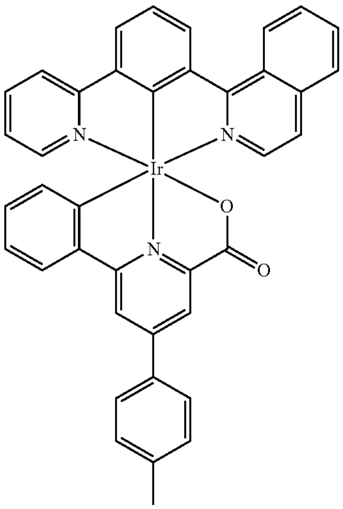

-continued
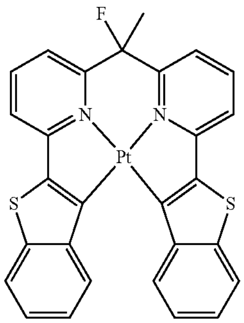
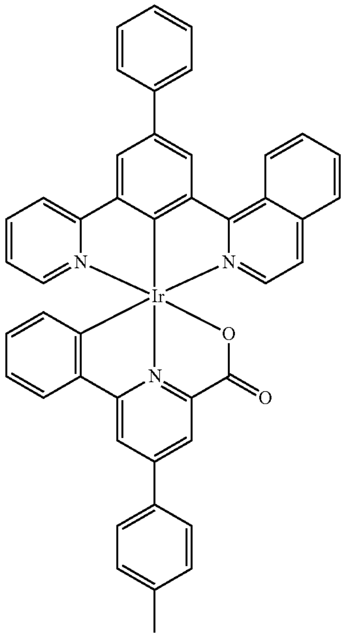
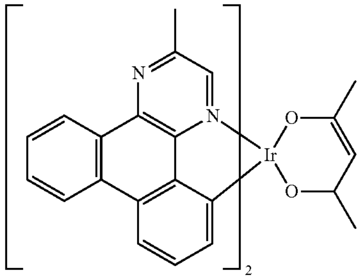
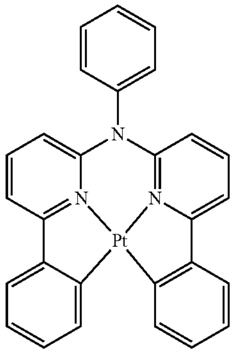
-continued
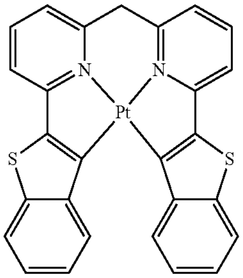
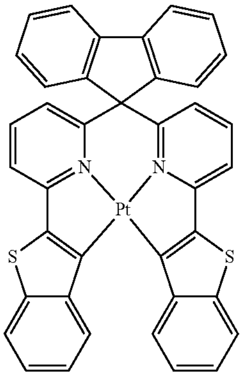
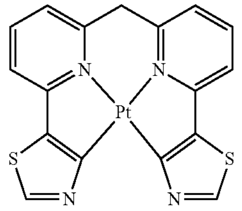
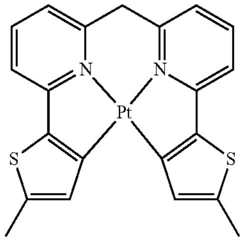
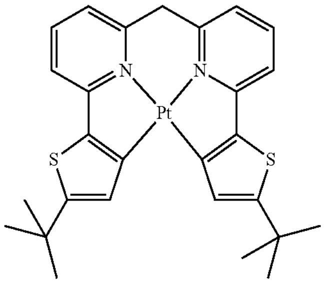
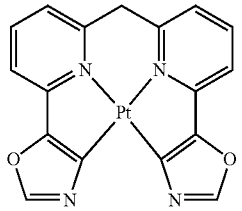

-continued
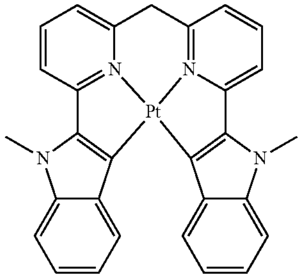
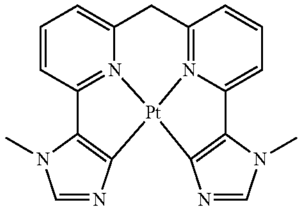
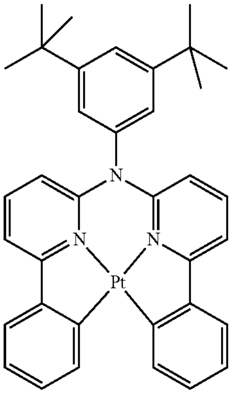
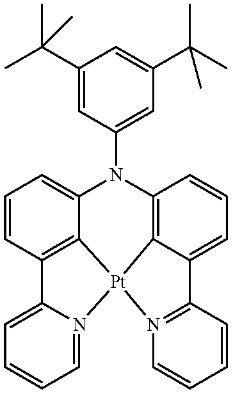
-continued
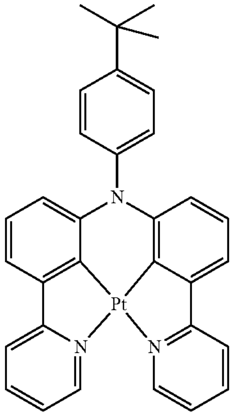
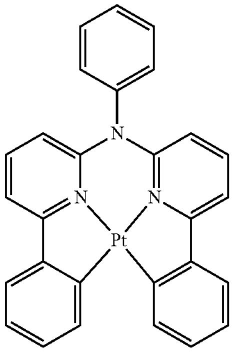
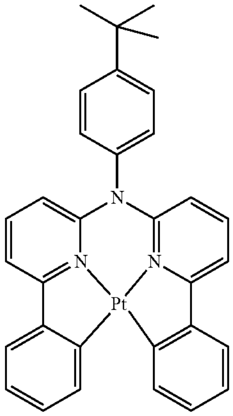
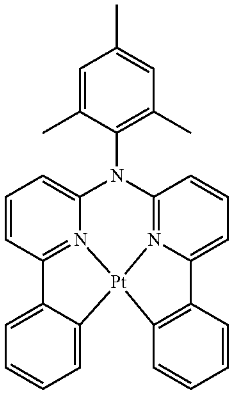

-continued
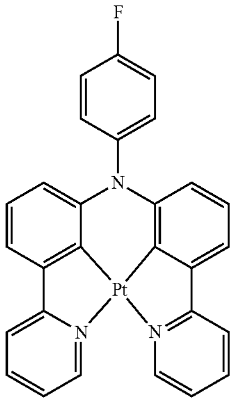
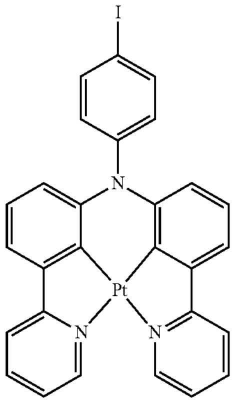
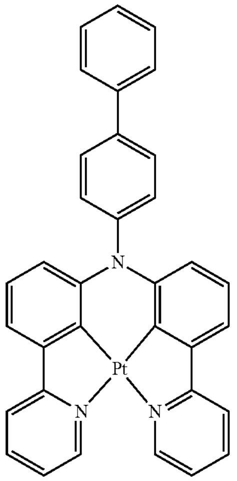
-continued
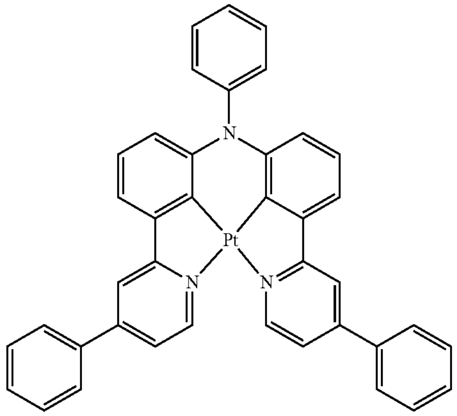
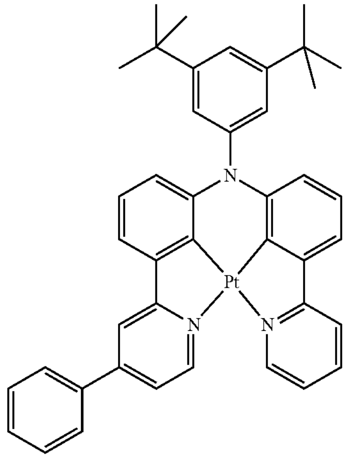
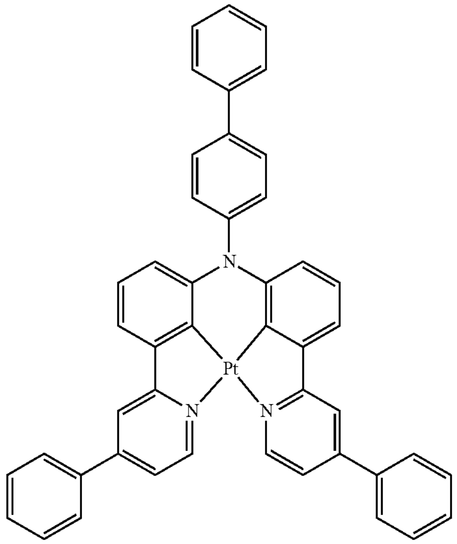

-continued
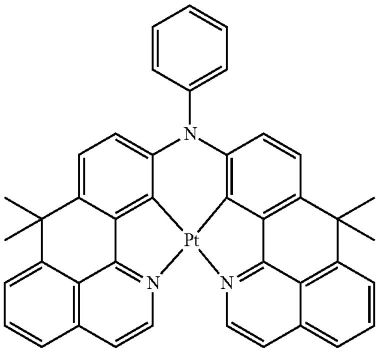
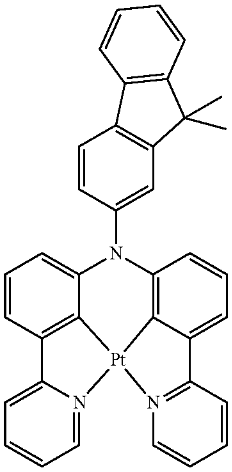
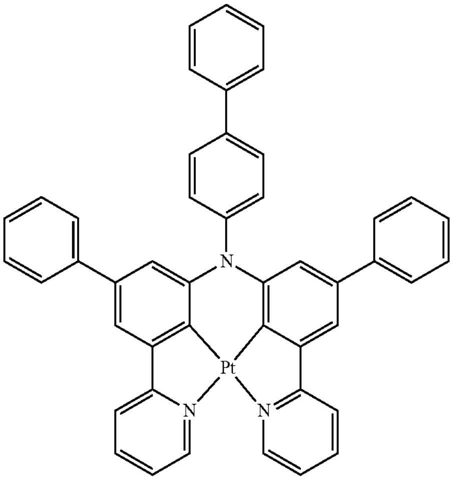
-continued
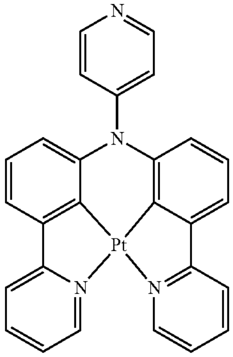
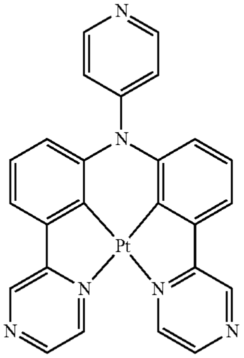
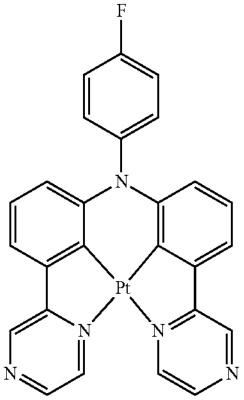
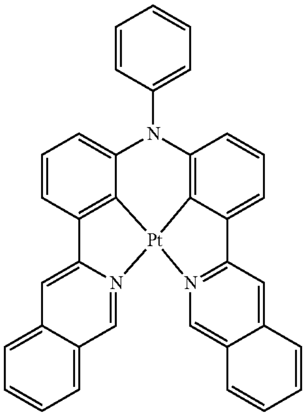

-continued
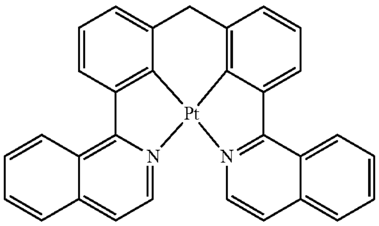
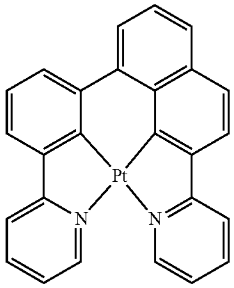
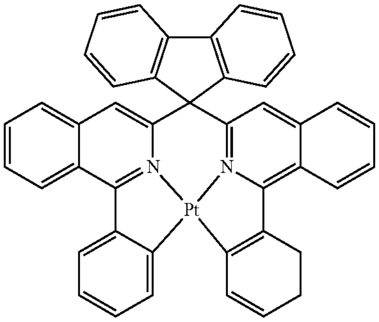
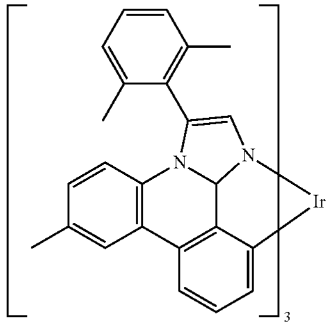
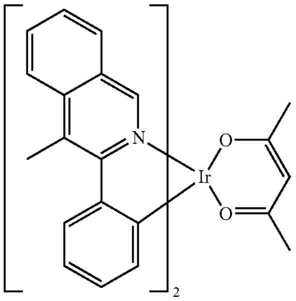
-continued
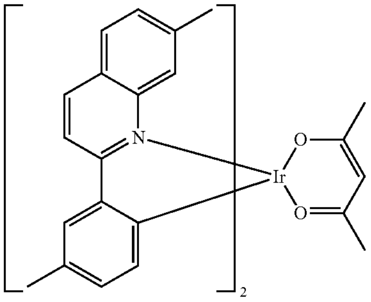
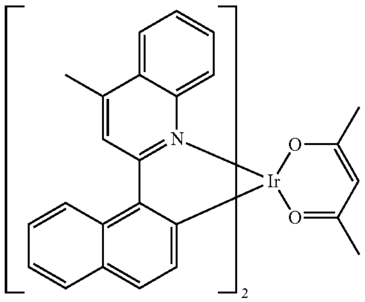
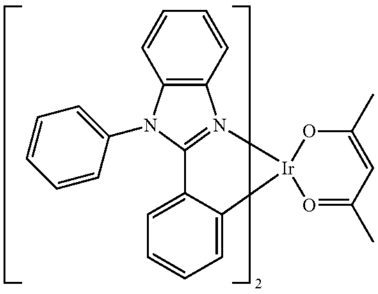
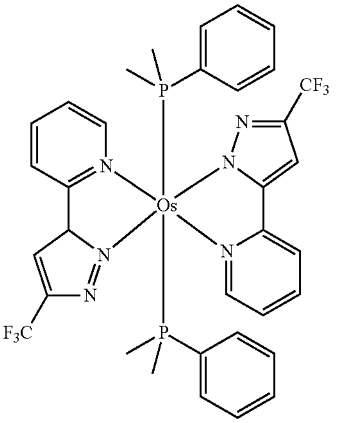
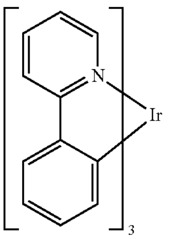

-continued
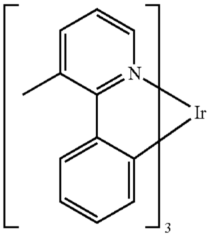
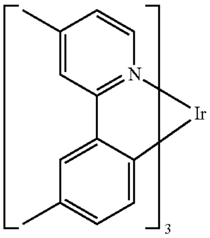
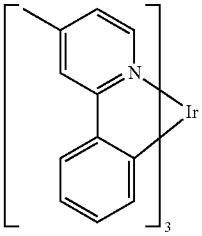
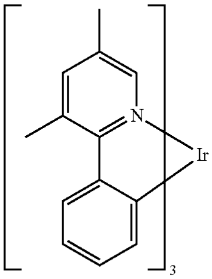
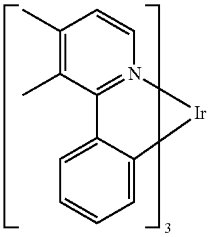
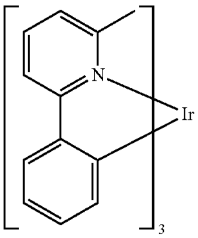
-continued
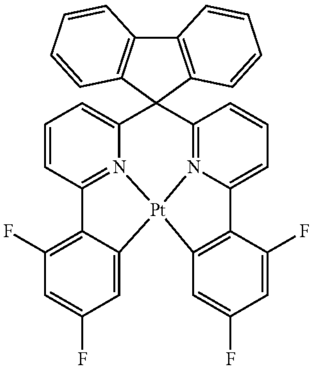
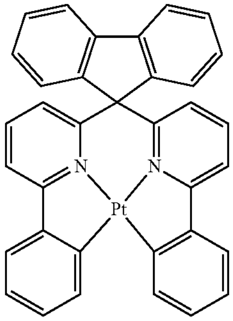
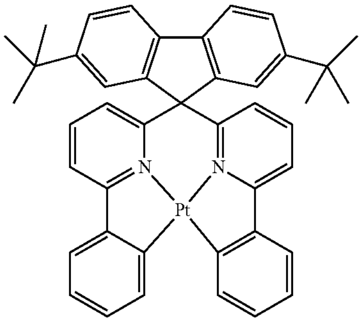
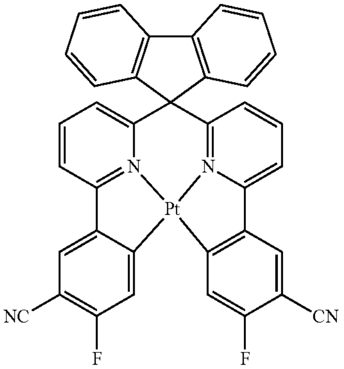

-continued
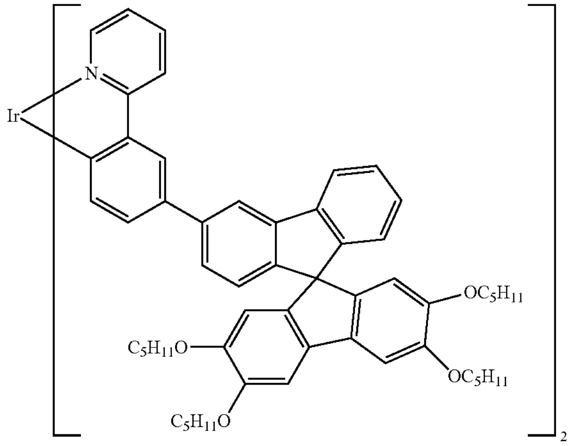
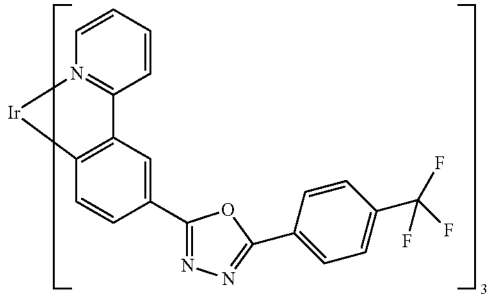
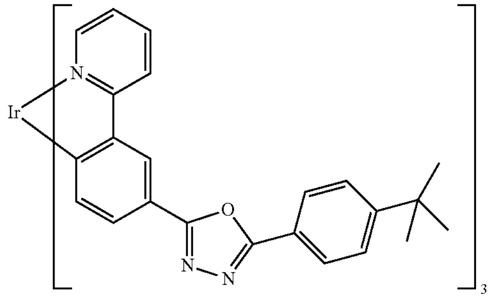
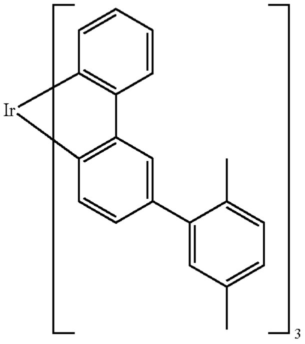
-continued
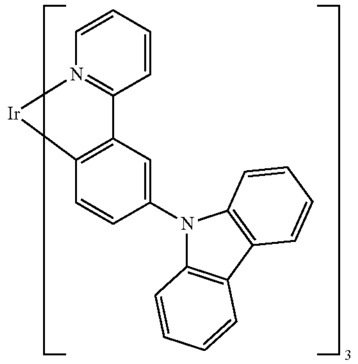
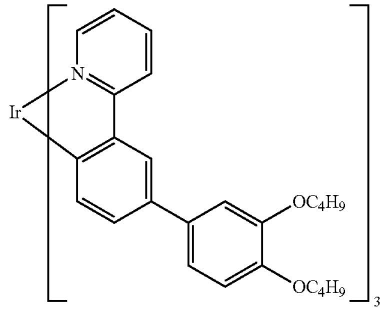
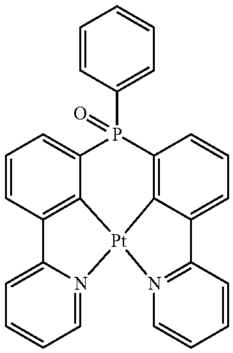
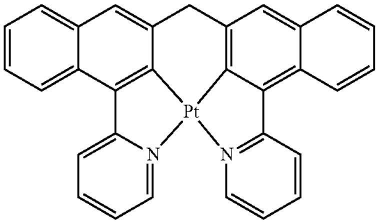

-continued
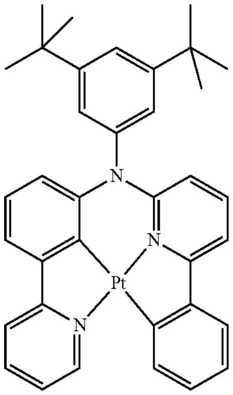
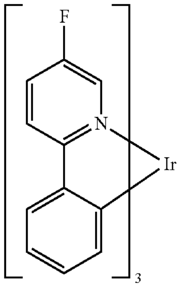
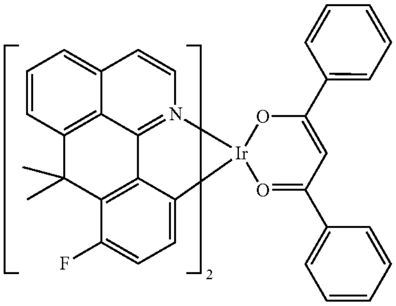
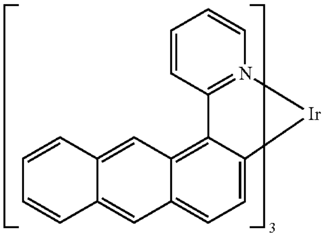
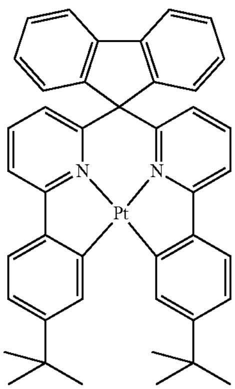
-continued
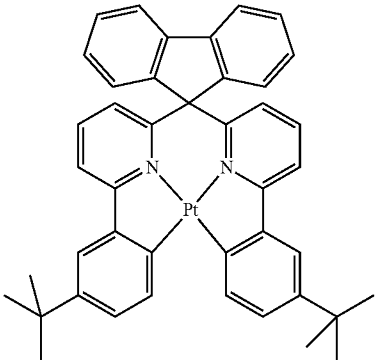
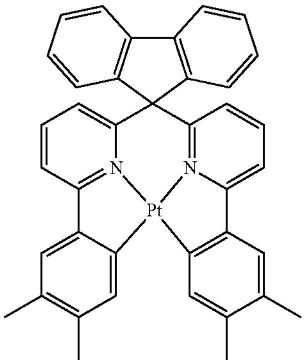
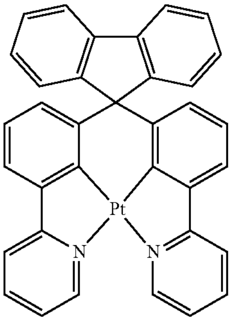
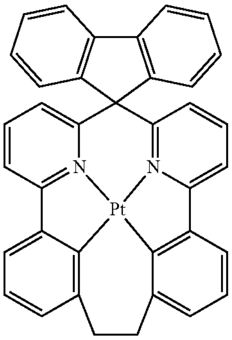

-continued
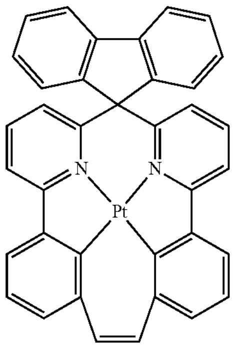
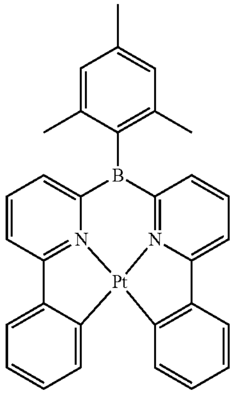
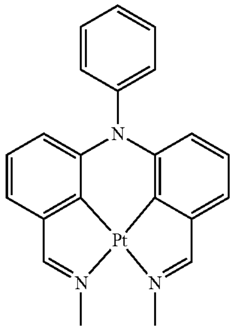
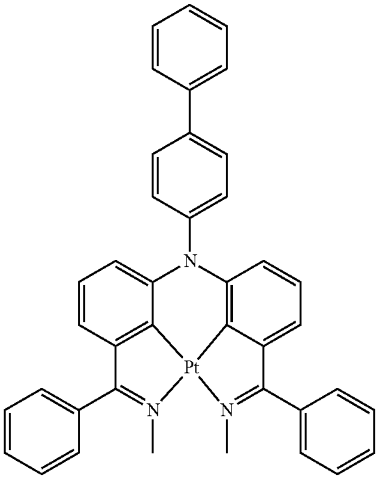
-continued
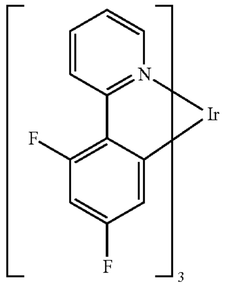
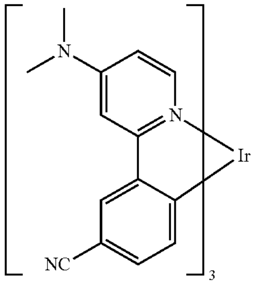
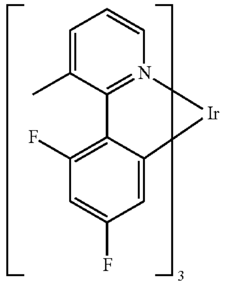
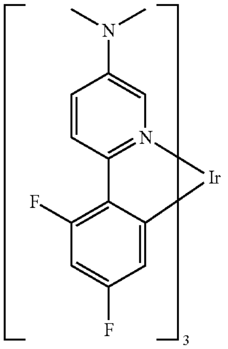
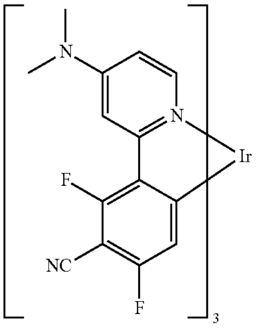

-continued
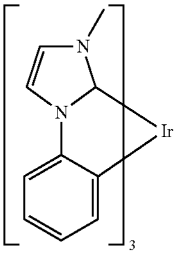
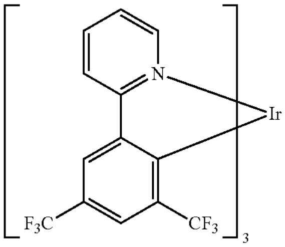
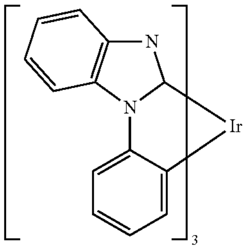
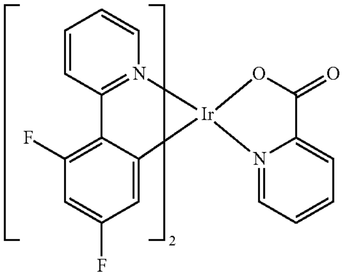
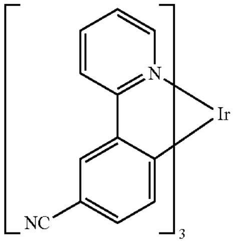
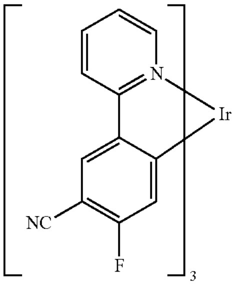
-continued
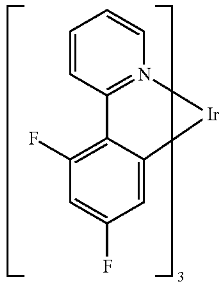
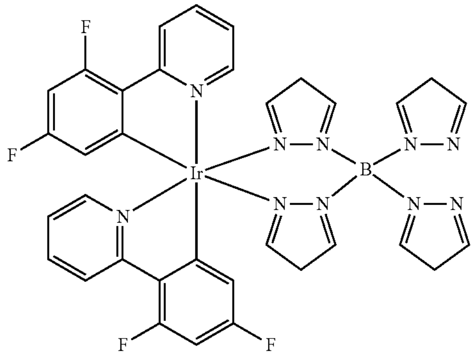
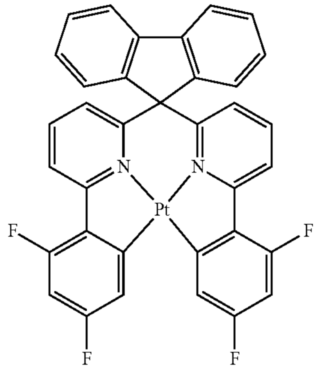
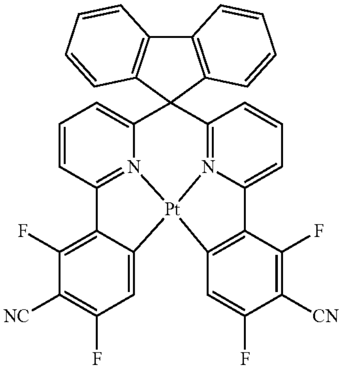

-continued

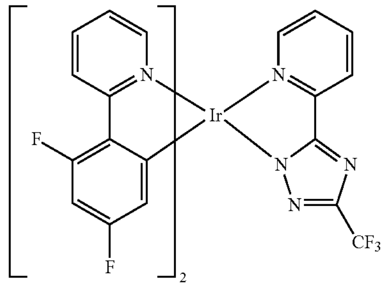

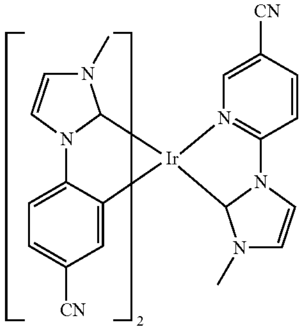

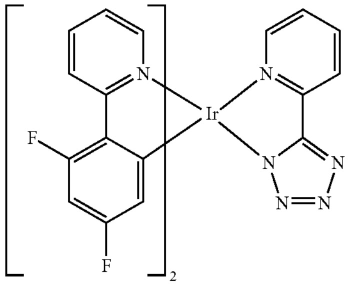

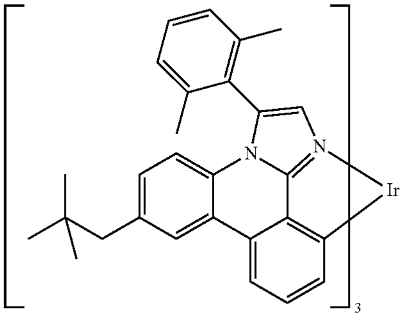

Preferred fluorescent dopants are selected from the class of the arylamines. An arylamine or an aromatic amine in the context of this invention is understood to mean a compound containing three substituted or unsubstituted aromatic or heteroaromatic ring systems bonded directly to the nitrogen. Preferably, at least one of these aromatic or heteroaromatic ring systems is a fused ring system, more preferably having at least 14 aromatic ring atoms. Preferred examples of these are aromatic anthracenamines, aromatic anthracenediamines, aromatic pyrenamines, aromatic pyrenediamines, aromatic chrysenamines or aromatic chrysenediamines. An aromatic anthracenamine is understood to mean a compound in which a diarylamino group is bonded directly to an anthracene group, preferably in the 9 position. An aromatic anthracenediamine is understood to mean a compound in which two diarylamino groups are bonded directly to an anthracene group, preferably in the 9,10 positions. Aromatic pyrenamines, pyrenediamines, chrysenamines and chrysenediamines are defined analogously, where the diarylamino groups in the pyrene are bonded preferably in the 1 position or 1,6 positions. Further preferred fluorescent dopants are selected from indenofluorenamines and -fluorenediamines, for example according to WO 2006/122630, benzoindenofluorenamines and -fluorenediamines, for example according to WO 2008/006449, and dibenzoindenofluorenamines and -fluorenediamines, for example according to WO 2007/140847. Preference is further given to the fused hydrocarbons disclosed in WO 2010/012328.

Suitable fluorescent dopants are additionally the derivatives of these structures disclosed in JP 2006100 1973, WO 2004/047499, WO 2006/098080, WO 2007/065678, US 2005/0260442 and WO 2004/092111.

Useful matrix materials, preferably for fluorescent dopants, include materials of various substance classes. Preferred matrix materials are selected from the classes of the oligoarylenes (e.g. 2,2',7,7'-tetraphenylspirobifluorene according to EP 676461 or dinaphthylanthracene), especially of the oligoarylenes containing fused aromatic groups, the oligoarylenevinylenes (e.g. DPVBi or spiro-DPVBi according to EP 676461), the polypodal metal complexes (for example according to WO 2004/081017), the hole-conducting compounds (for example according to WO 2004/058911), the electron-conducting compounds, especially ketones, phosphine oxides, sulfoxides, etc. (for example according to WO 2005/084081 and WO 2005/084082), the atropisomers (for example according to WO 2006/048268), the boronic acid derivatives (for example according to WO 2006/117052) or the benzanthracenes (for example according to WO 2008/145239). Particularly preferred matrix materials are selected from the classes of the oligoarylenes comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes comprising, anthracene, benzanthracene, benzophenanthrene and/or pyrene or atropisomers of these compounds. An oligoarylene in the context of this invention shall be understood to mean a compound in which at least three aryl or arylene groups are bonded to one another.

Preferred matrix materials for phosphorescent dopants are, as well as the compounds of the invention, carbazole derivatives (e.g. CBP (N,N-biscarbazolylbiphenyl) or compounds according to WO 2005/039246, US 2005/0069729, JP 2004/288381, EP 1205527 or WO 2008/086851), triarylamines, azacarbazoles (for example according to EP 1617710, EP 1617711, EP 1731584, JP 2005/347160), indolocarbazole derivatives, for example according to WO 2007/063754 or WO 2008/056746, ketones (for example according to WO 2004/093207 or WO 2010/006680), phosphine oxides, sulfoxides and sulfones (for example according to WO 2005/003253), oligophenylenes, aromatic amines (for example according to US 2005/0069729), bipolar matrix materials (for example according to WO 2007/137725), silanes (for example according to WO 2005/111172), azaboroles or boronic esters, for example according to WO 2006/117052, triazine derivatives, for example according to WO 2010/015306, WO 2007/063754 or WO 2008/056746, zinc complexes (for example according to WO 20091062578), aluminum complexes (e.g. BAlq), diazasilole and tetraazasilole derivatives, for example according to WO 2010/054730, indenocarbazole derivatives, for example according to WO 2010/136109 and WO 2011/000455, or diazaphospholes, for example according to WO 2010/054730.

Suitable charge transport materials as usable in the hole injection or hole transport layer or in the electron transport layer of the organic electroluminescent device of the invention are, as well as the compounds of the invention, for example, the compounds disclosed in Y. Shirota et al., Chem. Rev. 2007, 107(4), 953-1010, or other materials as used in these layers according to the prior art.

Preferred cathodes are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag or Al, in which case combinations of the metals such as Ca/Ag, Ba/Ag or Mg/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). It is also possible to use lithium quinolinate (LiQ) for this purpose. The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable the irradiation of the organic material (organic solar cell) or the emission of light (OLED, O-LASER). Preferred anode materials here are conductive mixed metal oxides. Particular preference is given to indium tin oxide (ITO) or indium zinc oxide (IZO). Preference is further given to conductive doped organic materials, especially conductive doped polymers.

The device is appropriately (according to the application) structured, contact-connected and finally sealed, since the lifetime of the devices of the invention is shortened in the presence of water and/or air.

In a preferred embodiment, the organic electroluminescent device of the invention is characterized in that one or more layers are coated by a sublimation process. In this case, the materials are applied by vapor deposition in vacuum sublimation systems at an initial pressure of less than $10^{-5}$ mbar, preferably less than $10^{-6}$ mbar. In this case, however, it is also possible that the initial pressure is even lower, for example less than $10^{-7}$ mbar.

Preference is likewise given to an organic electroluminescent device, characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured (for example M. S. Arnold et al., Appl. Phys. Lett. 2008, 92, 053301).

Preference is additionally given to an organic electroluminescent device, characterized in that one or more layers are produced from solution, for example by spin-coating, or by any printing method, for example screen printing, flexographic printing, nozzle printing or offset printing, but more preferably LITI (light-induced thermal imaging, thermal transfer printing) or inkjet printing. For this purpose, soluble compounds of formula (1) or (2) are needed. High solubility can be achieved by suitable substitution of the compounds.

It is further preferable that an organic electroluminescent device of the invention is produced by applying one or more layers from solution and one or more layers by a sublimation method.

The organic electroluminescent devices comprising one or more compounds of the invention can be used in displays, as light sources in lighting applications and as light sources in medical and/or cosmetic applications (e.g. light therapy).

It is a particular feature of the compounds of the invention that, when used in organic electroluminescent devices, they bring about good power efficiencies, low operating voltages and long lifetimes of the devices.

In addition, the compounds are oxidation-stable and thermally stable and have a high glass transition temperature, which is advantageous for processibility, for example from solution or from the gas phase, and also for use in electronic devices.

In addition, the compounds have high hole mobility, which is highly desirable especially in the case of use as hole transport material or hole injection material.

The invention is elucidated in detail by the use examples which follow, although the invention is not restricted to the scope of the examples.

WORKING EXAMPLES

The syntheses which follow, unless stated otherwise, are conducted under a protective gas atmosphere. The reactants can be sourced from ALDRICH or ABCR (palladium(II) acetate, tri-o-tolylphosphine, inorganic materials, solvents).

Example 1: 9-(2-Bromophenyl)-9H-fluoren-9-ol

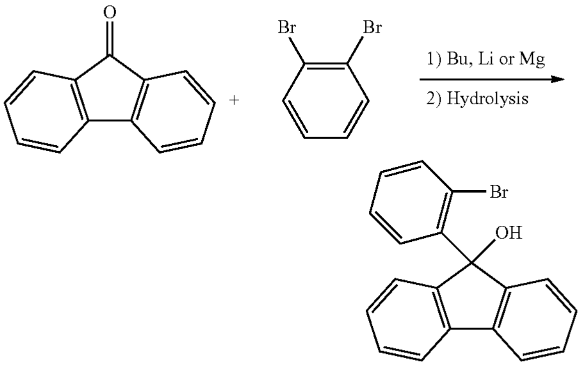

1

2.68 g (110 mmol) of iodine-activated magnesium turnings and a mixture of 25.9 g (110 mmol) of 1,2-dibromobenzene, 0.8 mL of 1,2-dichloroethane, 50 mL of 1,2-dimethoxyethane, 500 mL of THF are used to prepare the corresponding Grignard reagent by trace heating with an oil bath at 70° C. Once the magnesium has reacted fully, the mixture is cooled to room temperature and then a solution of 18.0 g (100 mmol) of fluorenone [486-25-9] in 300 mL of THF is added dropwise, and the reaction mixture is heated to 50° C. for 4 h and then stirred at room temperature for a further 12 h. 100 mL of water are added, the mixture is stirred briefly, the organic phase is removed and the solvent is removed under reduced pressure. Subsequently, the residue is stirred with 500 mL of heptane at 80° C. for 2 h. After cooling, the precipitated solids are filtered off with suction and washed once with 100 mL of heptane and twice with 100 mL each time of ethanol, and finally recrystallized from dioxane/EtOH. Yield: 24.6 g (73 mmol), 73%; purity about 98% by $^{1}H$ NMR.

In an analogous manner, the following compounds are obtained:

| | Reactant 1 | Reactant 2 | Product | Yield |
|---|---|---|---|---|
| 1a | 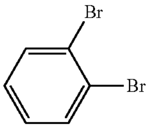 583-53-9 | 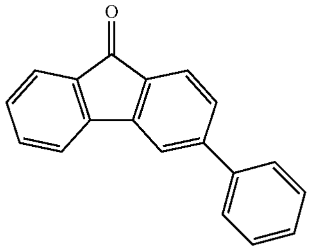 19063-39-9 | 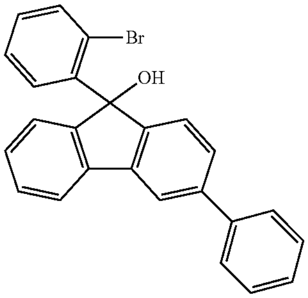 1a | 85% |
| 1b | 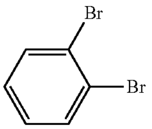 583-53-9 | 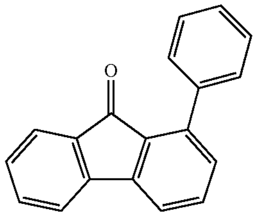 5501-35-9 | 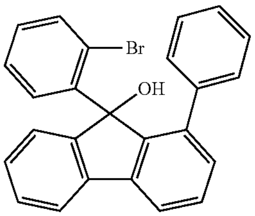 1b | 70% |
| 1c | 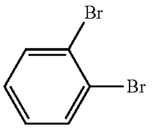 583-53-9 | 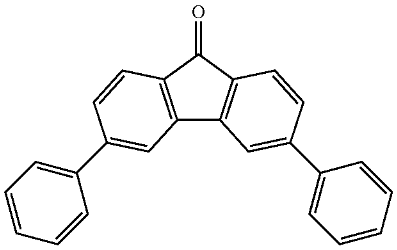 1397678-19-1 | 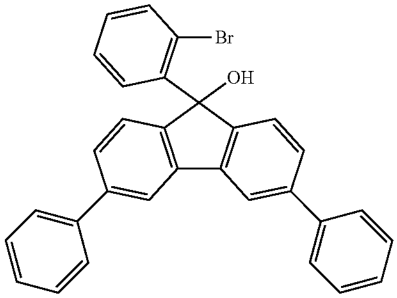 1c | 85% |
| 1d | 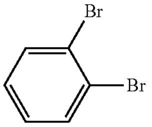 583-53-9 | 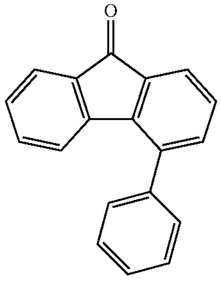 4269-14-1 | 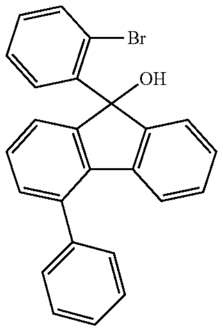 1d | 83% |

-continued
| | Reactant 1 | Reactant 2 | Product | Yield |
|---|---|---|---|---|
| 1e | 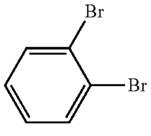 583-53-9 | 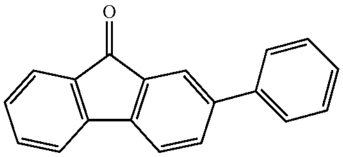 3096-49-9 | 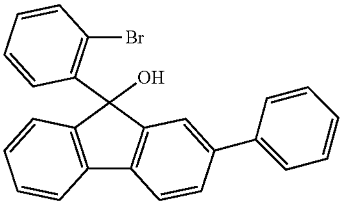 1e | 81% |
| 1f | 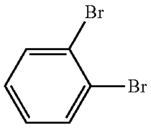 583-53-9 | 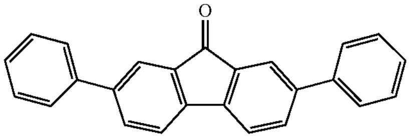 115033-91-5 | 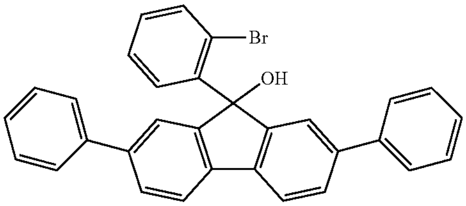 1f | 74% |
| 1g | 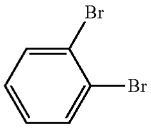 583-53-9 | 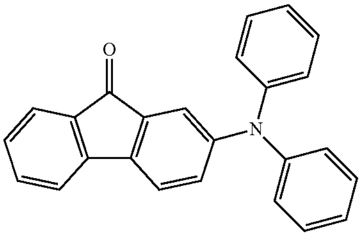 1338442-16-2 | 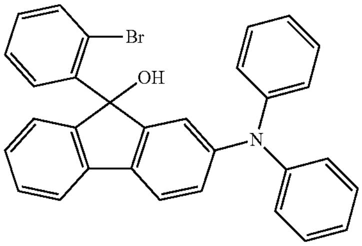 1g | 81% |
| 1h | 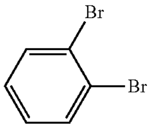 583-53-9 | 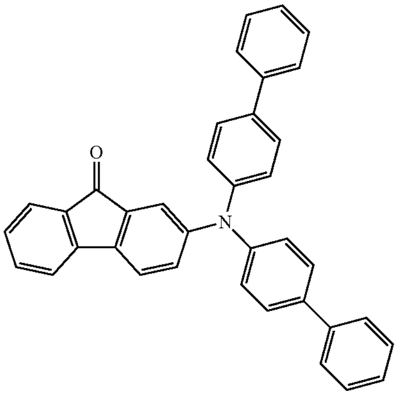 [SMILES: O=C1c2ccccc2-c2ccc(N(c3ccc(-c4ccccc4)cc3)c3ccc(-c4ccccc4)cc3)cc21] | 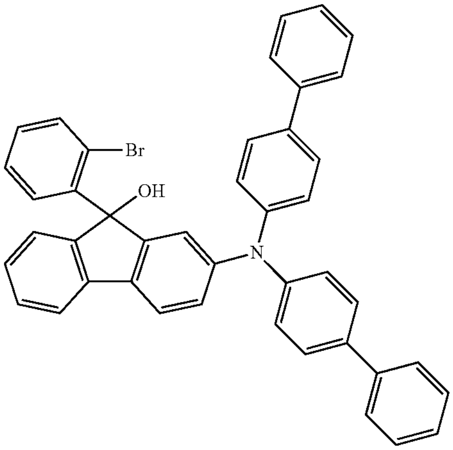 1h | 76% |

-continued
| | Reactant 1 | Reactant 2 | Product | Yield |
|---|---|---|---|---|
| 1i | 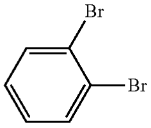 583-53-9 | 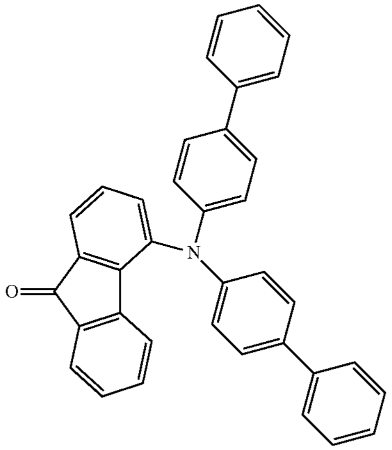 [SMILES: O=C1c2ccccc2-c2c1cccc2N(c1ccc(-c2ccccc2)cc1)c1ccc(-c2ccccc2)cc1] | 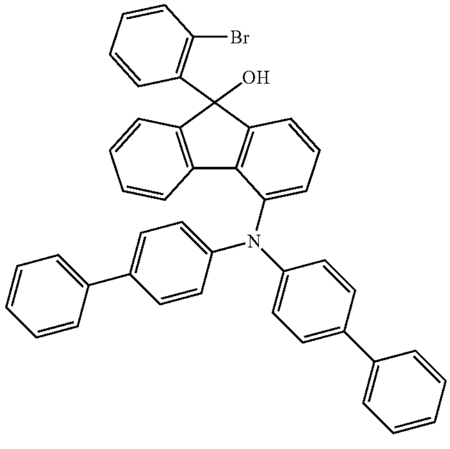 1i | 74% |
| 1j | 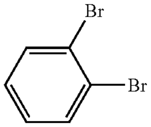 583-53-9 | 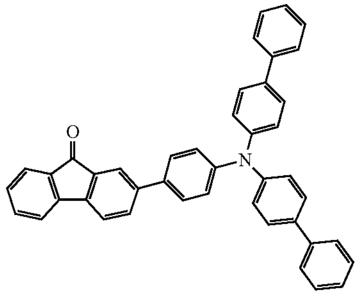 [SMILES: O=C1c2ccccc2-c2ccc(-c3ccc(N(c4ccc(-c5ccccc5)cc4)c4ccc(-c5ccccc5)cc4)cc3)cc21] | 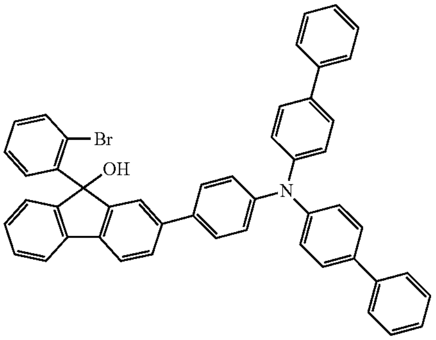 1j | 72% |
Example 2: Bis(biphenyl-4-yl){4-[9-(2-bromophenyl)-9H-fluoren-9-yl]phenyl}amine
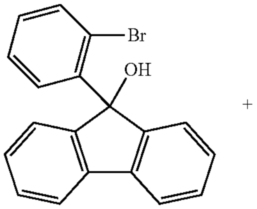
1
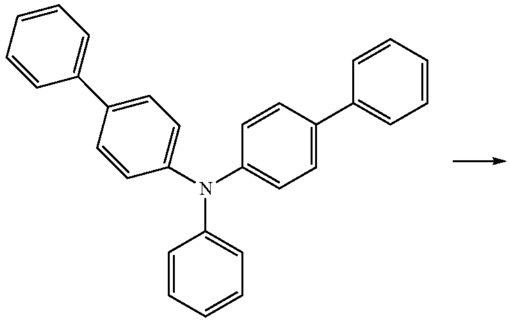
-continued
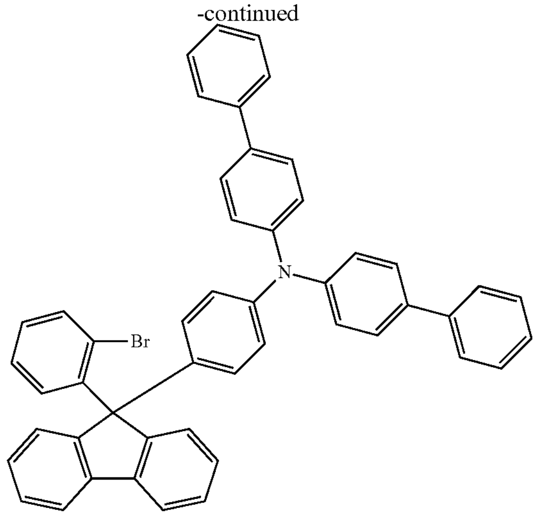
2
A mixture of 16.85 g (50 mmol) of 9-(2-bromophenyl)-9H-fluoren-9-ol and 19.88 g (50 mmol) of bis(biphenyl-4-yl)phenylamine [122215-84-3], 15 g (100 mmol, 8.8 mL) of trifluoromethanesulfonic acid [1493-13-6] and 300 mL of dioxane is heated under reflux for 24 h. After cooling, 200 mL of water are added, the mixture is stirred for a further 30 min, the organic phase is removed and the latter is filtered through a short Celite bed and then the solvent is removed under reduced pressure. The residue is recrystallized twice from toluene/heptane. Yield: 26.1 g (36.5 mmol), 73%; purity about 98% by $^{1}$H NMR.

In an analogous manner, the following compounds are obtained:

| Ex. | Reactant 1 | Reactant 2 | Product: | Yield |
|---|---|---|---|---|
| 2a | 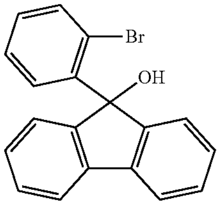 1 [312968-36-8] | 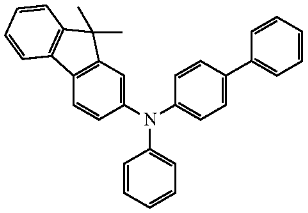 [1391737-67-9] | 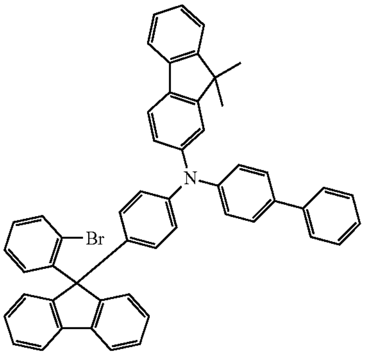 2a | 85% |
| 2b | 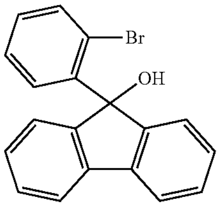 1 [312968-36-8] | 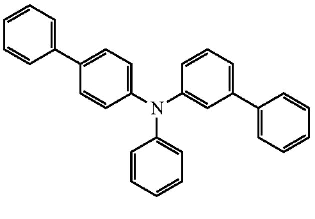 [SMILES: c1ccc(-c2ccc(N(c3ccccc3)c3cccc(-c4ccccc4)c3)cc2)cc1] | 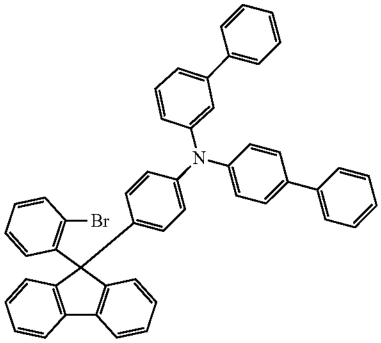 2b | 74% |
| 2c | 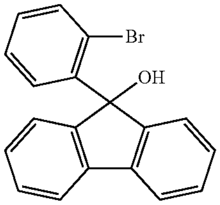 1 [312968-36-8] | 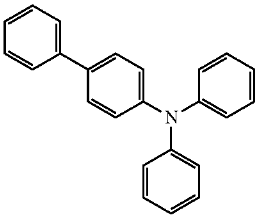 [4432-94-4] | 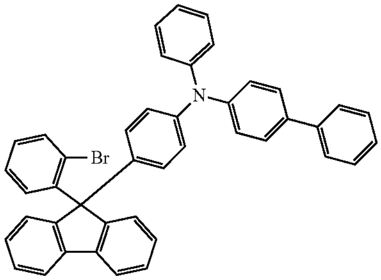 2c | 70% |
| 2e | 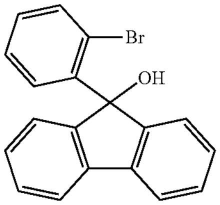 1 [312968-36-8] | 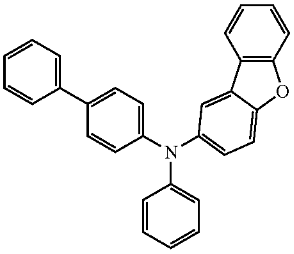 [SMILES: c1ccc(-c2ccc(N(c3ccccc3)c3ccc4oc5ccccc5c4c3)cc2)cc1] | 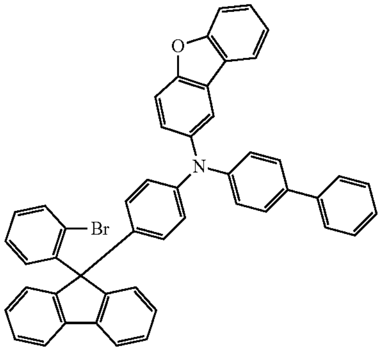 2e | 62% |

-continued
| Ex. | Reactant 1 | Reactant 2 | Product: | Yield |
|---|---|---|---|---|
| 2f | 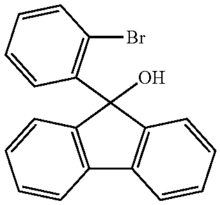 1 [312968-36-8] | 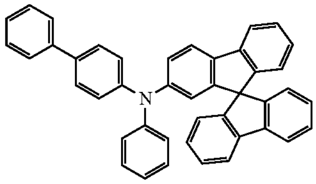 [SMILES: c1ccc(-c2ccc(N(c3ccccc3)c3ccc4c(c3)C3(c5ccccc5-c5ccccc53)c3ccccc3-4)cc2)cc1] | 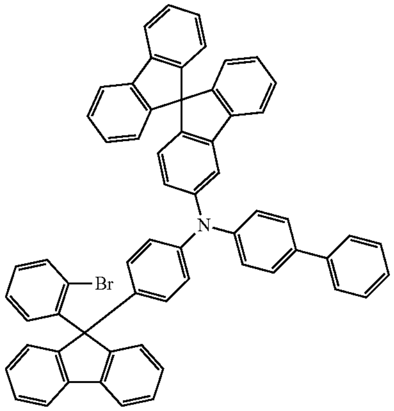 2f | 58% |
| 2g | 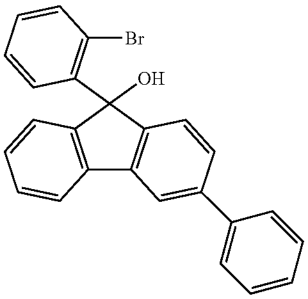 1a | 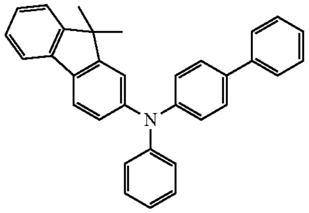 [1391737-67-9] | 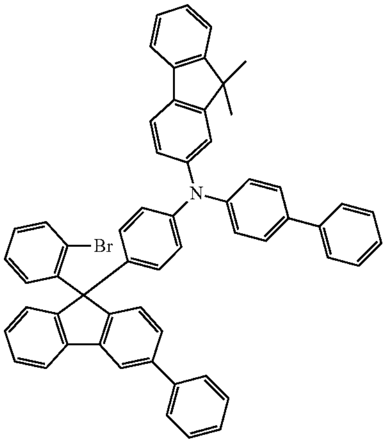 2g | 85% |
| 2h | 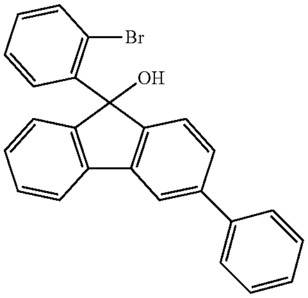 1a | 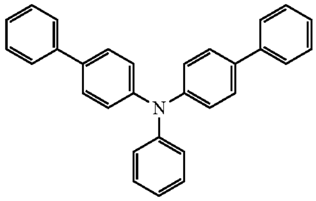 [122215-84-3] | 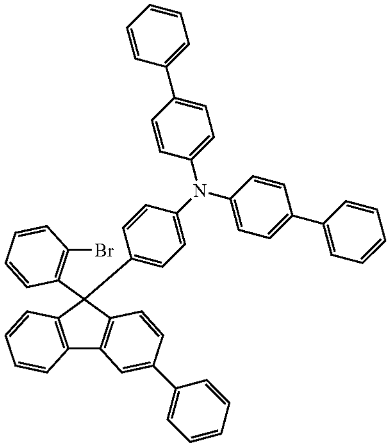 2h | 79% |

-continued
| Ex. | Reactant 1 | Reactant 2 | Product: | Yield |
|---|---|---|---|---|
| 2i | 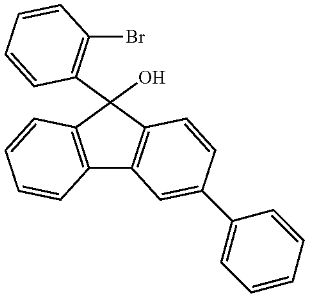 1a | 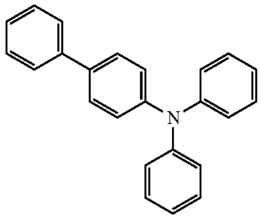 [4432-94-4] | 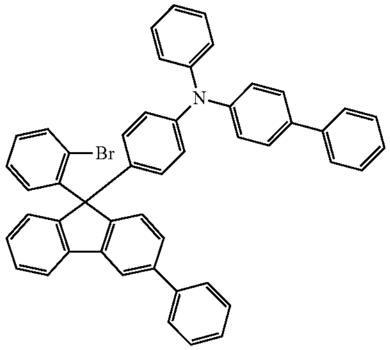 2i | 78% |
| 2j | 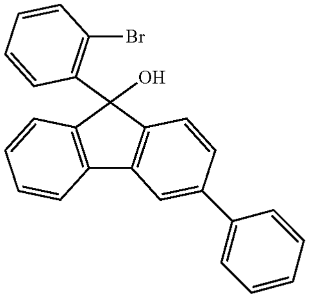 1a | 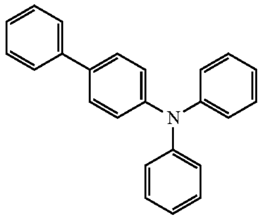 [4432-94-4] | 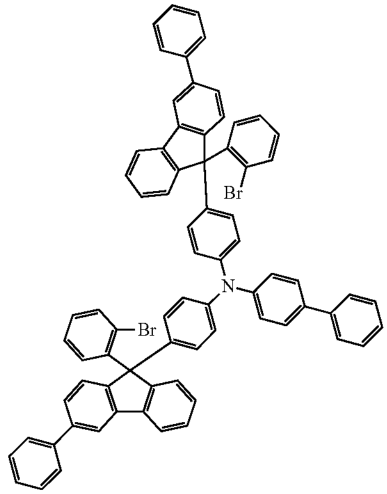 2j | 68% |
| 2k | 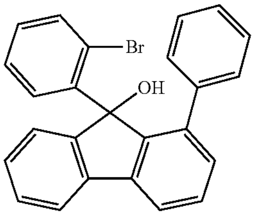 1b | 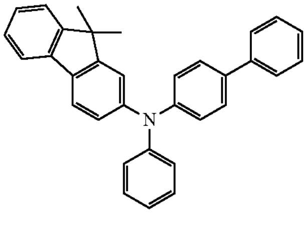 [1391737-67-9] | 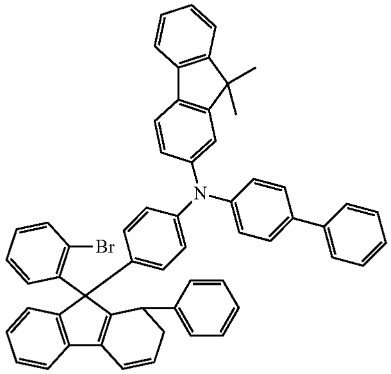 2k | 45% |

-continued
| Ex. | Reactant 1 | Reactant 2 | Product: | Yield |
|---|---|---|---|---|
| 2l | 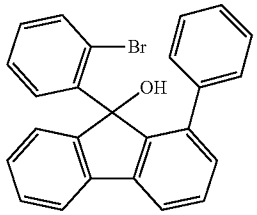<br>1b | 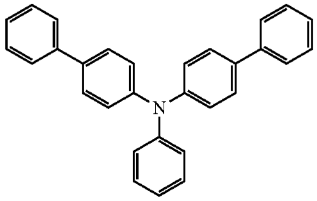<br>[122215-84-3] | 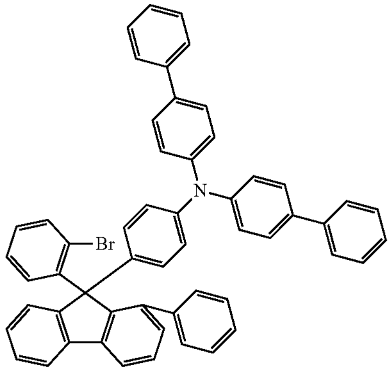<br>2l | 41% |
| 2m | 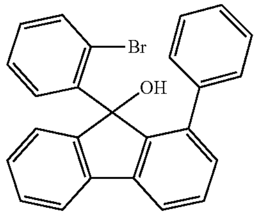<br>1b | 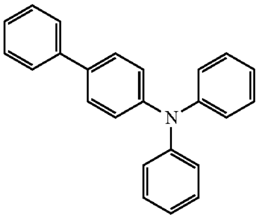<br>[4432-94-4] | 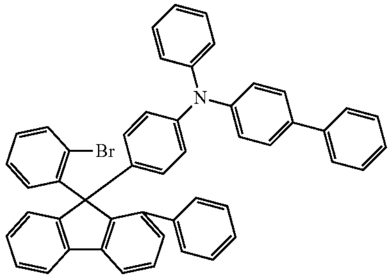<br>2m | 48% |
| 2n | 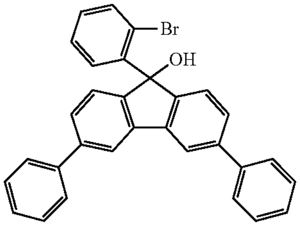<br>1c | 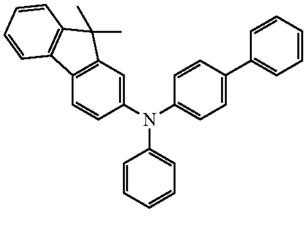<br>[1391737-67-9] | 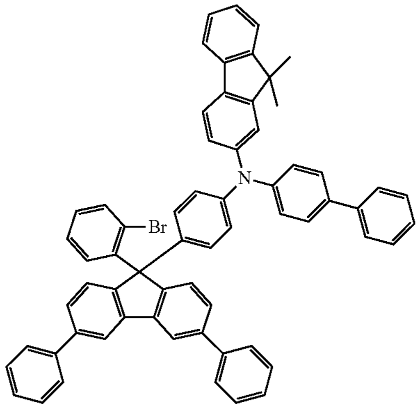<br>2n | 58% |

-continued
| Ex. | Reactant 1 | Reactant 2 | Product: | Yield |
| --- | --- | --- | --- | --- |
| 2o | 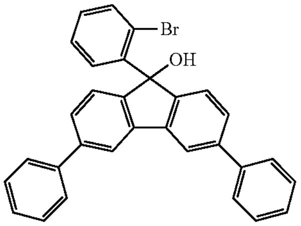 1c | 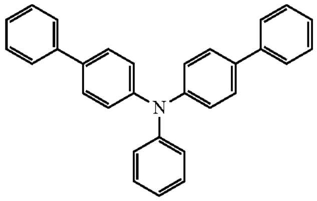 [122215-84-3] | 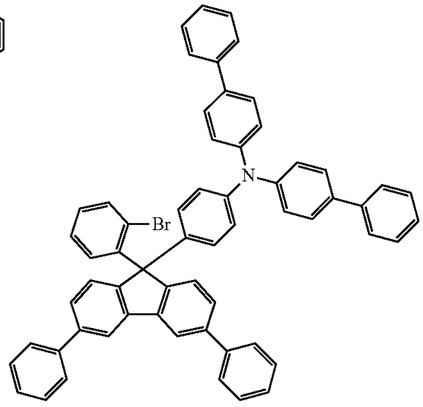 2o | 70% |
| 2p | 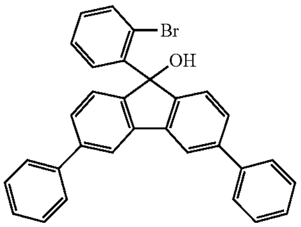 1c | 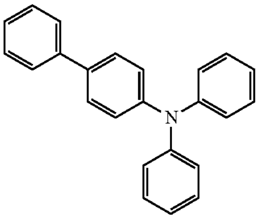 [4432-94-4] | 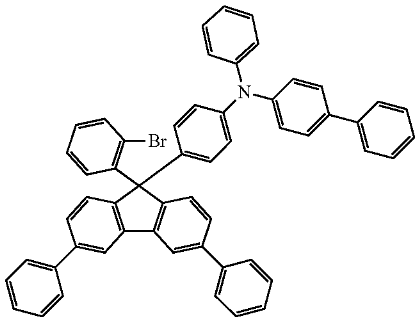 2p | 62% |
| 2r | 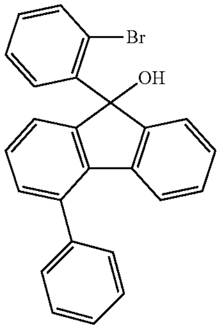 1d | 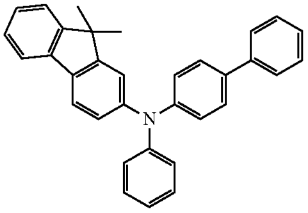 [1391737-67-9], | 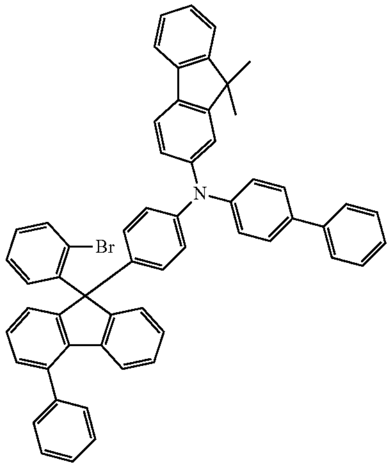 2r | 58% |

-continued
| Ex. | Reactant 1 | Reactant 2 | Product: | Yield |
| --- | --- | --- | --- | --- |
| 2s | 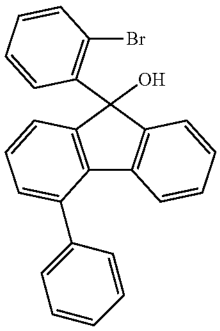 1d | 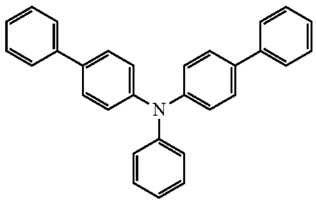 [122215-84-3] | 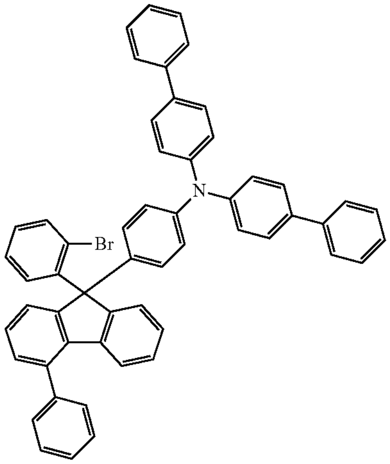 2s | 70% |
| 2t | 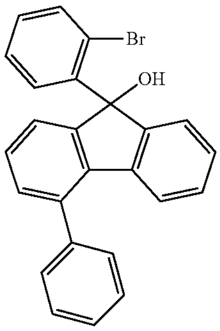 1d | 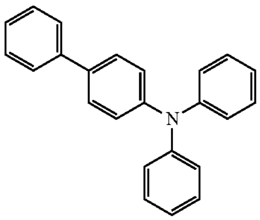 [4432-94-4] | 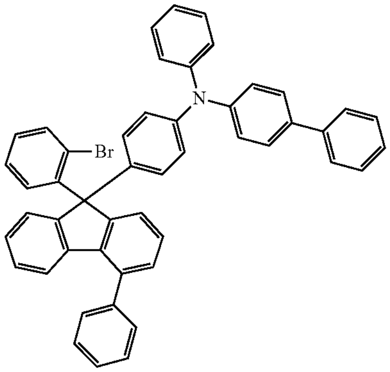 2t | 78% |
| 2u | 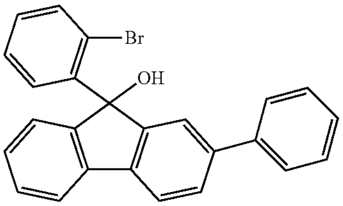 1e | 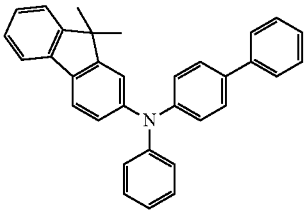 [1391737-67-9] | 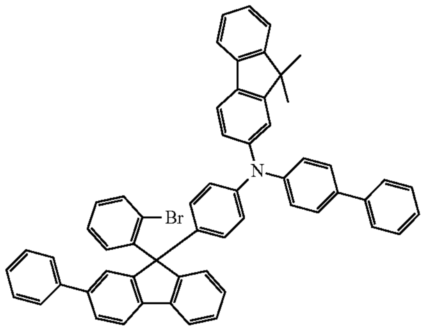 2u | 82% |

-continued
| Ex. | Reactant 1 | Reactant 2 | Product: | Yield |
|---|---|---|---|---|
| 2v | 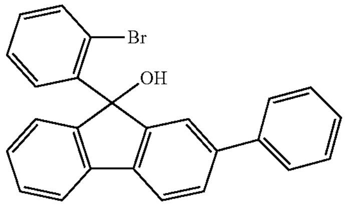 1e | 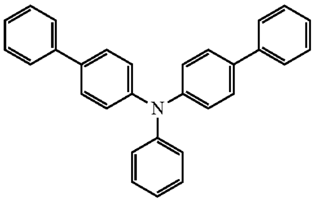 [122215-84-3] | 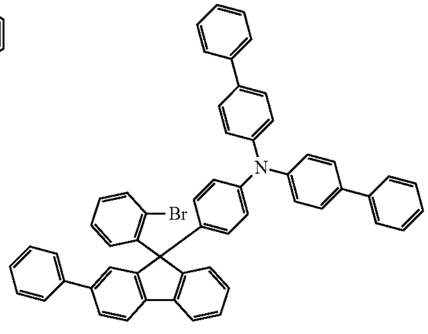 2v | 70% |
| 2w | 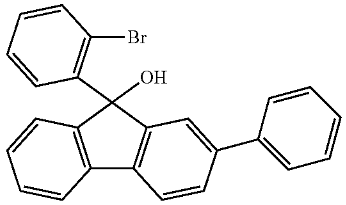 1e | 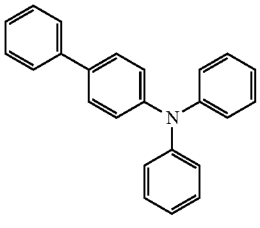 [4432-94-4432-94-4] | 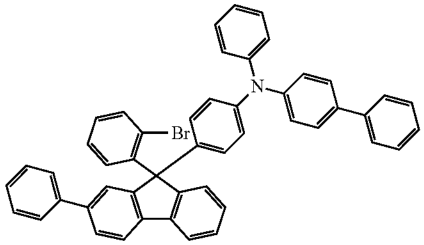 2w | 78% |
| 2x | 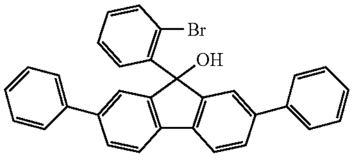 1f | 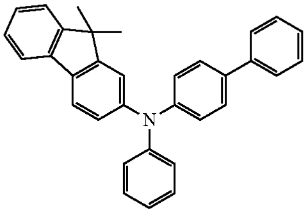 [1391737-67-9] | 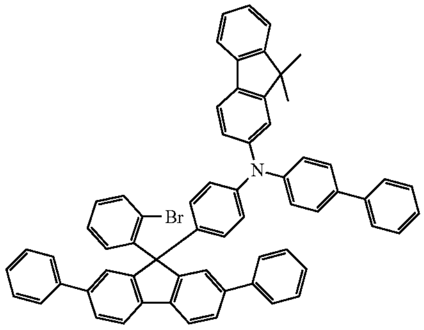 2x | 82% |
| 2y | 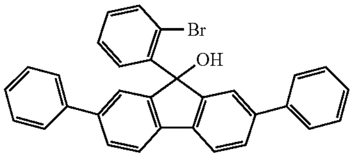 1f | 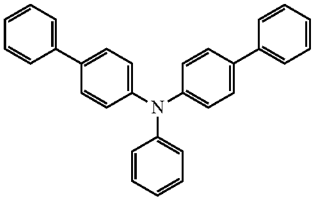 [122215-84-3] | 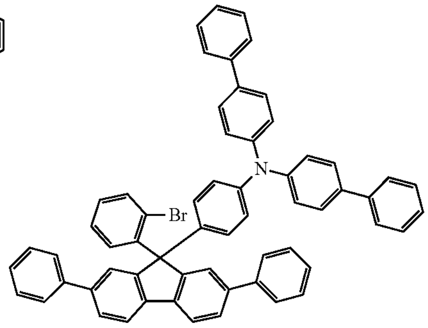 2y | 70% |

-continued
| Ex. | Reactant 1 | Reactant 2 | Product: | Yield |
|---|---|---|---|---|
| 2z | 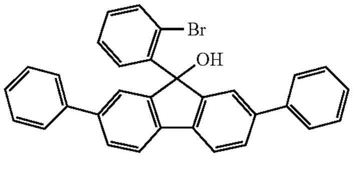 1f | 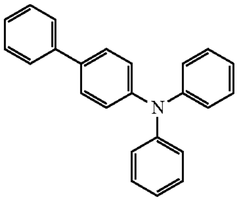 [4432-94-4] | 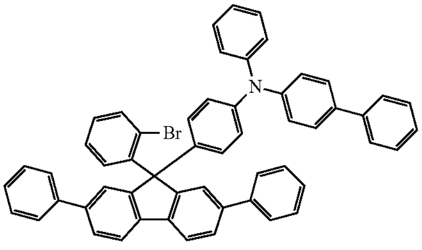 2z | 78% |
| 2aa | 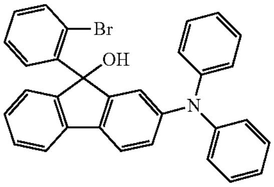 1g | 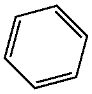 [71-43-2] | 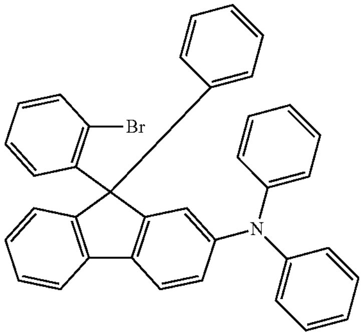 2aa | 61% |
| 2bb | 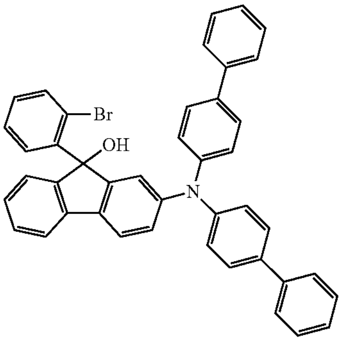 1h | 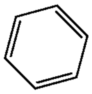 [71-43-2] | 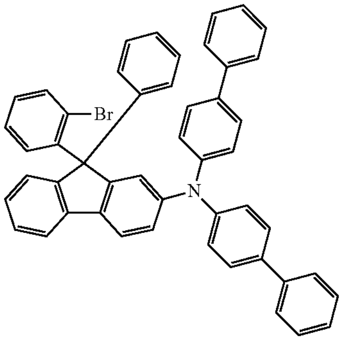 2bb | 56% |
| 2cc | 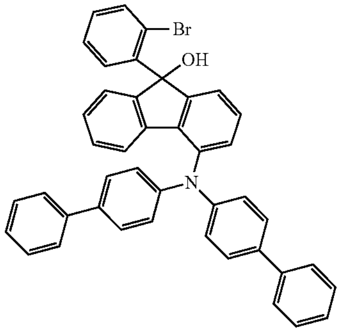 1i | 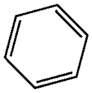 [71-43-2] | 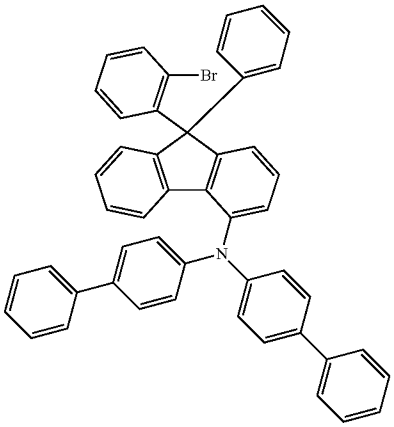 2cc | 64% |

-continued
| Ex. | Reactant 1 | Reactant 2 | Product: | Yield |
|---|---|---|---|---|
| 2dd | 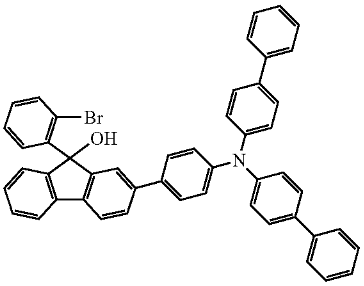 1j | 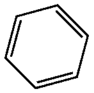 [71-43-2] | 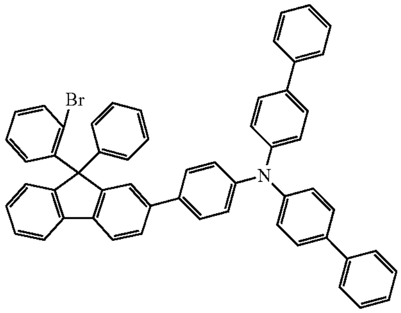 2dd | 42% |
| 2ee | 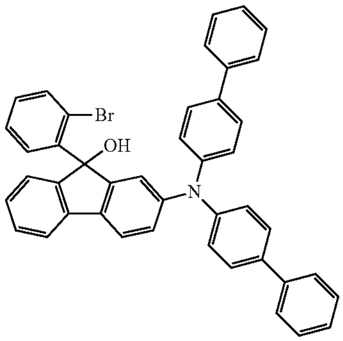 1h | 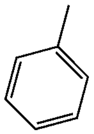 [108-88-3] | 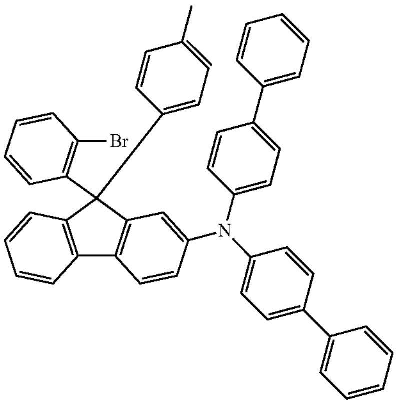 2ee | 56% |
Example 3: 4-Biphenyl-2-(9,9'-dimethylfluorenyl)amino-3-cyanobenzene
-continued
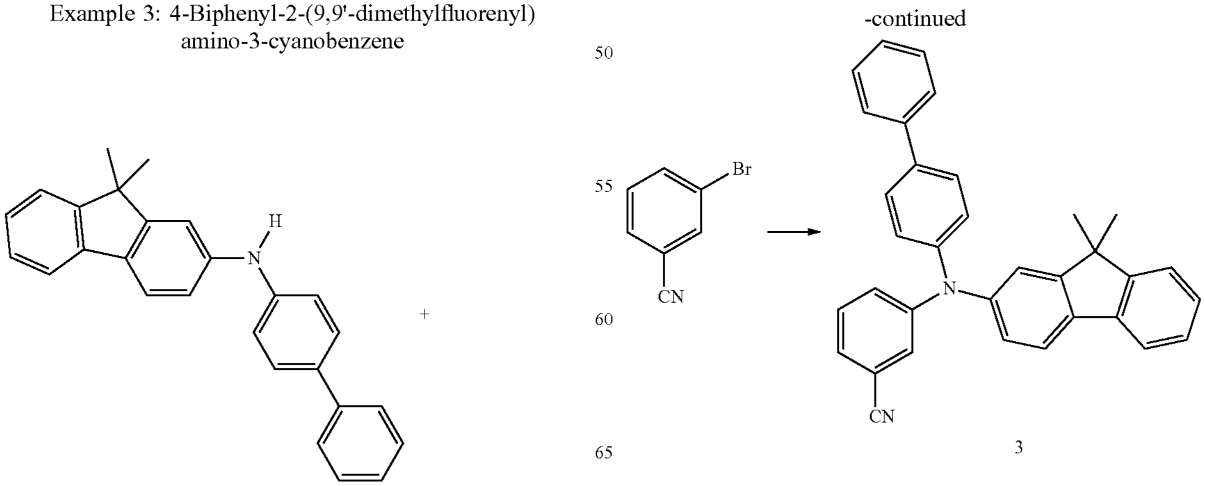
3

A mixture of 9.1 g (50 mmol) of 1-bromo-3-cyanobenzene, 21.7 g (60 mmol) of 4-biphenyl-2-(9,9'-dimethylfluorenyl)amine, [897671-69-1], 7.7 g (80 mmol) of sodium tert-butoxide, 1.4 g (5 mmol) of tricyclohexylamine, 561 mg (2.5 mmol) of palladium(II) acetate and 300 mL of mesitylene is heated under reflux for 24 h. After cooling, 200 mL of water are added, the mixture is stirred for a further 30 min, the organic phase is removed and the latter is filtered through a short Celite bed and then the solvent is removed under reduced pressure. The residue is recrystallized five times from heptane. Yield: 16.8 g (36.5 mmol), 73%; purity about 98% by $^1$H NMR.

In an analogous manner, the following compounds are obtained:

| Ex. | Reactant 1 | Reactant 2 | Product | Yield |
|---|---|---|---|---|
| 3a | 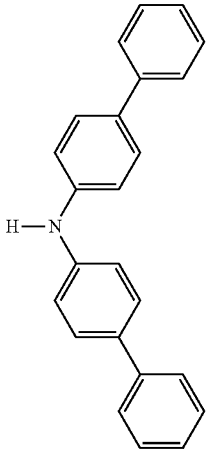 [102113-98-4] | 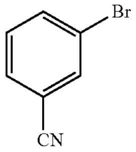 [6952-59-6] | 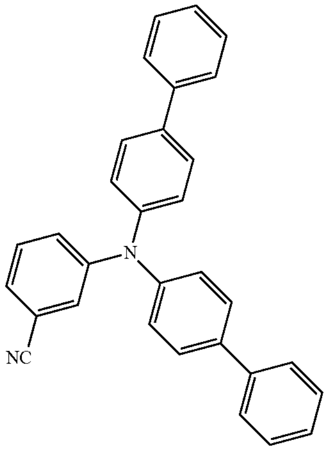 3a | 43% |
| 3b | 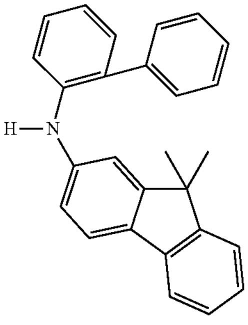 [1198395-24-2] | 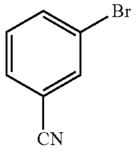 [6952-59-6] | 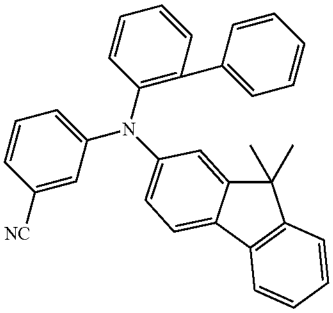 3b | 56% |
| 3c | 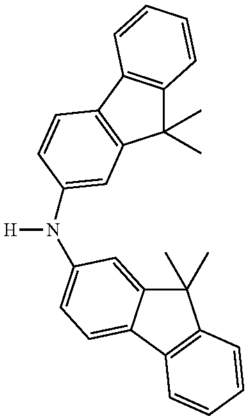 [500717-23-7] | 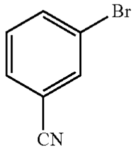 [6952-59-6] | 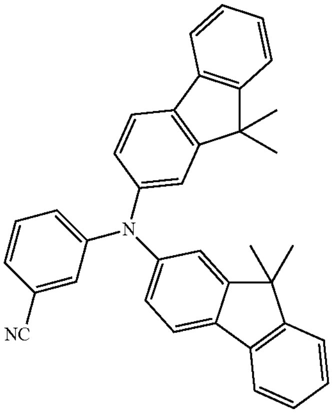 3c | 45% |

-continued
| Ex. | Reactant 1 | Reactant 2 | Product | Yield |
|---|---|---|---|---|
| 3d | 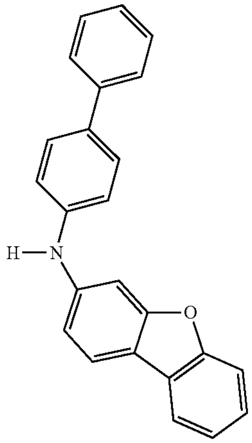 [1290039-85-8] | 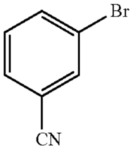 [6952-59-6] | 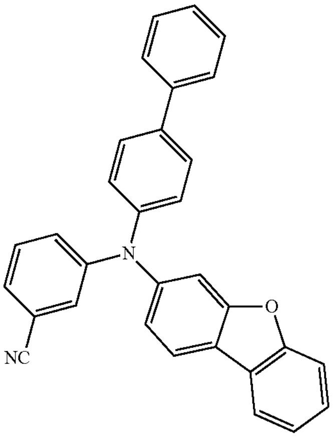 3d | 40% |
| 3e | 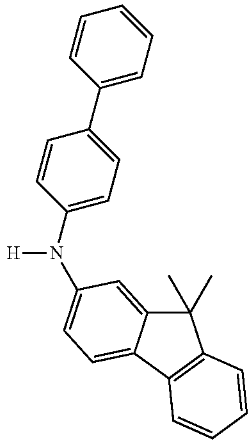 [897671-69-1] | 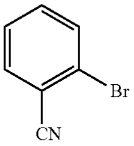 [2042-37-7] | 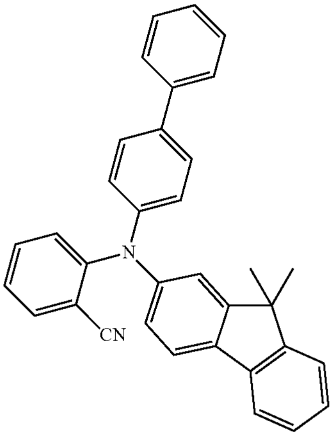 3e | 35% |
| 3f | 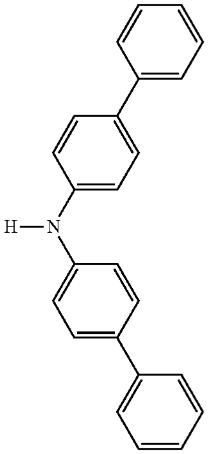 [102113-98-4] | 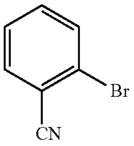 [2042-37-7] | 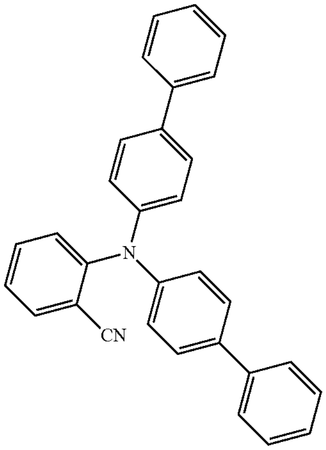 3f | 43% |

-continued
| Ex. | Reactant 1 | Reactant 2 | Product | Yield |
|---|---|---|---|---|
| 3g | 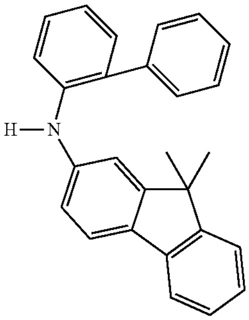 [1198395-24-2] | 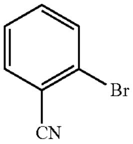 [2042-37-7] | 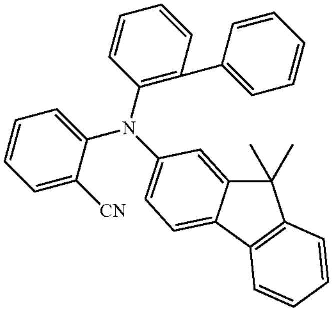 3g | 56% |
| 3h | 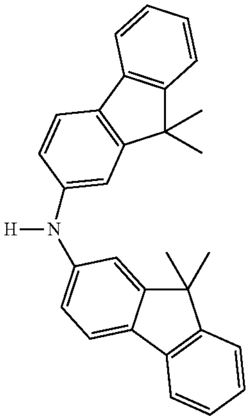 [500717-23-7] | 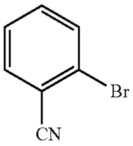 [2042-37-7] | 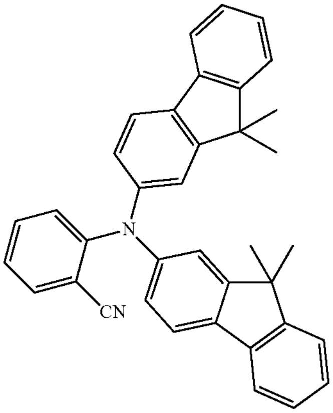 3h | 45% |
| 3i | 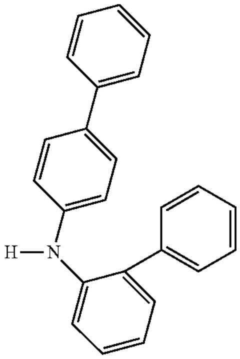 [SMILES: c1ccc(-c2ccc(Nc3ccccc3-c3ccccc3)cc2)cc1] | 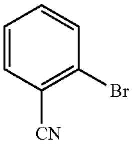 [2042-37-7] | 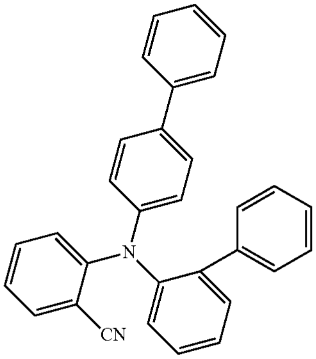 3i | 40% |

Example 4: {3-[Biphenyl-4-yl-(9,9-dimethyl-9H-fluoren-2-yl)amino]phenyl}-(2-bromophenyl)methanone

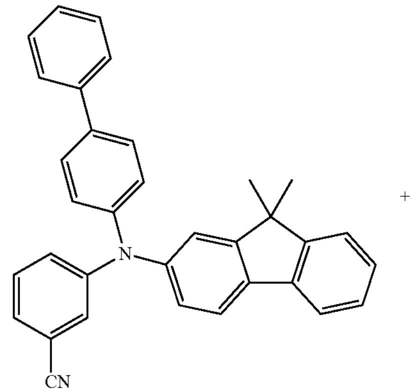

3

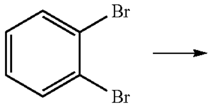

-continued

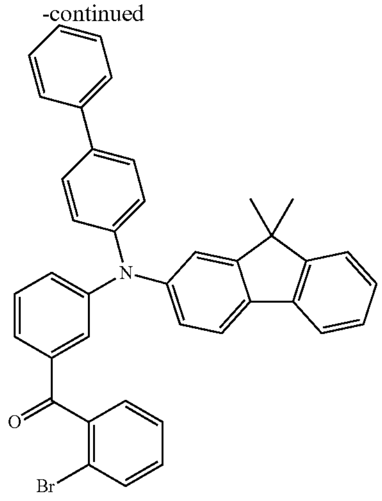

4

2.68 g (110 mmol) of iodine-activated magnesium turnings and a mixture of 25.9 g (110 mmol) of 1,2-dibromobenzene, 0.8 mL of 1,2-dichloroethane, 50 mL of 1,2-dimethoxyethane, 500 mL of THF are used to prepare the corresponding Grignard reagent by trace heating with an oil bath at 70° C. Once the magnesium has reacted fully, the mixture is cooled to room temperature and then a solution of 46.2 g (100 mmol) of 4-biphenyl-2-(9,9'-dimethylfluorenyl)amino-3-cyanobenzene in 300 mL of THF is added dropwise, and the reaction mixture is heated to 50° C. for 4 h and then stirred at room temperature for a further 12 h. 100 mL of water are added, the mixture is stirred briefly, the organic phase is removed and the solvent is removed under reduced pressure. Subsequently, the residue is stirred with 500 mL of MNP and 5 mL of acetic acid at 80° C. for 6 h. After cooling, the precipitated solids are filtered off with suction and washed once with 100 mL of heptane and twice with 100 mL each time of ethanol, and finally recrystallized from dioxane/EtOH. Yield: 26.6 g (43 mmol), 39%; purity about 98% by $^{1}H$ NMR.

In an analogous manner, the following compounds are obtained:

| Ex. | Reactant 1 | Product | Yield |
|---|---|---|---|
| 4a | 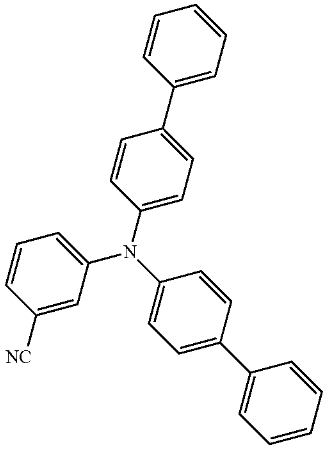 3a | 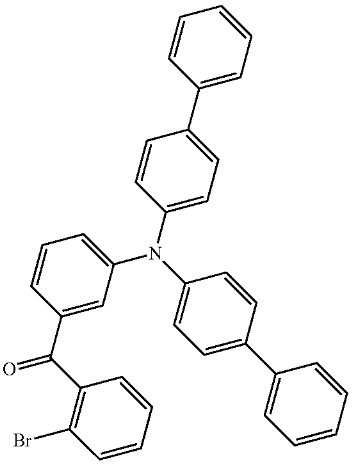 4a | 43% |

-continued
| Ex. | Reactant 1 | Product | Yield |
| --- | --- | --- | --- |
| 4b | 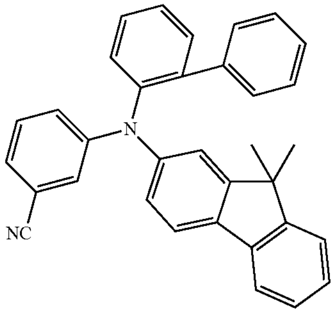 3b | 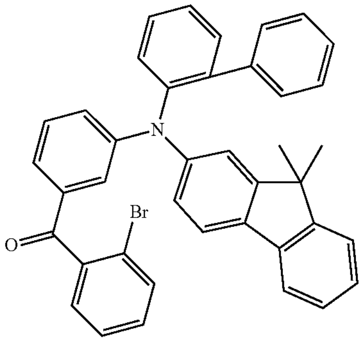 4b | 46% |
| 4c | 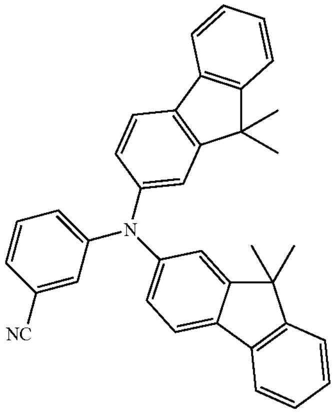 3c | 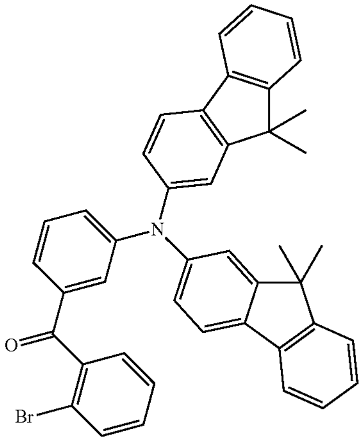 4c | 45% |
| 4d | 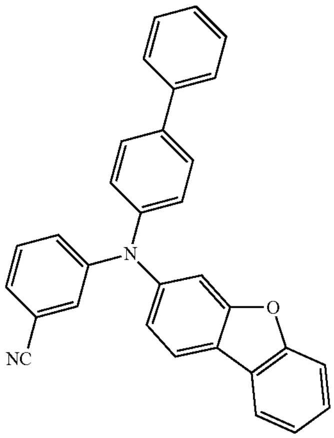 3d | 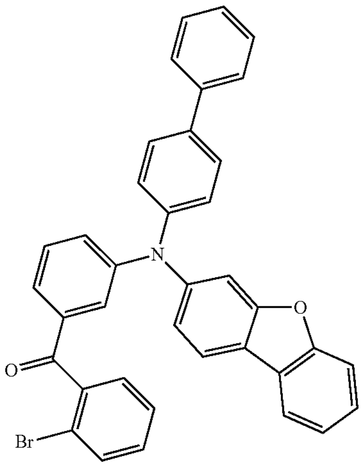 4d | 40% |

-continued
| Ex. | Reactant 1 | Product | Yield |
| --- | --- | --- | --- |
| 4e | 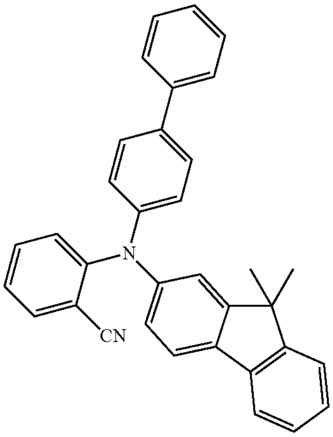 3e | 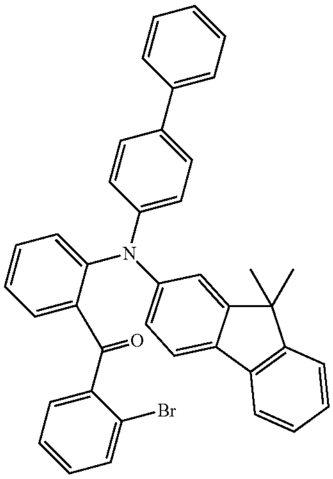 4e | 35% |
| 4f | 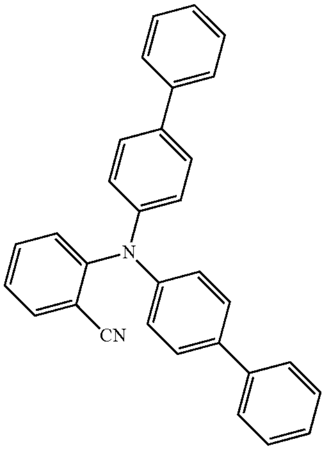 3f | 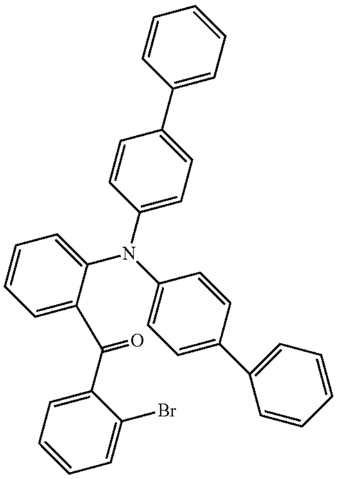 4f | 38% |

-continued
| Ex. | Reactant 1 | Product | Yield |
|---|---|---|---|
| 4g | 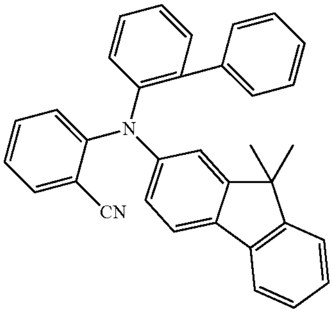 3g | 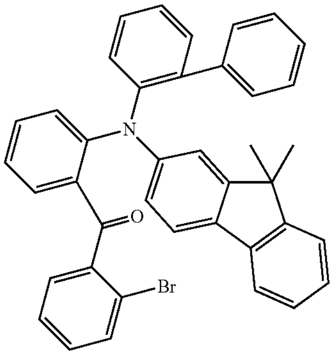 4g | 56% |
| 4h | 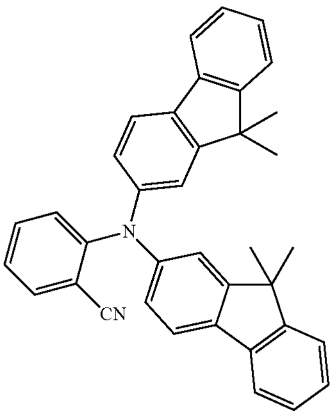 3h | 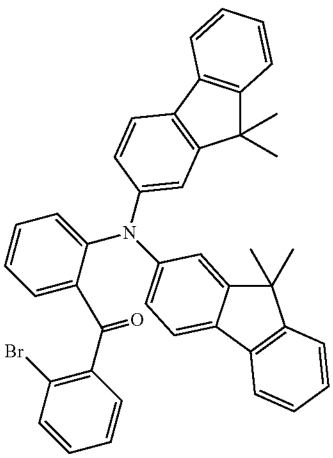 4h | 45% |

-continued

| Ex. | Reactant 1 | Product | Yield |
| --- | --- | --- | --- |
| 4i | 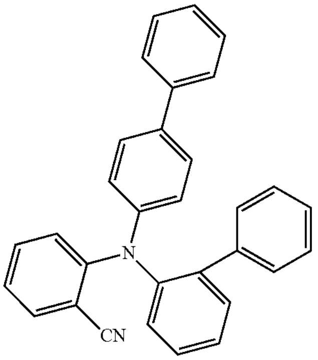 3i | 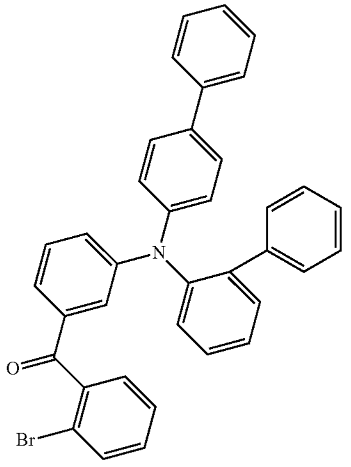 4i | 40% |

Example 5: Biphenyl-4-yl-{3-[9-(2-bromophenyl)-9H-fluoren-9-yl]phenyl}-(9,9-dimethyl-9H-fluoren-2-yl)amine

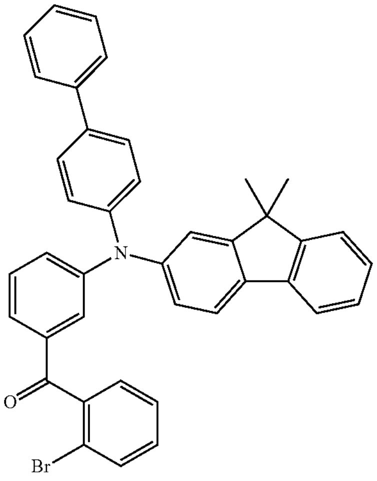

4

+

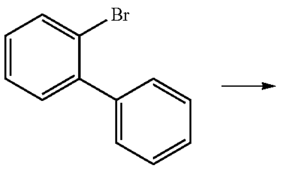

-continued

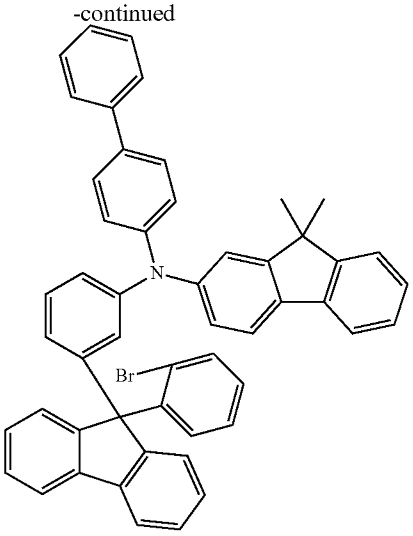

5

1.4 g (55 mmol) of iodine-activated magnesium turnings and a mixture of 12.9 g (55 mmol) of 2-bromobiphenyl, 0.8 mL of 1,2-dichloroethane, 50 mL of 1,2-dimethoxyethane, 300 mL of THF and 200 mL of toluene are used to prepare the corresponding Grignard reagent by trace heating with an oil bath at 70° C. Once the magnesium has reacted fully, the mixture is cooled to room temperature and then a solution of 31.1 g (50 mmol) of {3-[biphenyl-4-yl-(9,9-dimethyl-9H-fluoren-2-yl)amino]phenyl}-(2-bromophenyl)methanone in 400 mL of THF is added dropwise, and the reaction mixture is heated to 50° C. for 4 h and then stirred at room temperature for a further 12 h. 100 mL of water are added, the mixture is stirred briefly, the organic phase is removed and the solvent is removed under reduced pressure. The residue is suspended in 500 mL of glacial acetic acid heated to 40° C., 0.5 mL of conc. sulfuric acid is added to the suspension and the mixture is then stirred at 100° C. for 4 h. After cooling, the precipitated solid is filtered off with suction and washed once with 100 mL of glacial acetic acid and three times with 100 mL each time of ethanol, and finally recrystallized from dioxane. Yield: 26.9 g (28 mmol), 68%; purity about 98% by $^{1}H$ NMR.

In an analogous manner, the following compounds are obtained:
| Ex. | Reactant 1 | Product | Yield |
| --- | --- | --- | --- |
| 5a | 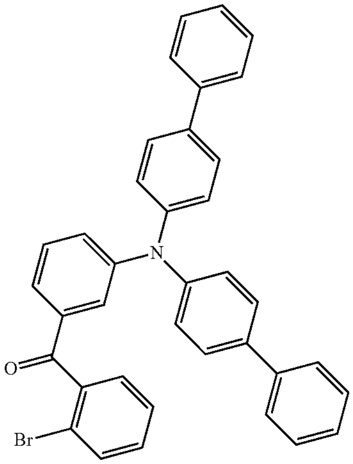 4a | 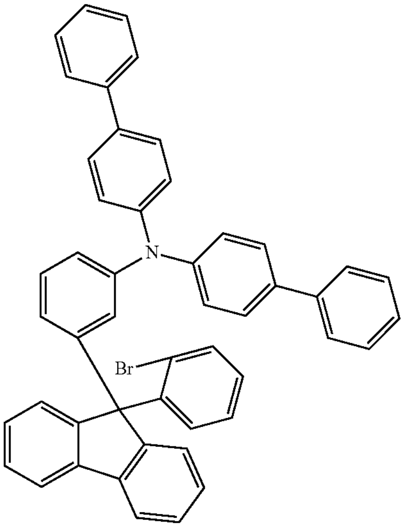 5a | 43% |
| 5b | 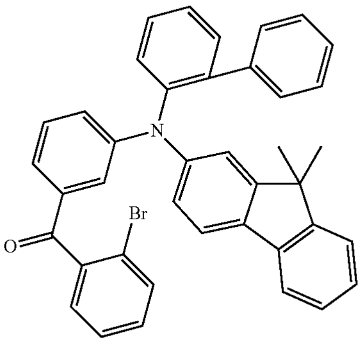 4b | 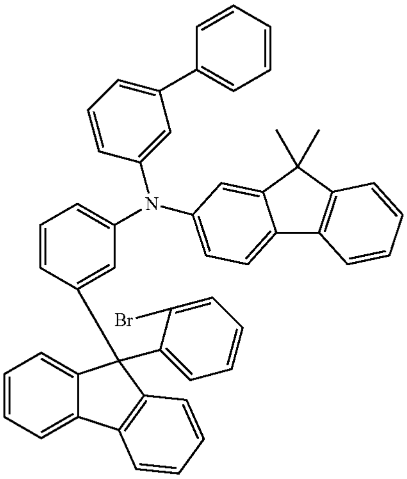 5b | 46% |

-continued
| Ex. | Reactant 1 | Product | Yield |
|---|---|---|---|
| 5c | 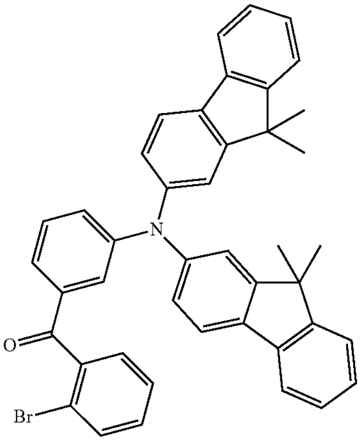 4c | 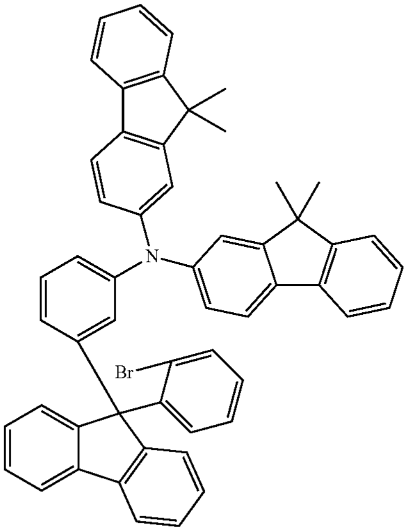 5c | 45% |
| 5d | 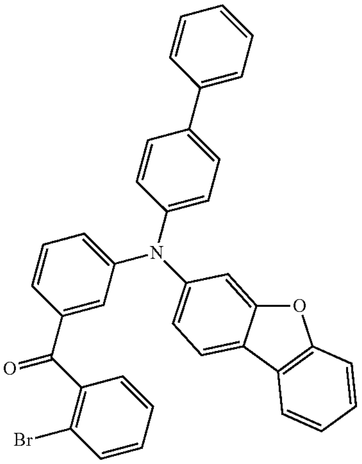 4d | 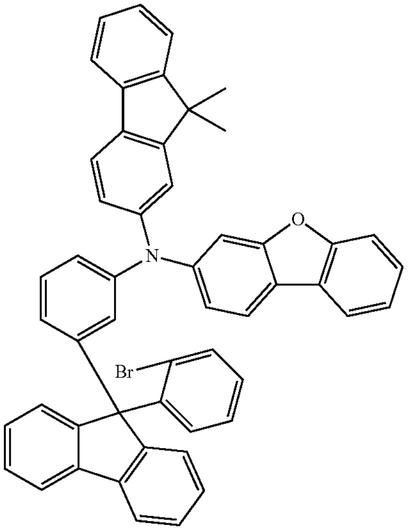 5d | 40% |

-continued
| Ex. | Reactant 1 | Product | Yield |
|---|---|---|---|
| 5e | 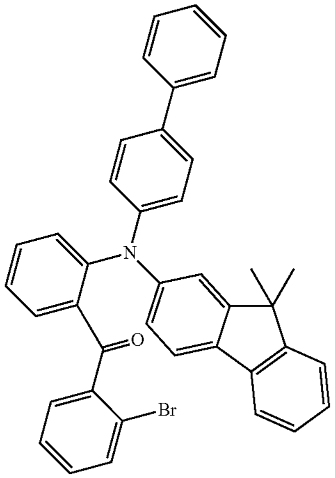 4e | 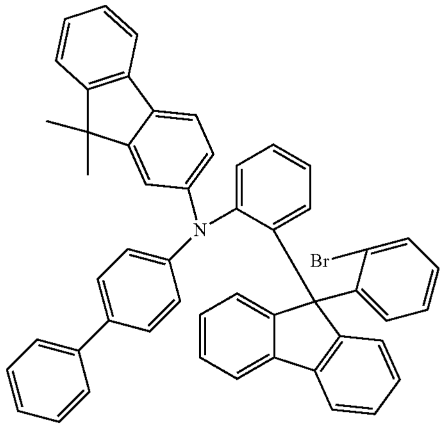 5e | 35% |
| 5f | 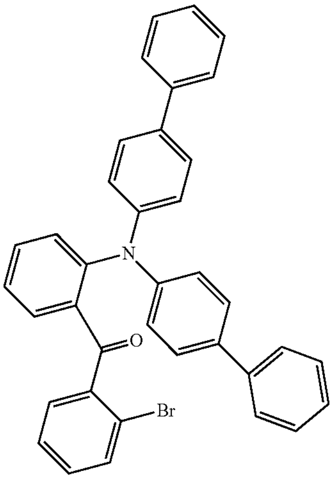 4f | 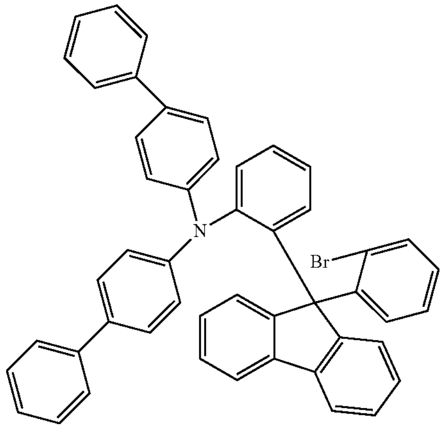 5f | 38% |
| 5g | 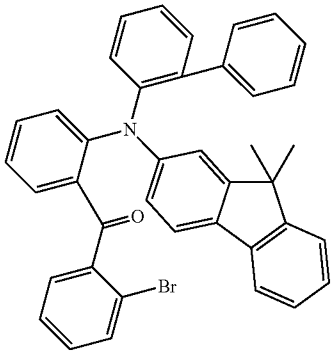 4g | 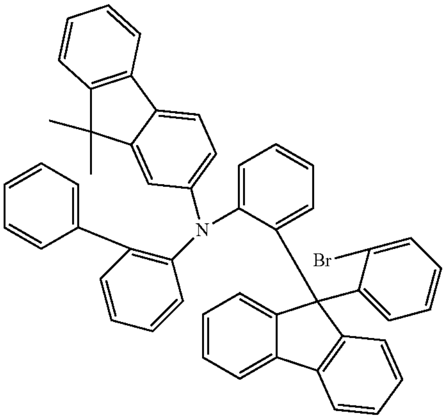 5g | 56% |

-continued
| Ex. | Reactant 1 | Product | Yield |
| --- | --- | --- | --- |
| 5h | 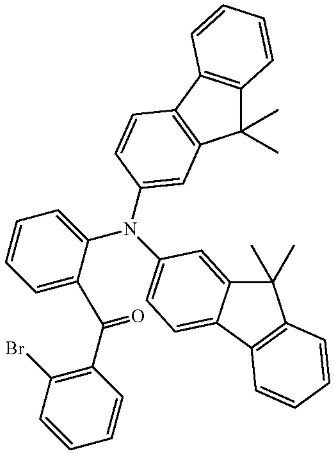 4h | 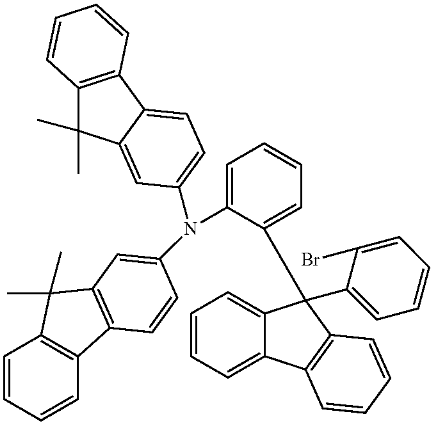 5h | 45% |
| 5i | 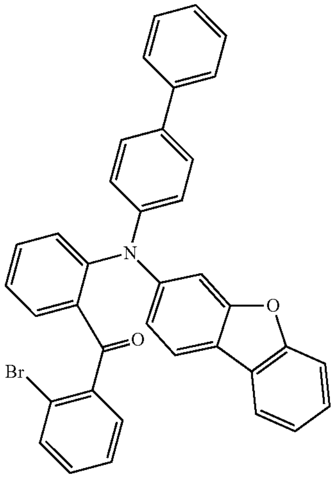 4i | 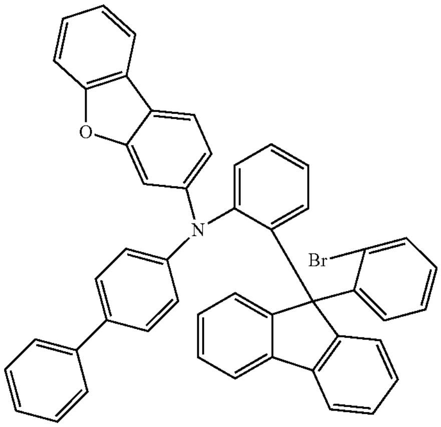 5i | 40% |

-continued

| Ex. | Reactant 1 | Product | Yield |
|---|---|---|---|
| 5g | 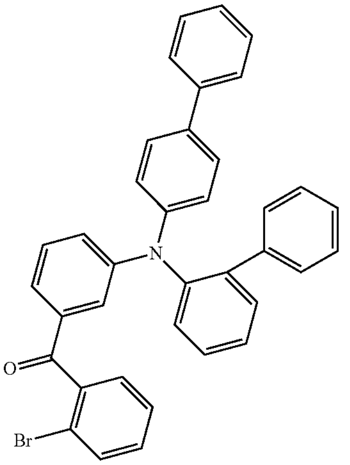 4i | 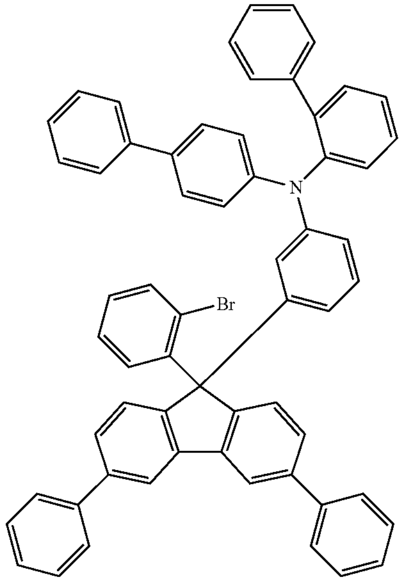 5g | 45% |

Synthesis of Compounds of the Invention

Example 6: Biphenyl-4-yl-(9,9-dimethyl-9H-fluoren-2-yl)-(4-indeno[1,2,3-jk]fluoren-7b-ylphenyl) amine

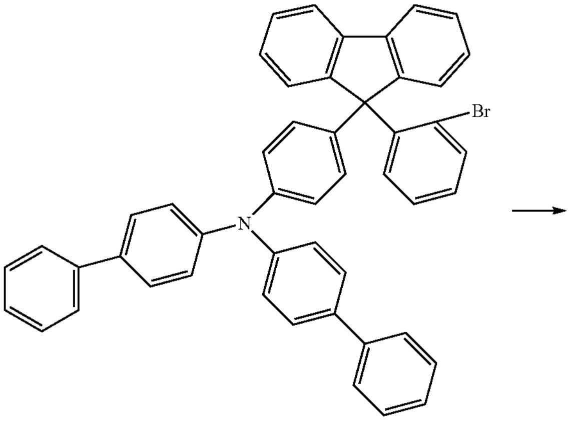

2

-continued

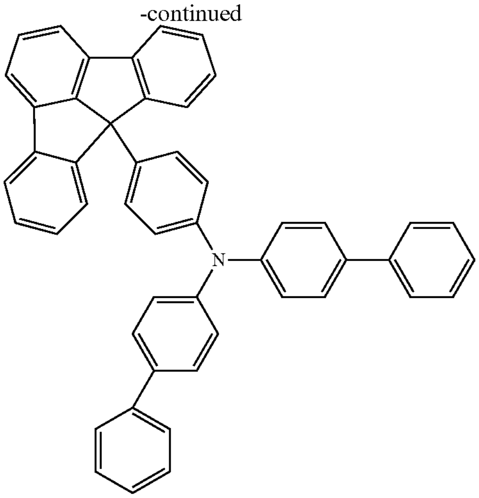

6

A mixture of 38 g (53 mmol) of bis(biphenyl-4-yl){4-[9-(2-bromophenyl)-9H-fluoren-9-yl]phenyl}amine, 2.4 g (20 mmol) of palladium(II) acetate, 5.6 g (21.3 mmol) of triphenylphosphine, 28.14 g (267 mmol) of sodium carbonate, 7.26 g (32 mmol) of benzyltriethylammonium chloride and 500 mL of N,N-dimethylacetamide is heated under reflux for 24 h. After cooling, 200 mL of water are added, the mixture is stirred for a further 30 min, the organic phase is removed and the latter is filtered through a short Celite bed and then the solvent is removed under reduced pressure. The residue is recrystallized five times from DMF/heptane and finally sublimed twice (p about $10^{-6}$ mbar, T=320-330° C.). Yield: 14.5 g (22.8 mmol), 43%; purity: 99.9% by HPLC.

In an analogous manner, the following compounds are obtained:

| Ex. | Reactant | Product | Yield |
| --- | --- | --- | --- |
| 6a | 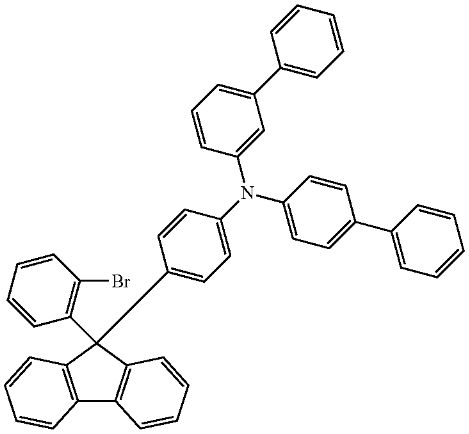 2b | 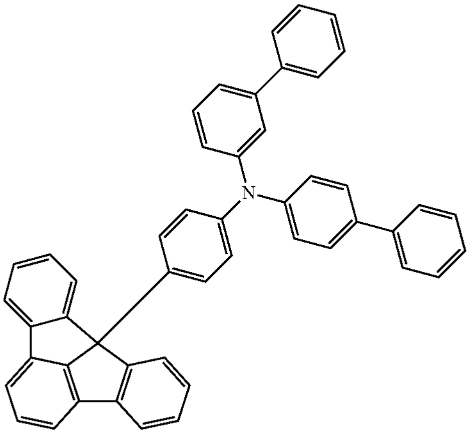 6a | 75% |
| 6b | 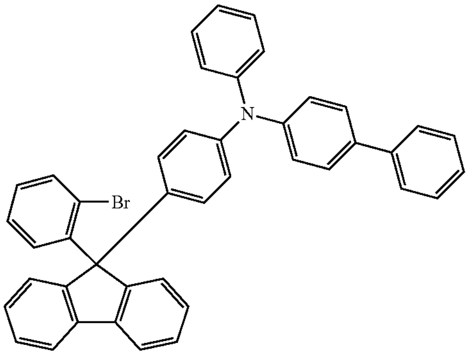 2c | 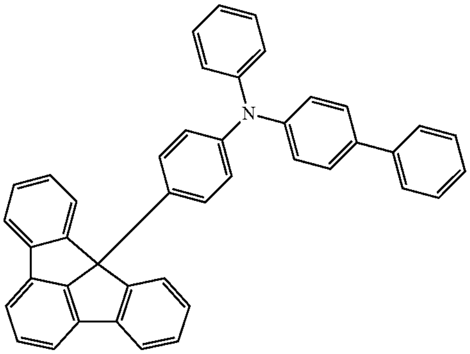 6b | 72% |
| 6d | 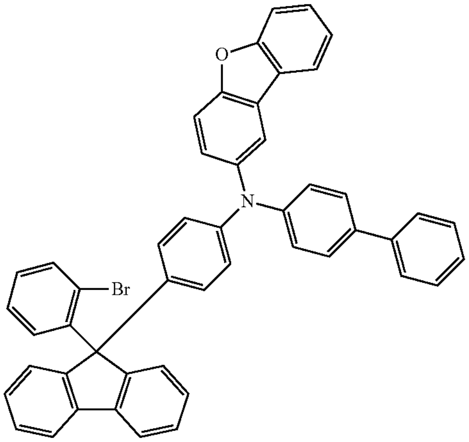 2e | 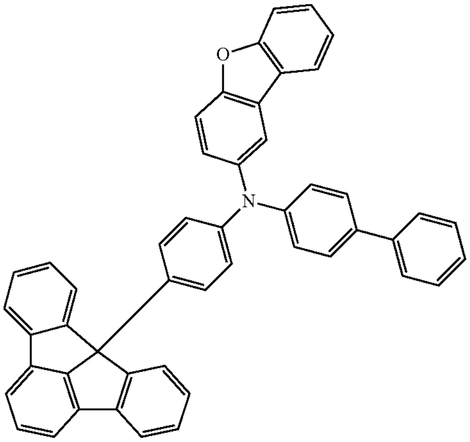 6d | 58% |

-continued
| Ex. | Reactant | Product | Yield |
|---|---|---|---|
| 6e | 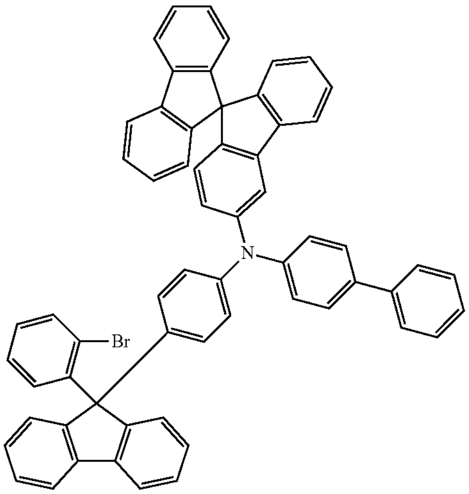 2f | 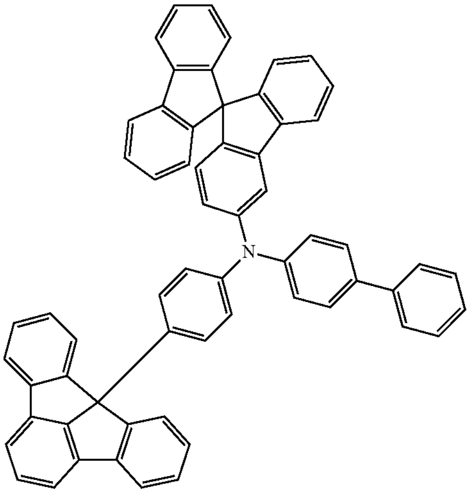 6e | 48% |
| 6f | 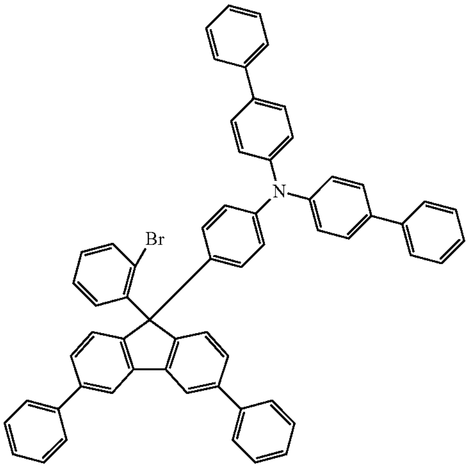 2o | 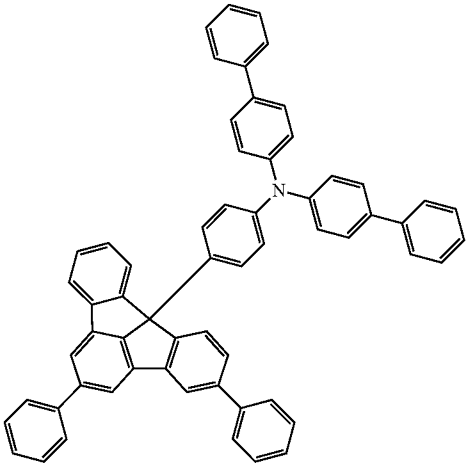 6f | 63% |

-continued
| Ex. | Reactant | Product | Yield |
|---|---|---|---|
| 6g | 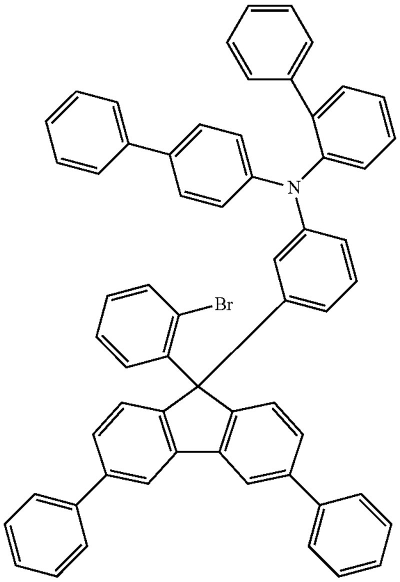 5g | 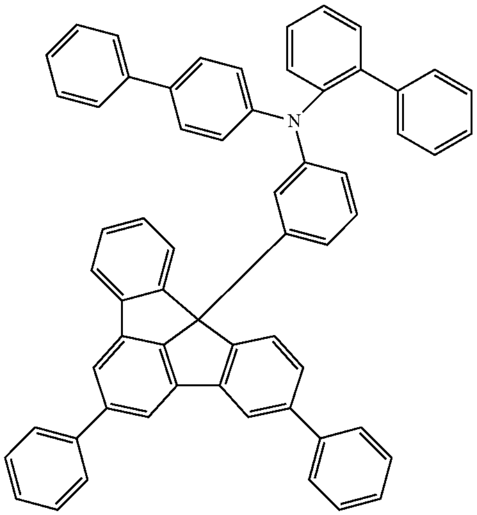 6g | 41% |
| 6h | 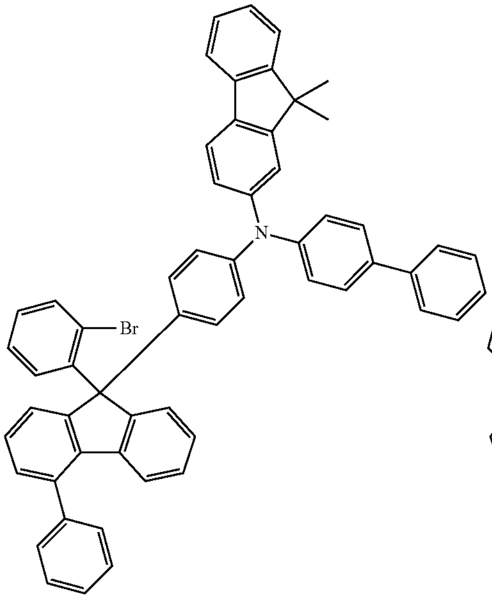 2r | 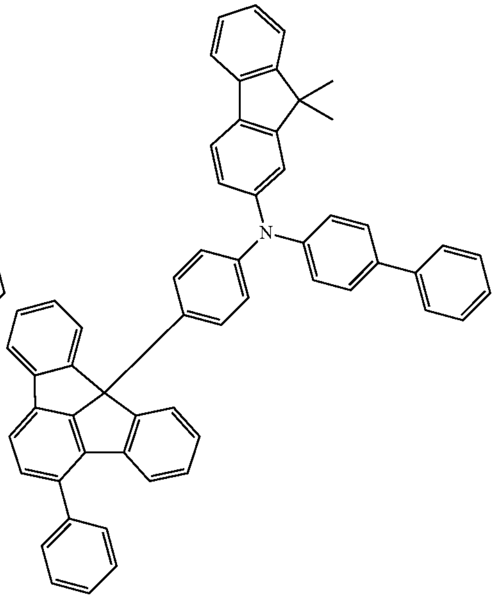 6h | 32% |

-continued
| Ex. | Reactant | Product | Yield |
|---|---|---|---|
| 6j | 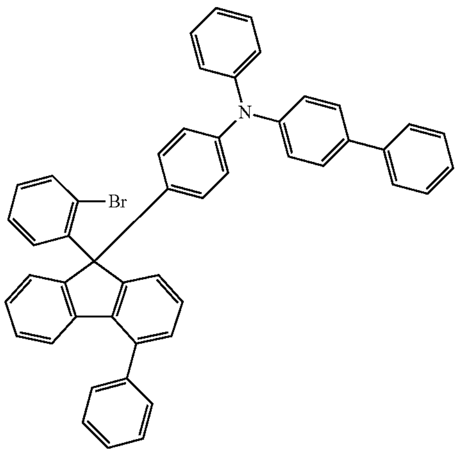 2t | 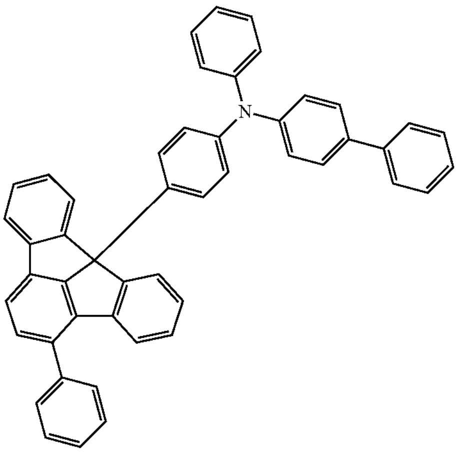 6j | 34% |
| 6k | 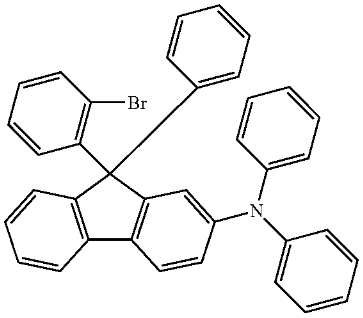 2aa | 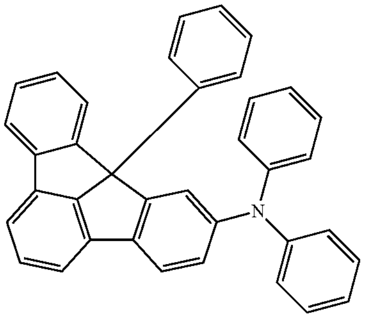 6k | 40% |
| 6l | 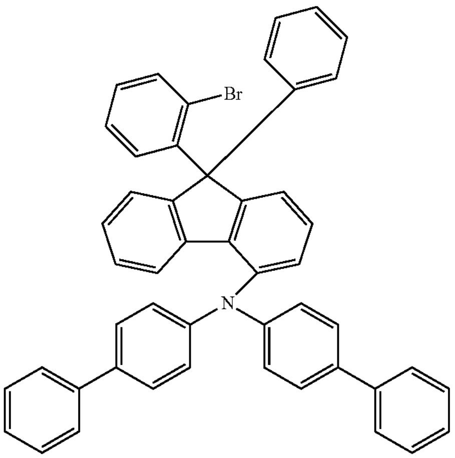 2cc | 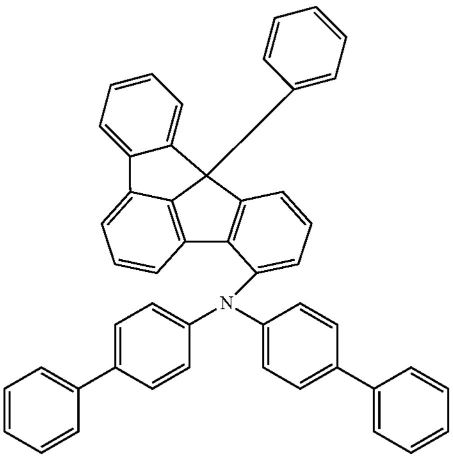 6l | 50% |

-continued
| Ex. | Reactant | Product | Yield |
|---|---|---|---|
| 6m | 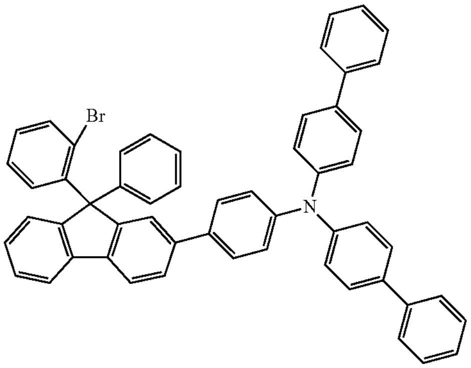 2dd | 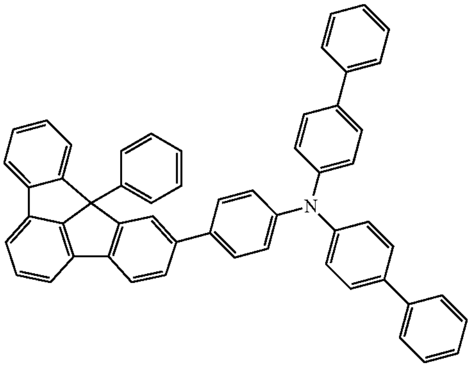 6m | 34% |
| 6n | 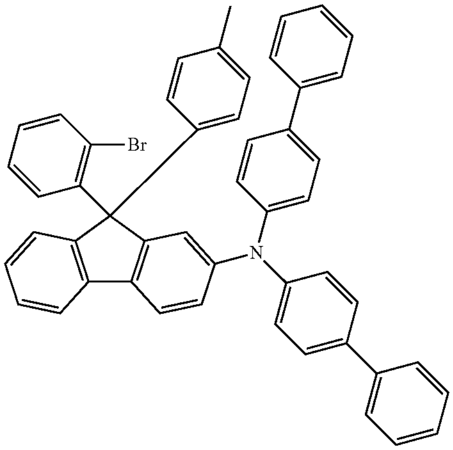 2ee | 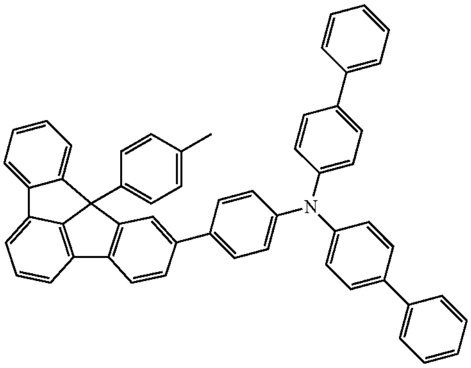 6n | 45% |
| 6o | 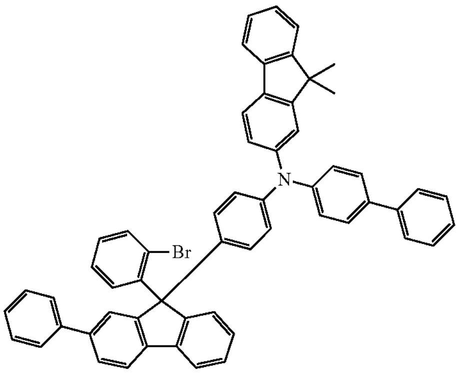 2u | 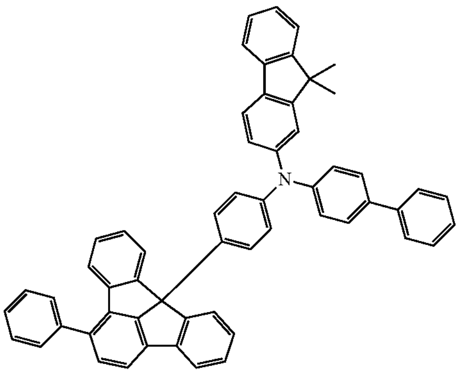 6o | 47% |

-continued
| Ex. | Reactant | Product | Yield |
|---|---|---|---|
| 6p | 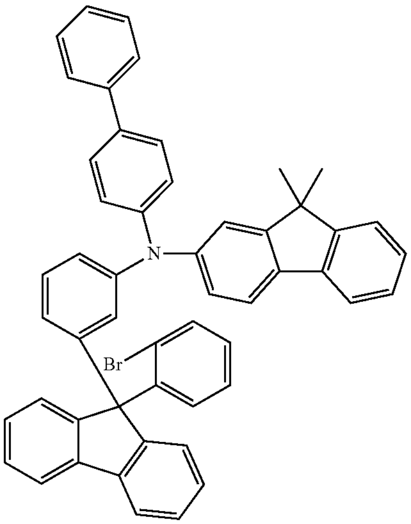 5 | 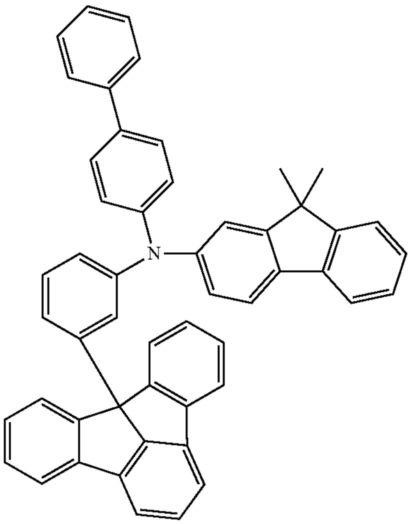 6p | 74% |
| 6r | 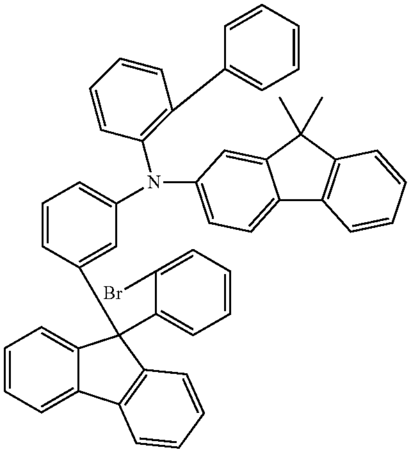 5b | 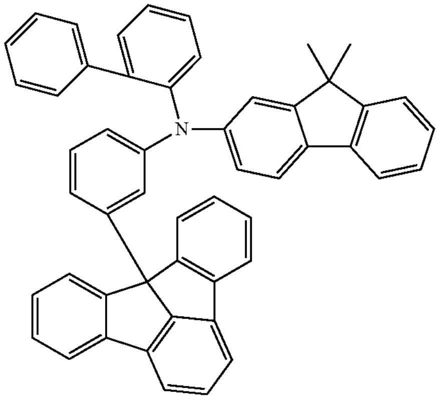 6r | 63% |
| 6s | 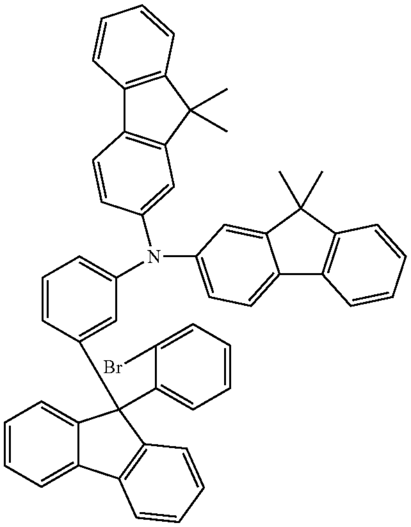 5c | 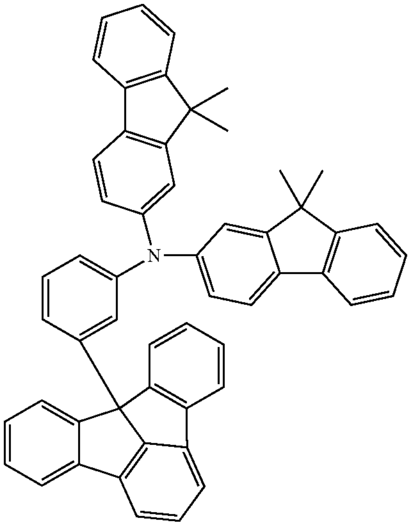 6s | 59% |

-continued
| Ex. | Reactant | Product | Yield |
| --- | --- | --- | --- |
| 6t | 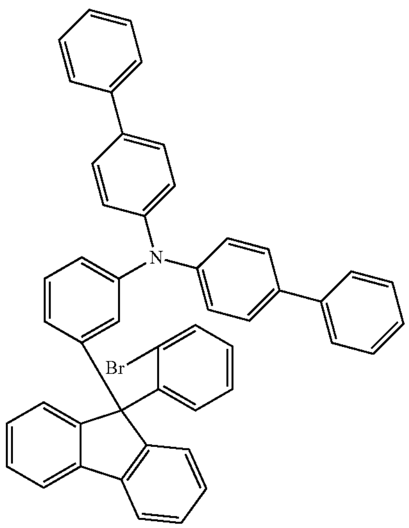 5a | 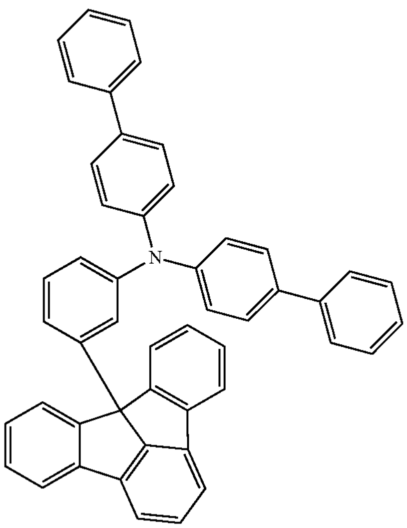 6t | 62% |
| 6u | 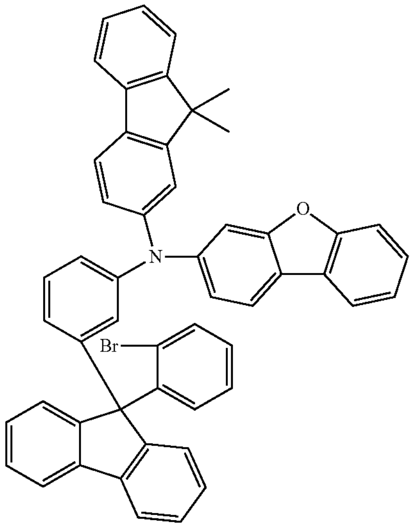 5d | 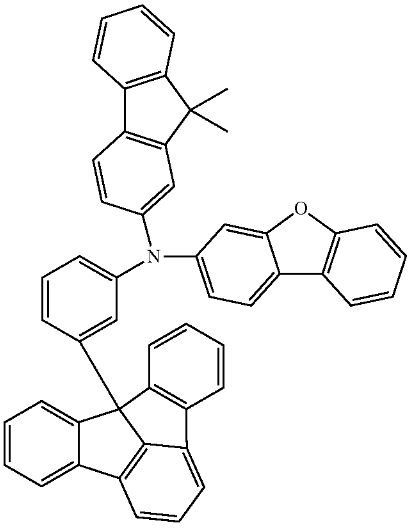 6u | 47% |

-continued
| Ex. | Reactant | Product | Yield |
|---|---|---|---|
| 6v | 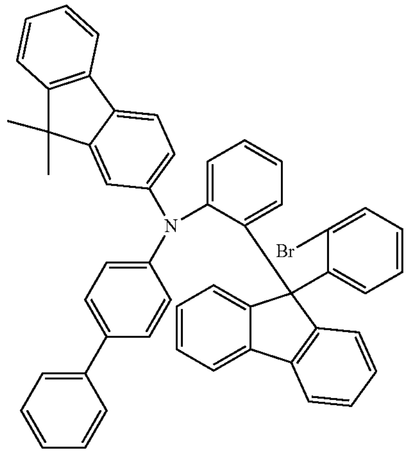 5e | 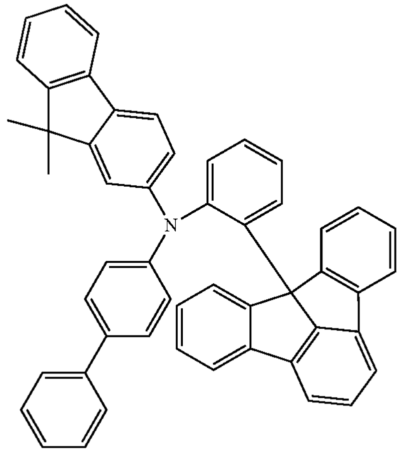 6v | 53% |
| 6w | 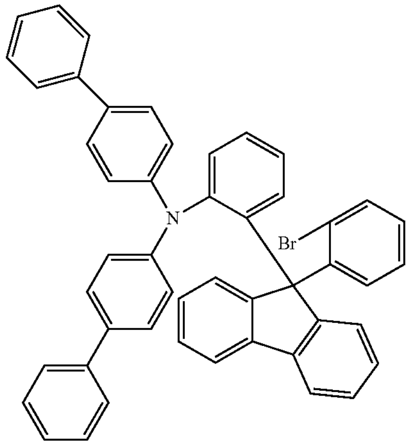 5f | 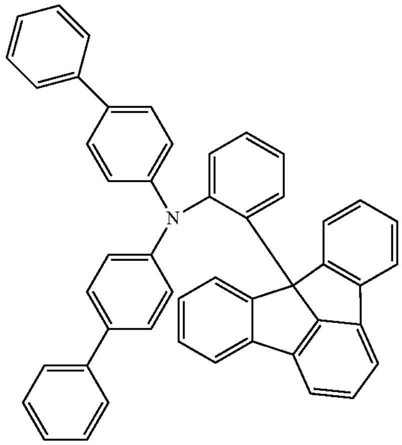 6w | 55% |
| 6x | 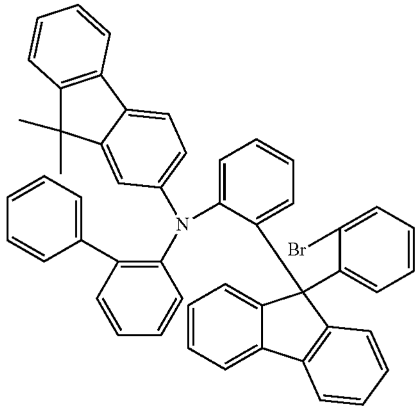 5g | 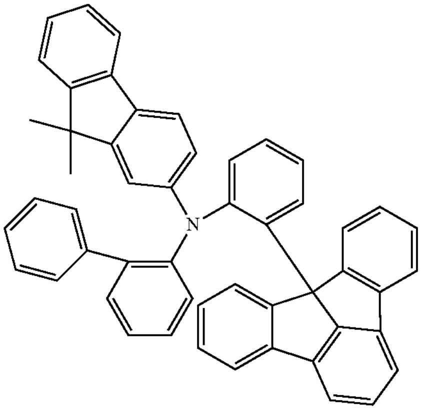 6x | 48% |

-continued
| Ex. | Reactant | Product | Yield |
|---|---|---|---|
| 6y | 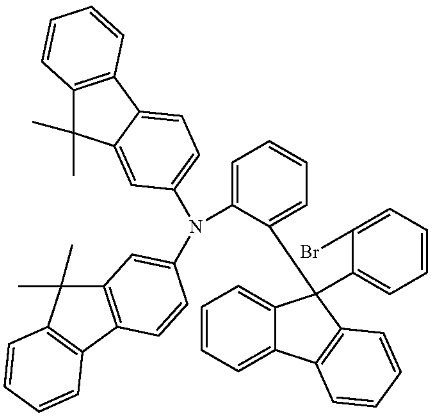 5h | 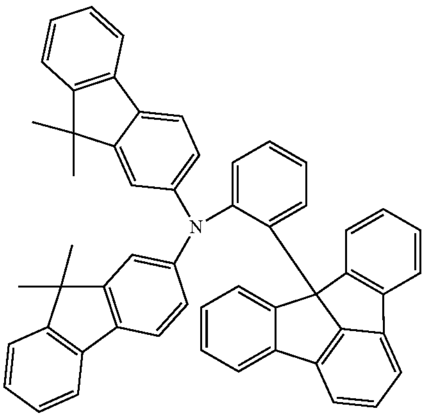 6y | 58% |
| 6z | 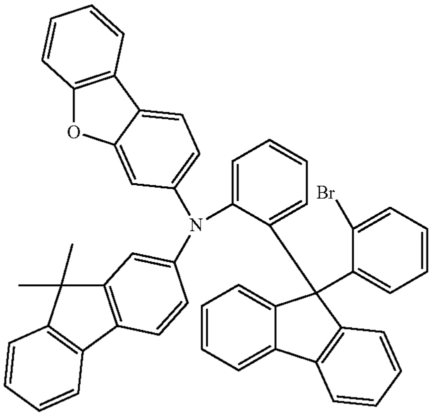 [SMILES: CC1(C)c2ccccc2-c2ccc(N(c3ccc4c(c3)oc3ccccc34)c3ccccc3C3(c4ccccc4Br)c4ccccc4-c4ccccc43)cc21] | 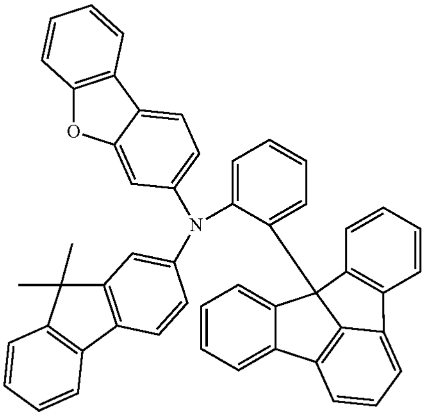 6z | 49% |
| 6aa | 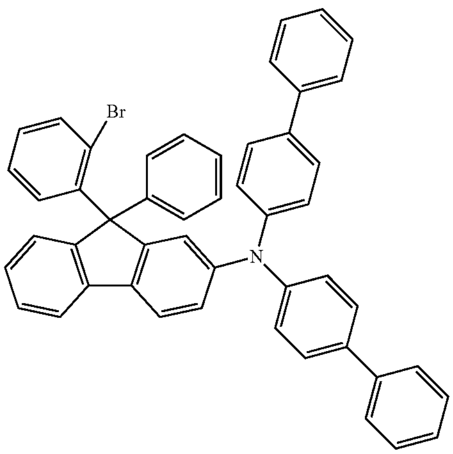 [SMILES: Brc1ccccc1C1(c2ccccc2)c2ccccc2-c2ccc(N(c3ccc(-c4ccccc4)cc3)c3ccc(-c4ccccc4)cc3)cc21] | 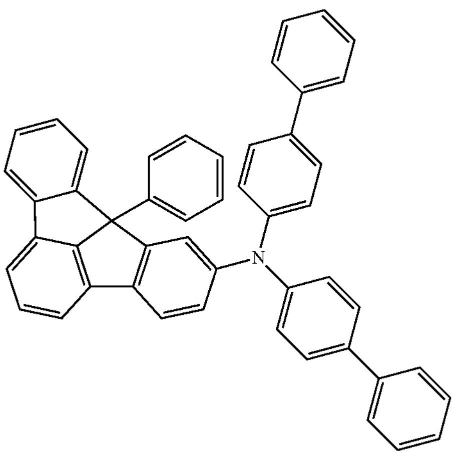 6aa | 34% |

-continued
| Ex. | Reactant | Product | Yield |
| --- | --- | --- | --- |
| 6ab | 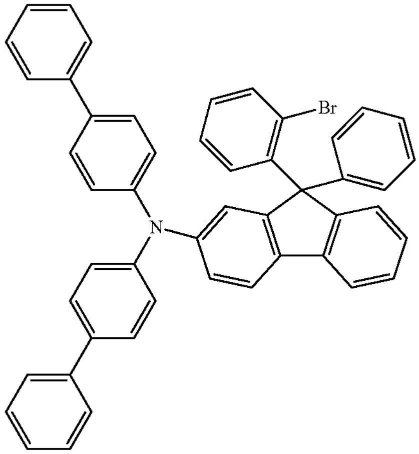 [SMILES: Brc1ccccc1C1(c2ccccc2)c2ccccc2-c2ccc(N(c3ccc(-c4ccccc4)cc3)c3ccc(-c4ccccc4)cc3)cc21] | 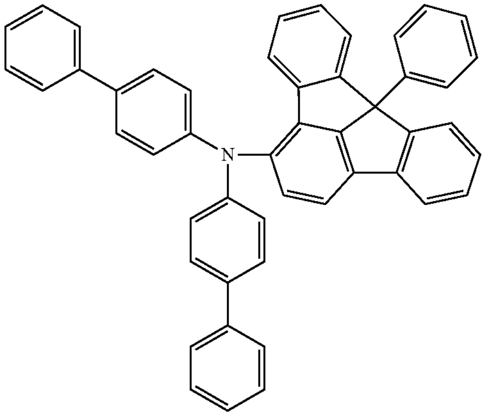 6ab | 36% |
| 6ac | 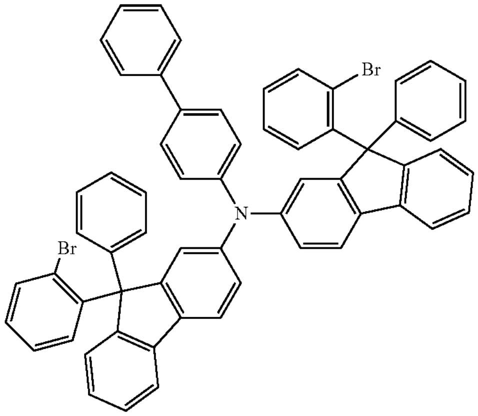 [SMILES: Brc1ccccc1C1(c2ccccc2)c2ccccc2-c2ccc(N(c3ccc(-c4ccccc4)cc3)c3ccc4c(c3)C(c3ccccc3)(c3ccccc3Br)c3ccccc3-4)cc21] | 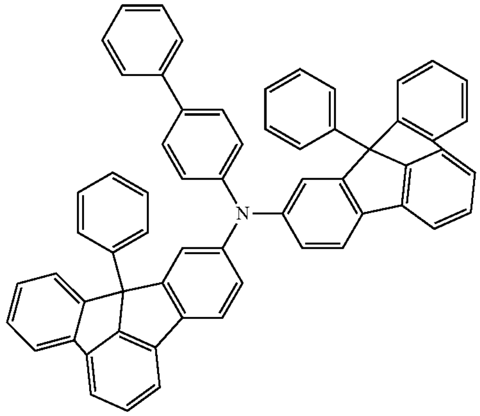 [SMILES: c1ccc(-c2ccc(N(c3ccc4c(c3)C3(c5ccccc5)c5ccccc5-c5cccc-4c53)c3ccc4c(c3)C3(c5ccccc5)c5ccccc5-c5cccc-4c53)cc2)cc1] | 48% |
| 6ad | 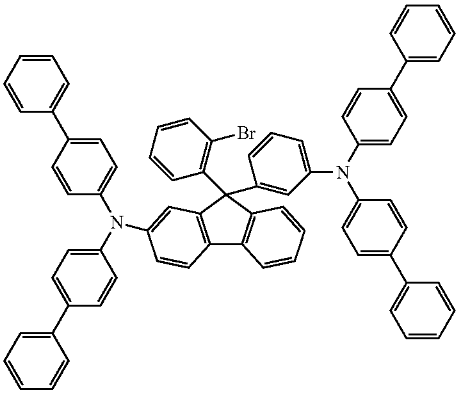 [SMILES: Brc1ccccc1C1(c2cccc(N(c3ccc(-c4ccccc4)cc3)c3ccc(-c4ccccc4)cc3)c2)c2ccccc2-c2ccc(N(c3ccc(-c4ccccc4)cc3)c3ccc(-c4ccccc4)cc3)cc21] | 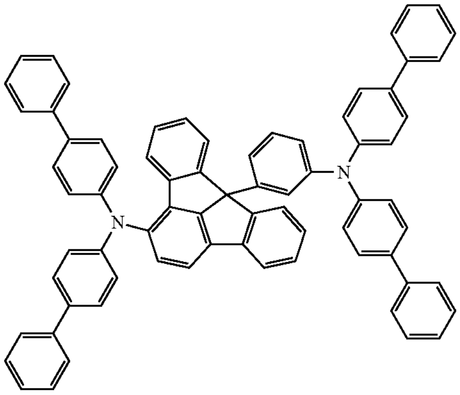 [SMILES: c1ccc(-c2ccc(N(c3ccc(-c4ccccc4)cc3)c3cccc(C45c6ccccc6-c6ccc(N(c7ccc(-c8ccccc8)cc7)c7ccc(-c8ccccc8)cc7)c(c64)-c4ccccc45)c3)cc2)cc1] | 28% |

-continued

| Ex. | Reactant | Product | Yield |
| --- | --- | --- | --- |
| 6ae | 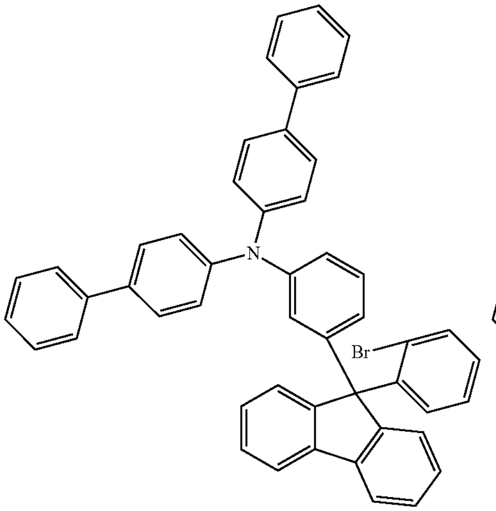 | 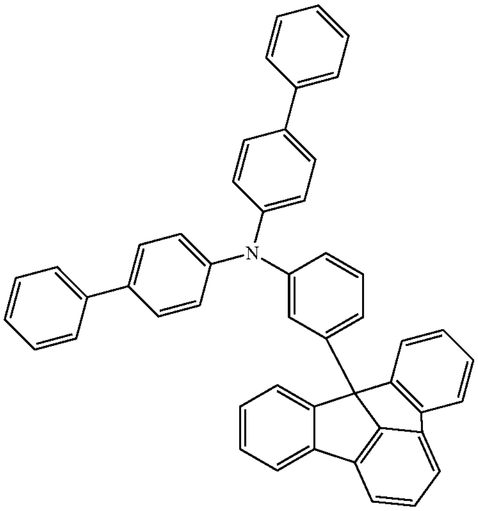 [SMILES: c1ccc(-c2ccc(N(c3ccc(-c4ccccc4)cc3)c3cccc(C45c6ccccc6-c6cccc(c64)-c4ccccc45)c3)cc2)cc1] | 55% |

Part B: Production of the OLEDs

OLEDs of the invention and OLEDs according to the prior art are produced by a general method according to WO 04/058911, which is adapted to the circumstances described here (variation in layer thickness, materials).

In inventive examples I1 to I12 and in reference examples C1 and C2 which follow, the data of various OLEDs are presented. Substrates used are glass plates coated with structured ITO (indium tin oxide) of thickness 50 nm. The OLEDs basically have the following layer structure: substrate/p-doped hole transport layer A' (HIL1)/hole transport layer A (HTL)/p-doped hole transport layer B (HIL2)/hole transport layer C (EBL)/emission layer (EML)/electron transport layer (ETL)/electron injection layer (EIL) and finally a cathode. The cathode is formed by an aluminum layer of thickness 100 nm. The materials required for production of the OLEDs are shown in table 1, and the structure of the various electronic devices produced in table 2.

All materials are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. Details given in such a form as H1:SEB(5%) mean here that the material H1 is present in the layer in a proportion by volume of 95% and SEB in a proportion of 5%. In an analogous manner, the electron transport layer or the hole injection layers may also consist of a mixture of two materials.

The OLEDs are characterized in a standard manner. For this purpose, the electroluminescence spectra, the current efficiency (measured in cd/A), the power efficiency (measured in lm/W) and the external quantum efficiency (EQE, measured in percent) as a function of luminance, calculated from current-voltage-luminance characteristics (IUL characteristics) assuming Lambertian radiation characteristics, and also the lifetime are determined. The electroluminescence spectra are determined at a luminance of 1000 cd/$m^2$, and the CIE 1931 x and y color coordinates are calculated therefrom. The parameter EQE @ 10 mA/$cm^2$ refers to the external quantum efficiency at a current density of 10 mA/$cm^2$. LD80 @ 60 mA/cm2 is the lifetime before the starting brightness of the LED in question, at constant current of 60 mA/$cm^2$, has fallen to 80% of the starting intensity.

TABLE 1

| Structures of the materials used |
| --- |
| 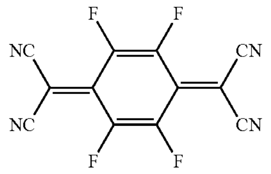 [SMILES: N#CC(C#N)=c1c(F)c(F)c(=C(C#N)C#N)c(F)c1F] |
| F4TCNQ |
| 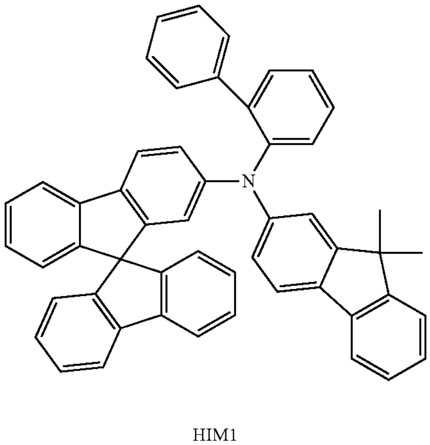 |
| HIM1 |

TABLE 1-continued
| Structures of the materials used |
| --- |
| 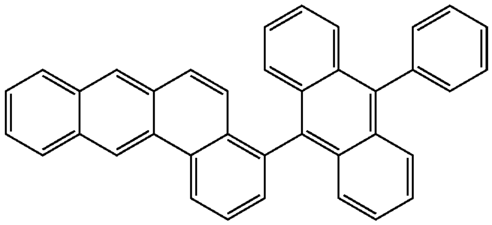 [SMILES: c1ccc(-c2c3ccccc3c(-c3cccc4c3ccc3cc5ccccc5cc34)c3ccccc23)cc1] |
| H1 |
| 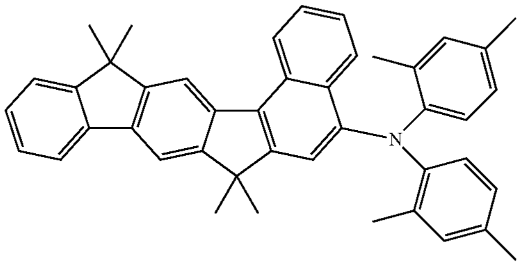 [SMILES: Cc1ccc(N(c2ccc(C)cc2C)c2cc3c(c4ccccc24)-c2cc4c(cc2C3(C)C)-c2ccccc2C4(C)C)c(C)c1] |
| SEB |
| 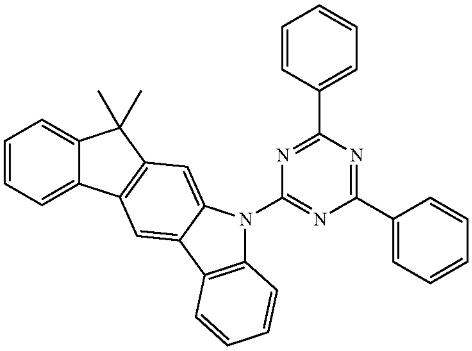 [SMILES: CC1(C)c2ccccc2-c2cc3c4ccccc4n(-c4nc(-c5ccccc5)nc(-c5ccccc5)n4)c3cc21] |
| H2 |
| 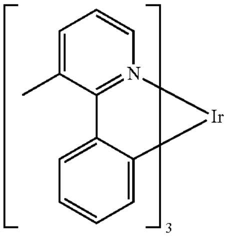 |
| TEG |
TABLE 1-continued
| Structures of the materials used |
| --- |
| 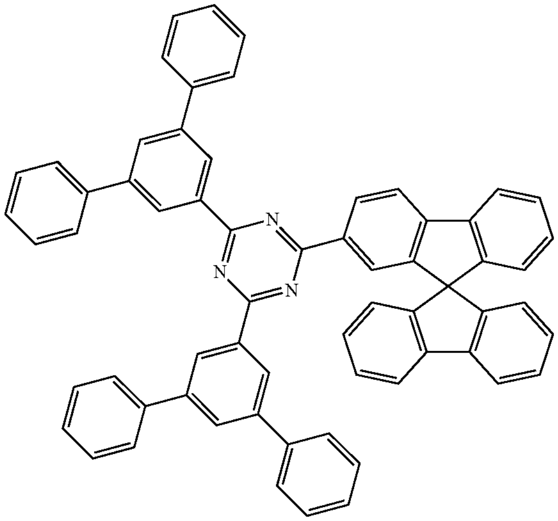 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1] |
| ETM |
| 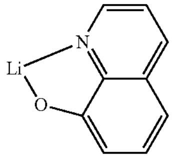 |
| LiQ |
| 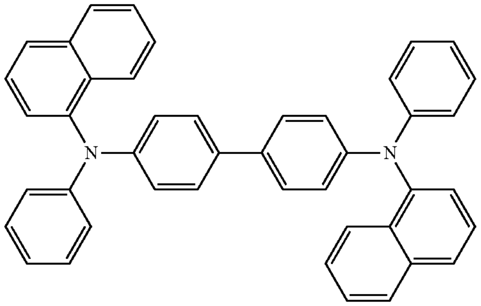 [SMILES: c1ccc(N(c2ccc(-c3ccc(N(c4ccccc4)c4cccc5ccccc45)cc3)cc2)c2cccc3ccccc23)cc1] |
| NPB |

TABLE 1-continued
Structures of the materials used
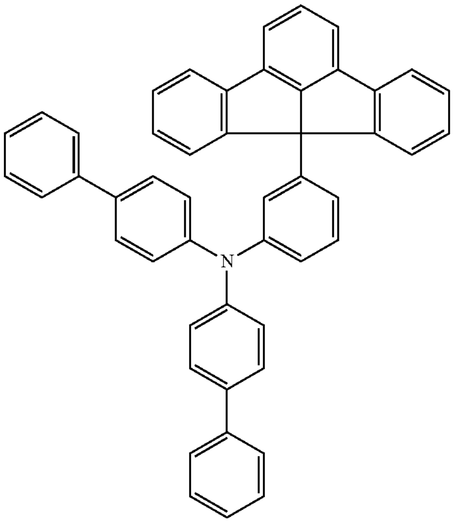 [SMILES: c1ccc(-c2ccc(N(c3ccc(-c4ccccc4)cc3)c3cccc(C45c6ccccc6-c6cccc(c64)-c4ccccc45)c3)cc2)cc1]
HTM1
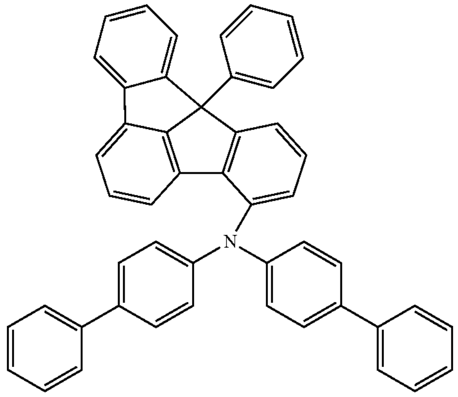 [SMILES: c1ccc(-c2ccc(N(c3ccc(-c4ccccc4)cc3)c3cccc4c3-c3cccc5c3C4(c3ccccc3)c3ccccc3-5)cc2)cc1]
HTM2
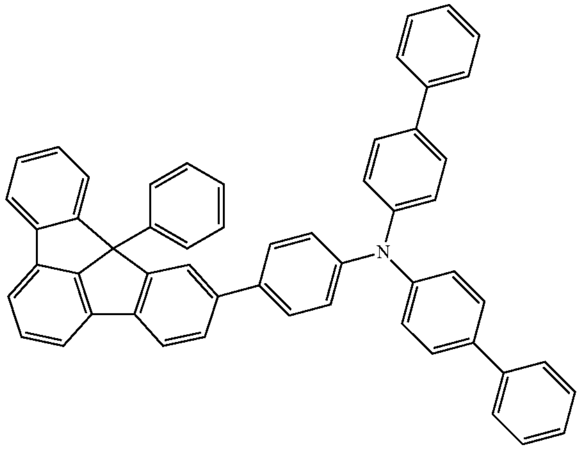 [SMILES: c1ccc(-c2ccc(N(c3ccc(-c4ccccc4)cc3)c3ccc(-c4ccc5c(c4)C4(c6ccccc6)c6ccccc6-c6cccc-5c64)cc3)cc2)cc1]
HTM3
TABLE 1-continued
Structures of the materials used
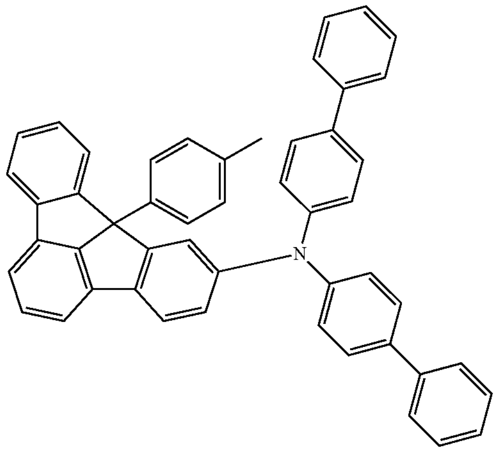 [SMILES: Cc1ccc(C23c4ccccc4-c4cccc(c42)-c2ccc(N(c4ccc(-c5ccccc5)cc4)c4ccc(-c5ccccc5)cc4)cc23)cc1]
HTM4
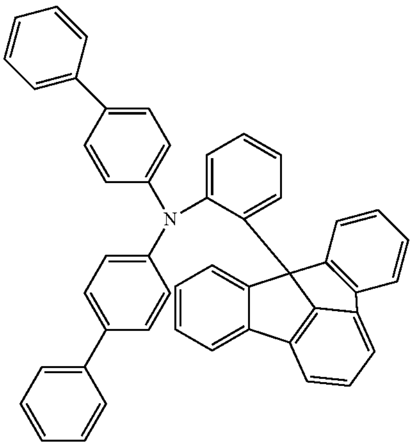 [SMILES: c1ccc(-c2ccc(N(c3ccc(-c4ccccc4)cc3)c3ccccc3C34c5ccccc5-c5cccc(c53)-c3ccccc34)cc2)cc1]
HTM5
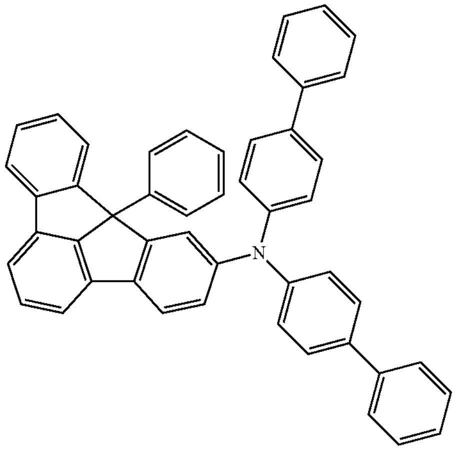 [SMILES: c1ccc(-c2ccc(N(c3ccc(-c4ccccc4)cc3)c3ccc4c(c3)C3(c5ccccc5)c5ccccc5-c5cccc-4c53)cc2)cc1]
HTM6

TABLE 1-continued

| Structures of the materials used |
|---|
| 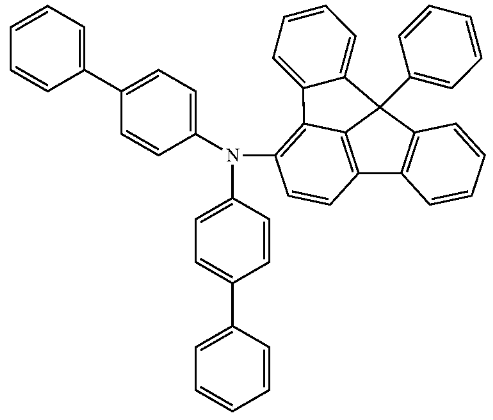 HTM7 |

OLED Example 2

A green-phosphorescing reference sample C2 was produced and compared with inventive samples I8 to I12. Reference sample C2 at a current density of 2 $mA/cm^2$ has an external quantum efficiency of 11.7% and a lifetime (LD80 @ 20 $mA/cm^2$) of 80 h. By comparison, the inventive samples I8 (17.2%, 135 h), I9 (18.7%, 110 h), I10 (17.4%, 145 h), I11 (19.0%, 105 h) and I12 (20.2%, 160 h) have both better external quantum efficiency at a current density of 2 $mA/cm^2$ and a longer lifetime (LD80 @ 20 $mA/cm^2$).

The invention claimed is:

1. A compound of formula (1)

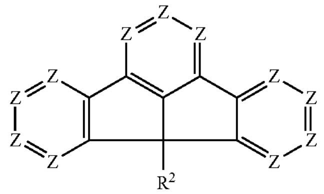

TABLE 2

| Structure of the OLEDs | | | | | | | |
|---|---|---|---|---|---|---|---|
| Ex. | HIL1 Thickness/ nm | HTL Thickness/ nm | HIL2 Thickness/ nm | EBL Thickness/ nm | EML Thickness/ nm | ETL Thickness/ nm | EIL Thickness/ nm |
| C1 | HIM1:F4TCNQ(3%) 20 nm | HIM1 155 nm | NPB:F4TCNQ(3%) 20 nm | NPB 20 nm | H1:SEB(5%) 20 nm | ETM(50%):LiQ(50%) 30 nm | LiQ 1 nm |
| I1 | HIM1:F4TCNQ(3%) 20 nm | HIM1 155 nm | HTM1:F4TCNQ(3%) 20 nm | HTM1 20 nm | H1:SEB(5%) 20 nm | ETM(50%):LiQ(50%) 30 nm | LiQ 1 nm |
| I2 | HIM1:F4TCNQ(3%) 20 nm | HIM1 155 nm | HTM2:F4TCNQ(3%) 20 nm | HTM2 20 nm | H1:SEB(5%) 20 nm | ETM(50%):LiQ(50%) 30 nm | LiQ 1 nm |
| I3 | HIM1:F4TCNQ(3%) 20 nm | HIM1 155 nm | HTM3:F4TCNQ(3%) 20 nm | HTM3 20 nm | H1:SEB(5%) 20 nm | ETM(50%):LiQ(50%) 30 nm | LiQ 1 nm |
| I4 | HIM1:F4TCNQ(3%) 20 nm | HIM1 155 nm | HTM4:F4TCNQ(3%) 20 nm | HTM4 20 nm | H1:SEB(5%) 20 nm | ETM(50%):LiQ(50%) 30 nm | LiQ 1 nm |
| I5 | HIM1:F4TCNQ(3%) 20 nm | HIM1 155 nm | HTM5:F4TCNQ(3%) 20 nm | HTM5 20 nm | H1:SEB(5%) 20 nm | ETM(50%):LiQ(50%) 30 nm | LiQ 1 nm |
| I6 | HIM1:F4TCNQ(3%) 20 nm | HIM1 155 nm | HTM6:F4TCNQ(3%) 20 nm | HTM6 20 nm | H1:SEB(5%) 20 nm | ETM(50%):LiQ(50%) 30 nm | LiQ 1 nm |
| I7 | HIM1:F4TCNQ(3%) 20 nm | HIM1 155 nm | HTM7:F4TCNQ(3%) 20 nm | HTM7 20 nm | H1:SEB(5%) 20 nm | ETM(50%):LiQ(50%) 30 nm | LiQ 1 nm |
| C2 | HIM1:F4TCNQ(3%) 20 nm | HIM1 210 nm | NPB:F4TCNQ(3%) 20 nm | NPB 20 nm | H2:TEG(5%) 30 nm | ETM(50%):LiQ(50%) 40 nm | LiQ 1 nm |
| I8 | HIM1:F4TCNQ(3%) 20 nm | HIM1 210 nm | HTM1:F4TCNQ(3%) 20 nm | HTM1 20 nm | H2:TEG(5%) 30 nm | ETM(50%):LiQ(50%) 40 nm | LiQ 1 nm |
| I9 | HIM1:F4TCNQ(3%) 20 nm | HIM1 210 nm | HTM2:F4TCNQ(3%) 20 nm | HTM2 20 nm | H2:TEG(5%) 30 nm | ETM(50%):LiQ(50%) 40 nm | LiQ 1 nm |
| I10 | HIM1:F4TCNQ(3%) 20 nm | HIM1 210 nm | HTM3:F4TCNQ(3%) 20 nm | HTM3 20 nm | H2:TEG(5%) 30 nm | ETM(50%):LiQ(50%) 40 nm | LiQ 1 nm |
| I11 | HIM1:F4TCNQ(3%) 20 nm | HIM1 210 nm | HTM4:F4TCNQ(3%) 20 nm | HTM4 20 nm | H2:TEG(5%) 30 nm | ETM(50%):LiQ(50%) 40 nm | LiQ 1 nm |
| I12 | HIM1:F4TCNQ(3%) 20 nm | HIM1 210 nm | HTM5:F4TCNQ(3%) 20 nm | HTM5 20 nm | H2:TEG(5%) 30 nm | ETM(50%):LiQ(50%) 40 nm | LiQ 1 nm |

OLED Example 1

A blue-fluorescing reference sample C1 was produced and compared with inventive samples I1 to I7. Reference sample C1 at a current density of 10 $mA/cm^2$ has an external quantum efficiency of 6.2% and a lifetime (LD80 @ 60 $mA/cm^2$) of 120 h. By comparison, the inventive samples I1 (7.5%, 160 h), I2 (7.8%, 250 h), I3 (7.6%, 210 h), I4 (7.4%, 200 h), I5 (8.0%, 235 h), I6 (7.7%, 270 h) and I7 (7.1%, 260 h) have both better external quantum efficiency at a current density of 10 $mA/cm^2$ and a longer lifetime (LD80 @ 60 $mA/cm^2$).

where

Z is the same or different at each instance, and is $CR^1$ or N;

$R^1$ is the same or different at each instance, and is H, D, F, Cl, Br, I, CN, $NO_2$, $N(Ar^1)_2$, $N(R^3)_2$, $C(=O)Ar^1$, $C(=O)R^3$, $P(=O)(Ar^1)_2$, $P(=O)(R^3)_2$, $B(OR^3)_2$, CHO, $Si(R^3)_2$, $OSO_2R^3$, $S(=O)R^3$, $S(=O)_2R^3$, a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, where the alkyl, alkoxy, thioalkyl, alkenyl or alkynyl group are optionally substituted in each case with one or more $R^3$ radicals, and where one or more adjacent or nonadjacent —$CH_2$— groups may be replaced by $R^3C{=}CR^3$, C≡C, C═O, C═S, C═Se, C═$NR^3$, C(═O)$NR^3$, P(═O)($R^3$), C(═O)O, Si($R^3$)$_2$, $NR^3$, O, S, SO or $SO_2$ and where one or more hydrogen atoms may be replaced by D, F, Cl, Br, I, CN or $NO_2$, or an aromatic ring system which has 6 to 60 aromatic ring atoms and is optionally substituted in each case by one or more $R^3$, or a heteroaromatic ring system which has 5 to 60 aromatic ring atoms and which is optionally substituted in each case by one or more $R^3$, where two or more $R^1$ radicals may be joined to one another and may form a ring;

$Ar^1$ is the same or different at each instance and is an aromatic or heteroaromatic ring system which has 5 to 60 aromatic ring atoms, and which is optionally substituted by one or more $R^3$ radicals; at the same time, two $Ar^1$ radicals bonded to the same nitrogen atom or phosphorus atom may also be bridged to one another by a single bond or a bridge selected from N($R^4$), C($R^4$)$_2$, O and S;

$R^2$ is the same or different at each instance, and is H, D, F, Cl, Br, I, CN, $NO_2$, N($Ar^1$)$_2$, N($R^3$)$_2$, C(═O)$Ar^1$, C(═O)$R^3$, P(═O)($Ar^1$)$_2$, P(═O)($R^3$)$_2$, B($OR^3$)$_2$, CHO, Si($R^3$)$_2$, $OSO_2R^3$, S(═O)$R^3$, S(═O)$_2R^3$, a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, where the alkyl, alkoxy, thioalkyl, alkenyl or alkynyl group may be substituted in each case by one or more $R^3$ radicals and where one or more adjacent or nonadjacent $CH_2$ groups may be replaced by —$R^3C{=}CR^3$—, —C≡C—, C═O, C═S, C═Se, C═$NR^3$, —C(═O)—$NR^3$—, P(═O)($R^3$), —C(═O)—O—, Si($R^3$)$_2$, $NR^3$, —O—, —S—, SO or $SO_2$ and where one or more hydrogen atoms may be replaced by D, F, Cl, Br, I, CN or $NO_2$, or an aromatic ring system which has 6 to 60 aromatic ring atoms and may be substituted in each case by one or more $R^3$ radical(s), or a heteroaromatic ring system which has 5 to 60 aromatic ring atoms and may be substituted in each case by one or more $R^3$ radical(s);

$R^3$ is the same or different at each instance, and is H, D, F, Cl, Br, I, CN, $NO_2$, N($R^4$)$_2$, C(═O)$Ar^1$, C(═O)$R^4$, P(═O)($Ar^1$)$_2$, B($OR^4$)$_2$, CHO, Si($R^4$)$_2$, $OSO_2R^4$, S(═O)$R^4$, S(═O)$_2R^4$, a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, where the alkyl, alkoxy, thioalkyl, alkenyl or alkynyl group is optionally substituted in each case by one or more $R^4$ radicals and where one or more adjacent or nonadjacent —$CH_2$— groups may be replaced by $R^4C{=}CR^4$, C═C, C═O, C═S, C═Se, C═$NR^4$, C(═O)$NR^4$, P(═O)($R^4$), C(═O)O, Si($R^4$)$_2$, $NR^4$, O, S, SO or $SO_2$ and where one or more hydrogen atoms may be replaced by D, F, Cl, Br, I, CN or $NO_2$, or an aromatic ring system which has 6 to 60 aromatic ring atoms and which is optionally substituted in each case by one or more $R^4$ radical(s), or a heteroaromatic ring system which has 5 to 60 aromatic ring atoms and which is optionally substituted in each case by one or more $R^4$ radical(s), where two or more $R^4$ radicals may be joined to one another and may form a ring;

$R^4$ is the same or different at each instance, and is H, D, F, CN or an aliphatic radical having 1 to 20 carbon atoms, or an aromatic ring system having 6 to 60 aromatic ring atoms or a heteroaromatic ring system having 5 to 60 aromatic ring atoms, where one or more hydrogen atoms in the aliphatic radical, the aromatic ring system or the heteroaromatic ring system may be replaced by D, F, Cl, Br, I, CN or an alkyl group having 1 to 5 carbon atoms, where two or more $R^4$ radicals may be joined to one another and may form a ring;

where $R^2$ and/or at least one $R^1$ of the formula (1) comprises at least one aromatic or heteroaromatic ring system; and if at least one $R^1$ comprises at least one aromatic or heteroaromatic ring system, the total number of aromatic ring atoms in all $R^1$ and $R^2$ is at least 12; and if $R^1$ does not comprise an aromatic or heteroaromatic ring system, $R^2$ comprises at least 24 aromatic ring atoms and no further indeno[1,2,3-jk]fluorene skeleton.

2. The compound of claim 1, where $R^1$ at least one of positions 5 and 10 in the indeno[1,2,3-jk]fluorene skeleton is the same or different at each instance and is H, D, F, CN, $NO_2$, N($Ar^1$)$_2$, N($R^3$)$_2$, C(═O)$Ar^1$, P(═O)($Ar^1$)$_2$, P(═O)($R^3$)$_2$, Si($R^3$)$_2$, $OSO_2R^3$, S(═O)$R^3$, S(═O)$_2R^3$, a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, where the alkyl, alkoxy, thioalkyl, alkenyl or alkynyl group is optionally substituted in each case by one or more $R^3$ radicals and where one or more adjacent or nonadjacent —$CH_2$— groups may be replaced by $R^3C{=}CR^3$, C═C, C═O, C═S, C═Se, C═$NR^3$, C(═O)$NR^3$, P(═O)($R^3$), C(═O)O, Si($R^3$)$_2$, $NR^3$, O, S, SO or $SO_2$ and where one or more hydrogen atoms may be replaced by D, F, Cl, Br, I, CN or $NO_2$, or an aromatic ring system which has 6 to 60 aromatic ring atoms, which is optionally substituted in each case by one or more $R^3$, or a heteroaromatic ring system which has 5 to 60 aromatic ring atoms and is optionally substituted in each case by one or more $R^3$, where two or more $R^1$ radicals may be joined to one another and may form a ring.

3. The compound of claim 2, where $R^1$ at positions 5 and 10 of the indeno[1,2,3-jk]fluorene skeleton, if present in each case, does not contain any radicals selected from the group comprising Cl, Br, I, B($OR^3$)$_2$ and CHO.

4. The compound of claim 1, where at least one $R^1$ is not H.

5. The compound of claim 1, where at least one $R^1$ comprises an aromatic or heteroaromatic ring system.

6. The compound of claim 1, where $R^2$ is a heteroaromatic ring system, and comprises a triarylamine group or triheteroarylamine group or a carbazole structure bonded directly to the indeno[1,2,3-jk]fluorene skeleton, the nitrogen atom is arranged in the meta or ortho position in relation to the indeno[1,2,3-jk]fluorene skeleton.

7. A process for preparing the compound of claim 1, where the base skeleton of the formula (1) is constructed by one or more coupling reactions.

8. An oligomer, polymer or dendrimer containing one or more compounds of claim 1, characterized in that the bonds to the oligomer, polymer or dendrimer may be localized at any desired positions substituted by $R^1$ and/or $R^2$ in formula (1).

9. A formulation comprising at least one compound of claim 1 and at least one solvent.

10. A formulation comprising at least one polymer, oligomer or dendrimer of claim 8 and at least one solvent.

11. An electronic device comprising at least one compound of claim 1.

12. An electronic device comprising at least one polymer, oligomer or dendrimer as claimed in claim 8.

13. The electronic device of claim 11, selected from the group consisting of organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and organic electroluminescent devices (OLEDs).

14. An organic electroluminescent device (OLED) comprising at least one compound of claim 1, which is present in the device as a hole transport material in a hole transport or hole injection layer,
a hole injection material,
a hole blocker material,
an emitter for fluorescent emission layers,
a matrix material in an emitting layer,
an electron blocker material, or
a material for an interlayer.

15. An organic electroluminescent device (OLED) comprising at least one polymer, oligomer or dendrimer of claim 8, which is present in the device as a hole transport material in a hole transport or hole injection layer,
a hole injection material,
a hole blocker material,
an emitter for fluorescent emission layers,
a matrix material in an emitting layer,
an electron blocker material, or
a material for an interlayer.

* * * * *